US009051575B2

(12) United States Patent  
Ogawa et al.

(10) Patent No.: US 9,051,575 B2  
(45) Date of Patent: Jun. 9, 2015

(54) ALGA IN WHICH PRODUCTION OF PHOTOSYNTHETIC PRODUCTS IS IMPROVED, AND USE FOR SAID ALGA

(75) Inventors: Kenichi Ogawa, Kyoto (JP); Masanobu Nishikawa, Okayama (JP)

(73) Assignee: Japan Science and Technology Agency, Kawaguchi-Shi (JP)

( * ) Notice: Subject to any disclaimer, the term of this patent is extended or adjusted under 35 U.S.C. 154(b) by 0 days.

(21) Appl. No.: 13/817,360

(22) PCT Filed: Aug. 29, 2011

(86) PCT No.: PCT/JP2011/069501  
§ 371 (c)(1),  
(2), (4) Date: Feb. 15, 2013

(87) PCT Pub. No.: WO2012/029727  
PCT Pub. Date: Mar. 8, 2012

(65) Prior Publication Data  
US 2013/0143260 A1 Jun. 6, 2013

(30) Foreign Application Priority Data

Aug. 31, 2010 (JP) ................................ 2010-194210

(51) Int. Cl.
| | |
|---|---|
| *C12N 1/20* | (2006.01) |
| *C12N 9/88* | (2006.01) |
| *C12N 15/79* | (2006.01) |
| *C12P 19/04* | (2006.01) |
| *C12N 15/82* | (2006.01) |
| *C12N 9/00* | (2006.01) |
| *C12N 1/12* | (2006.01) |

(52) U.S. Cl.  
CPC ................. *C12N 15/79* (2013.01); *C12P 19/04* (2013.01); *C12N 15/8245* (2013.01); *C12Y 603/02002* (2013.01); *C12N 9/93* (2013.01); *C12N 1/12* (2013.01)

(58) Field of Classification Search  
CPC ..................... G01N 33/57415; G01N 33/6875  
USPC ......................................... 435/34, 257.2, 232  
See application file for complete search history.

(56) References Cited

U.S. PATENT DOCUMENTS

| | | | |
|---|---|---|---|
| 5,578,472 | A | 11/1996 | Ueda et al. |
| 7,034,202 | B1 | 4/2006 | Terry et al. |
| 2002/0016983 | A1 | 2/2002 | Terry et al. |
| 2004/0123341 | A1 | 6/2004 | Brunold et al. |
| 2010/0083404 | A1 | 4/2010 | Ogawa et al. |
| 2010/0242141 | A1 | 9/2010 | Ogawa |

FOREIGN PATENT DOCUMENTS

| | | |
|---|---|---|
| CA | 2 355 255 | 6/2000 |
| JP | 64-051098 | 2/1989 |
| JP | 7-87983 | 4/1995 |
| JP | 11-69989 A | 3/1999 |
| JP | 11-196885 A | 7/1999 |
| JP | 2003-310288 A | 11/2003 |
| JP | 2010-088334 A | 4/2010 |
| WO | WO-00/36127 | 6/2000 |
| WO | WO-01/49855 | 7/2001 |
| WO | WO-02/33105 | 4/2002 |
| WO | WO-2008087932 A1 | 7/2008 |
| WO | WO-2009063806 A1 | 5/2009 |
| WO | WO-2009153439 A2 | 12/2009 |

OTHER PUBLICATIONS

Wang et al., Algal Lipid Bodies: Stress Induction, Purification, and Biochemical Characterization in Wild-Type and Starchless Chlamydomonas reinhardtii. Eukaryotic Cell. 8: 12, 1856-1868, 2009.*

Guo et al., Overexpressing GSH1 and AsPCS1 simultaneously increases the tolerance and accumulation of cadmium and arsenic in Arabidopsis thaliana. Chemosphere. 72: 1020-1021, 2008.*

Noctor et al., Manipulation of Glutathione and Amino Acid Biosynthesis in the Chloroplast Plant Physiol. 118: 471-482, 1998.*

Ogawa. Glutathione-Associated Regulation of Plant Growth and Stress Responses. Antioxidants & redox signaling. vol. 7, Nos. 7 & 8, 2005.*

Noctor et al., Manipulation of Glutathione and Amino Acid Biosynthesis in the Chloroplast. Plant Physiol. 118: 471-482, 1998.*

Wang, et al., "Algal Lipid Bodies: Stress Induction, Purification, and Biochemical Characterization in Wild-Type and Starchless *Chlamydomonas reinhardtii*", *Eukaryotic Cell*, vol. 8, No. 12, Dec. 2009: pp. 1856-1868.

Li et al., "*Chlalmydomanas* starchless mutant defective in ADP-glucose pyrophosphorylase hyper-accumulates triacylglycerol", *Metabolic Engineering*, vol. 12, (4), 2010, pp. 387-391.

Hyams, et al. "The Induction of Characterization of Cell Wall Mutants of *Chlamydomonas Reinhardi*", *Mutation Research* 14 (4), 1972, pp. 381-389.

Ball, et al., "Physiology of Starch Storage in the Monocellular Alga *Chlamydomonas Reinhardtii*", *Plant Science* vol. 66, No. 1, 1990, pp. 1-9.

Fischer, et al, "The flanking regions of a PsaD drive efficient gene expression in the nucleus of the green alga *Chlamydomonas reinhardtii*", *Mol Genet Genomics* (2001) vol. 265, No. 5, 2001, pp. 888-894.

Database DDBJ/EMBLL/GenBank, Accession No. XM_001701595, "*Chlamydomonas reinhardtii* gamma-glutamylcysteine synthetase (GSH1) mRNA, complete cds" Nov. 14, 2011.

International Search Report in International Application No. PCT/JP2011/069501, mailed Nov. 29, 2011.

Bhattacharya and Medlin. "The Phylogeny of Plastids: A Review Based on Comparisons of Small-Subunit Ribosomal RNA Coding Regions." *J. Phycol* 31, 489-498 (1995).

(Continued)

*Primary Examiner* — Tekchand Saidha  
(74) *Attorney, Agent, or Firm* — Locke Lord LLP

(57) ABSTRACT

Provided are an alga in which productivity of a photosynthate is increased, and use of the alga. The alga of the present invention has an increased glutathione concentration in its chloroplast. A method of the present invention for producing biomass is a method for producing biomass with the use of the alga of the present invention or an alga produced by a method of the present invention for producing an alga.

12 Claims, 17 Drawing Sheets

(56) References Cited

OTHER PUBLICATIONS

Hara "Phylogenetic classification of Alga" *Chemistry and Biology*, Japan Society for Bioscience, Biotechnology, and Agrochemistry, vol. 40, No. 8, pp. 552-557 (2002). (Including Partial English Translation).

NCBI Reference Sequence: XP_001701647.1, gamma-glutamylcysteine synthetase [Chlamydomonas reinhardtii].

Siripornadulsil et al., "Molecular Mechanisms of Proline-Mediated Tolerance to Toxic Heavy Metals in Transgenic Microalgae", The Plant Cell, vol. 14, 2837-2847, Nov. 2002.

Office Action mailed Sep. 11, 2014, in corresponding Korean patent application No. 10-2013-7004876.

Japanese Office Action mailed Jul. 8, 2014, in corresponding Japanese Patent Application No. 2012-531869 (with English translation).

Walker et al., "Microalgae as bioreactors", Plant Cell Rep., 24:629-641 (2005).

* cited by examiner

SEQUENCE LISTING

```
<160> NUMBER OF SEQ ID NOS: 18

<210> SEQ ID NO 1
<211> LENGTH: 479
<212> TYPE: PRT
<213> ORGANISM: Chlamydomonas reinhardtii

<400> SEQUENCE: 1

Met Ala Leu Ala Ser Gly Val Gly Arg Arg Gln His Val Ser Ala Ser
1               5                   10                  15

Pro Ser Arg Ser Arg Gly Val Pro Ser Pro Arg Leu Ser Pro Val His
                20                  25                  30

Ala Asn Ala Pro Ala Val Ala Glu Arg Arg Thr Glu Pro Leu Leu Lys
            35                  40                  45

Gln Glu Leu Val Asp Tyr Leu Lys Ser Gly Cys Arg Pro Arg Ser Ala
        50                  55                  60

Trp Arg Ile Gly Thr Glu His Glu Lys Leu Gly Phe Asn Leu Ala Asp
65                  70                  75                  80

Asn Ser Arg Met Asn Tyr Asp Gln Ile Ala Gln Val Leu Arg Lys Leu
                85                  90                  95

Glu Ala Arg Phe Gly Trp Glu Pro Ile Met Glu Glu Gly Arg Ile Ile
            100                 105                 110

Gly Val Gln Leu Asp Gly Gln Ser Val Thr Leu Glu Pro Gly Gly Gln
        115                 120                 125
```

Phe Glu Leu Ser Gly Ala Pro Val Glu Thr Ile His Lys Thr Cys Ala
    130                 135                 140

Glu Val Asn Ser His Leu Tyr Gln Val Lys Ala Ile Cys Glu Glu Leu
145                 150                 155                 160

Gln Thr Gly Phe Leu Gly Val Gly Phe Asp Pro Lys Trp Ala Ile Ser
                165                 170                 175

Asp Val Pro Met Met Pro Lys Gly Arg Tyr Lys Leu Met Lys Ser Tyr
            180                 185                 190

Met Pro Thr Val Gly Ser Met Gly Leu Asp Met Met Phe Arg Thr Cys
        195                 200                 205

Thr Val Gln Val Asn Leu Asp Phe Glu Ser Glu Gln Asp Met Val Glu
    210                 215                 220

Lys Phe Arg Ile Gly Leu Ala Leu Gln Pro Ile Ala Asn Ala Leu Phe
225                 230                 235                 240

Ala Ser Ser Pro Phe Lys Glu Gly Lys Pro Thr Gly Tyr Leu Ser Thr
                245                 250                 255

Arg Gly His Val Trp Thr Asp Val Asp Ala Ser Arg Thr Gly Asn Leu
            260                 265                 270

Pro Phe Val Phe Glu Lys Asp Met Cys Phe Glu Ser Tyr Val Asp Tyr
        275                 280                 285

Ala Met Ala Val Pro Met Tyr Phe Val Tyr Arg Asn Gly Gln Tyr Ile
    290                 295                 300

Asn Ala Leu Gly Met Ser Trp Lys Asp Phe Met Ala Gly Lys Leu Pro
305                 310                 315                 320

Ala Leu Pro Gly Glu Tyr Pro Thr Ile Ala Asp Trp Ala Asn His Leu
                325                 330                 335

Thr Thr Ile Phe Pro Glu Val Arg Leu Lys Lys Phe Leu Glu Met Arg
            340                 345                 350

Gly Ala Asp Gly Gly Pro Trp Arg Met Leu Cys Ala Leu Pro Ala Leu
        355                 360                 365

Trp Val Gly Leu Ile Tyr Asp Pro Glu Ala Gln Arg Gln Ala Leu Ala
    370                 375                 380

Leu Ile Glu Asp Trp Thr Pro Ala Glu Arg Asp Tyr Leu Arg Thr Glu
385                 390                 395                 400

Val Thr Arg Phe Gly Leu Arg Thr Pro Phe Arg Ala Gly Thr Val Gln
                405                 410                 415

Asp Val Ala Lys Gln Val Val Ser Ile Ala His Gly Gly Leu Glu Arg
            420                 425                 430

Arg Gly Tyr Asp Glu Thr Ser Phe Leu Lys Arg Leu Glu Val Ile Ala
        435                 440                 445

Glu Thr Gly Leu Thr Gln Ala Asp His Leu Leu Glu Leu Tyr Glu Thr
    450                 455                 460

Lys Trp Gln Arg Ser Val Asp Pro Leu Tyr Lys Glu Phe Met Tyr
465                 470                 475

<210> SEQ ID NO 2
<211> LENGTH: 1440
<212> TYPE: DNA
<213> ORGANISM: Chlamydomonas reinhardtii

<400> SEQUENCE: 2
atggctctcg cctcaggcgt tggccgtcgc cagcatgtgt cggcctcgcc ctcgcgcagt     60
cggggtgtgc caagcccacg cttgagccct gtccacgcga acgcgcctgc ggttgcggag    120

-continued

| | |
|---|---|
| cgtcgcacag agccctctct taaagcaggag ctggtggatt acctgaaatc ggggtgtagg | 180 |
| cctcgcagcg cgtggcgaat cggcaccgag cacgagaagc tgggtttcaa cctggcagac | 240 |
| aacagccgca tgaactacga ccagattgca caggtgctac gcaagctgga ggcccggttt | 300 |
| ggttgggagc ccatcatgga ggagggccgt atcatcggcg tgcagttgga tggtcagagt | 360 |
| gtgacgctgg agcccggcgg ccagtttgaa ctgagcgggg cgcccgtgga gaccattcac | 420 |
| aagacgtgtg cggaggtgaa cagccacctc taccaggtca aggccatctg cgaggagctt | 480 |
| cagacaggat tcctgggcgt gggctttgac cccaagtggg ccatcagcga cgttcccatg | 540 |
| atgcccaagg ccgctacaa gctgatgaag tcgtacatgc ccacggtggg ctccatgggc | 600 |
| ctggacatga tgttccgcac atgcaccgtg caggtgaacc tggactttga gagcgagcag | 660 |
| gacatggtgg agaagttccg catcggcctg cgctgcagc ccatcgccaa cgcgctcttc | 720 |
| gccagctcgc cattcaagga gggcaagccc accgggtacc tgagcacccg cggtcacgtg | 780 |
| tggacggacg tggacgcctc gcgcaccggc aacctgccgt tcgtgttcga aggacatg | 840 |
| tgcttcgaga gctacgtgga ctacgccatg gcggtgccca tgtacttcgt gtaccgcaac | 900 |
| gggcagtaca tcaacgcgct gggcatgagc tggaaggact tcatggccgg caagctgccc | 960 |
| gcgctgccgg gcgaataccc caccatcgcc gactgggcca accacctgac caccatcttc | 1020 |
| cccgaggtgc ggctcaagaa gttcctggag atgcgcggcg cggacggcgg cccctggcgc | 1080 |
| atgctgtgcg cgctgccggc gctgtgggtg gggctcatat acgatccgga ggcgcagcgc | 1140 |
| caggccctgg cgctgattga ggattggacg cccgcggagc gcgactacct gcgcaccgag | 1200 |
| gtgacccgct tcggcctgcg cacgcccttc gcgccggca ccgtgcagga cgtggccaag | 1260 |
| caggtggtgt ccatcgcgca cggcggcctg gagcggcgag gctacgacga cgtccttc | 1320 |
| ctcaagcgcc tggaggtcat cgcggagact ggcctcacac aggccgacca cctgcttgag | 1380 |
| ctgtacgaga ccaagtggca gcgctcggtg gacccgctgt acaaggagtt catgtactga | 1440 |

<210> SEQ ID NO 3
<211> LENGTH: 2403
<212> TYPE: DNA
<213> ORGANISM: Chlamydomonas reinhardtii

<400> SEQUENCE: 3

| | |
|---|---|
| gagtgtcatt actacttgat aagaatcacc agcacttggg cgaccacagc gagcgaacga | 60 |
| ttattcttca ctgttacgtt gcactacatc ttggccctgt tccgatcaat ccctaggctg | 120 |
| ccgcactagt gcgatggctc tcgcctcagg cgttggccgt cgccagcatg tgtcggcctc | 180 |
| gccctcgcgc agtcggggtg tgccaagccc acgcttgagc cctgtccacg cgaacgcgcc | 240 |
| tgcggttgcg gagcgtcgca cagagcccct cttaaagcag gagctggtgg attacctgaa | 300 |
| atcggggtgt aggcctcgca gcgcgtggcg aatcggcacc gagcacgaga gctgggttt | 360 |
| caacctggca gacaacagcc gcatgaacta cgaccagatt gcacaggtgc tacgcaagct | 420 |
| ggaggcccgg tttggttggg agcccatcat ggaggagggc cgtatcatcg gcgtgcagtt | 480 |
| ggatggtcag agtgtgacgc tggagcccgg cggccagttt gaactgagcg gggcgcccgt | 540 |
| ggagaccatt cacaagacgt gtgcggaggt gaacagccac ctctaccagg tcaaggccat | 600 |
| ctgcgaggag cttcagacag gattcctggg cgtgggcttt gaccccaagt gggccatcag | 660 |
| cgacgttccc atgatgccca agggccgcta caagctgatg aagtcgtaca tgcccacggt | 720 |
| gggctccatg ggcctggaca tgatgttccg cacatgcacc gtgcaggtga acctggactt | 780 |
| tgagagcgag caggacatgg tggagaagtt ccgcatcggc ctggcgctgc agcccatcgc | 840 |

```
caacgcgctc ttcgccagct cgccattcaa ggagggcaag cccaccgggt acctgagcac    900
ccgcggtcac gtgtggacgg acgtggacgc ctcgcgcacc ggcaacctgc cgttcgtgtt    960
cgagaaggac atgtgcttcg agagctacgt ggactacgcc atggcggtgc ccatgtactt   1020
cgtgtaccgc aacgggcagt acatcaacgc gctgggcatg agctggaagg acttcatggc   1080
cggcaagctg cccgcgctgc cgggcgaata ccccaccatc gccgactggg ccaaccacct   1140
gaccaccatc ttccccgagg tgcggctcaa gaagttcctg gagatgcgcg cgcggacgg    1200 cggcccctgg cgcatgctgt gcgcgctgcc ggcgctgtgg gtgggctca tatacgatcc    1260 ggaggcgcag cgccaggccc tggcgctgat tgaggattgg acgcccgcgg agcgcgacta   1320
cctgcgcacc gaggtgaccc gcttcggcct gcgcacgccc ttccgcgccg gcaccgtgca   1380
ggacgtggcc aagcaggtgg tgtccatcgc gcacggcggc ctggagcggc gaggctacga   1440
cgagacgtcc ttcctcaagc gcctggaggt catcgcggag actggcctca cacaggccga   1500
ccacctgctt gagctgtacg agaccaagtg gcagcgctcg gtggacccgc tgtacaagga   1560
gttcatgtac tgagcaggag gaggggcagc ggcagcagca gcaggaggtg cggcggagc    1620 aggaggaagt gtatcggtat gtcggaaaga cgacgttaag tgacttgaaa gtgatgtttg   1680
cgagaggctg atgcctgtgc cgtttgatgt gagtgtgagt actgcgccag tattcgctgt   1740
tcgcaacggc gttaccaaca tattgcggtg ggatgcatag ttgatcagtt tggttgtgcc   1800
aacccaacat ttctcgcttg gctgatgca tgggcgaact gccgaatgcc tgggtggcgc    1860
tgggggtcag caacatgaag cttgttgtgt gtacagccag accagcttga aggaagacca   1920
gcttgaagga atgagctcgg cctcgagcgt tgtgacaatc gtgctgtcgt gcggacaaca   1980
tattatgttg gtgtgccctc cgatgttatg aacttgcttc gcgtgggatg cgaacgcagg   2040
tacaggtaga gacctcaaac ggtgacaggg acgggtctgg ggcggaaacc tatgggtatc   2100
aggcgatctg atcaagaggt ggatccgctt gggacatagc acgcgtgcgt cgtacgatga   2160
ggcaatcggg cctgtgcccc ggttcctcag gcagtcaggc gccgggttag tgcggcgatg   2220
aagtacggta tagtgcctac tcagtgcatc gggcggcggt gcggatatgg gcttcacccg   2280
tgcgttgcgt gaagcttttg gggtcgtgtg gcttcgctgt gcggcgtgcc agacgaggct   2340
ccgagatggt gctgaactgg ttgtgaaggt ggccggttcg gacttgtaag gccctcgctc   2400
agg                                                                 2403

<210> SEQ ID NO 4
<211> LENGTH: 3130
<212> TYPE: DNA
<213> ORGANISM: Chlamydomonas reinhardtii

<400> SEQUENCE: 4
atcagcacac acagcaggct cactgccgcg gatcccacac acctgcccgt ctgcctgaca     60
ggaagtgaac gcatgtcgag ggaggcctca ccaatcgtca cacgagccct cgtcagaaac    120
acgtctccgc cacgctctcc ctctcacggc cgaccccgca gcccttttgc cctttcctag    180
gccaccgaca ggacccaggc gctctcagca tgcctcaaca acccgtactc gtgccagcgg    240
tgcccttgtg ctggtgatcg cttggaagcg catgcgaaga cgaaggggcg gagcaggcgg    300
cctggctgtt cgaagggctc gccgccagtt cgggtgcctt tctccacgcg cgcctccaca    360
cctaccgatg cgtgaaggca ggcaaatgct catgtttgcc cgaactcgga gtccttaaaa    420
agccgcttct tgtcgtcgtt ccgagacatg ttagcagatc gcagtgccac ctttcctgac    480
```

```
gcgctcggcc ccatattcgg acgcaattgt catttgtagc acaattggag caaatctggc      540
gaggcagtag gcttttaagt tgcaaggcga gagagcaaag tgggacgcgg cgtgattatt      600
ggtatttacg cgacggcccg cgcgttagc ggcccttccc ccaggccagg gacgattatg      660
tatcaatatt gttgcgttcg ggcactcgtg cgagggctcc tgcgggctgg ggagggggat      720
ctgggaattg gaggtacgac cgagatggct tgctcggggg gaggtttcct cgccgagcaa      780
gccaggggta ggtgttgcgc tcttgactcg ttgtgcattc taggacccca ctgctactca      840
caacaagcca aaatggttgc tctcgcctca ggcgttggcc gtcgccagca tgtgtcggcc      900
tcgccctcgc gcagtcgggg tgtgccaagc ccacgcttga gccctgtcca cgcgaacgcg      960
cctgcggttg cggagcgtcg cacagagccc ctcttaaagc aggagctggt ggattacctg     1020 aaatcgggt gtaggcctcg cagcgcgtgg cgaatcggca ccgagcacga aagctgggt      1080 ttcaacctgg cagacaacag ccgcatgaac tacgaccaga ttgcacaggt gctacgcaag     1140
ctggaggccc ggtttggttg ggagcccatc atggaggagg ccgtatcat cggcgtgcag      1200 ttggatggtc agagtgtgac gctggagccc ggcggccagt ttgaactgag cggggcgccc     1260
gtggagacca ttcacaagac gtgtgcggag gtgaacagcc acctctacca ggtcaaggcc     1320
atctgcgagg agcttcagac aggattcctg gcgtgggct tgaccccaa gtgggccatc      1380 agcgacgttc ccatgatgcc caagggccgc tacaagctga tgaagtcgta catgcccacg     1440
gtgggctcca tgggcctgga catgatgttc cgcacatgca ccgtgcaggt gaacctggac     1500
tttgagagcg agcaggacat ggtggagaag ttccgcatcg gcctggcgct gcagcccatc     1560
gccaacgcgc tcttcgccag ctcgccattc aaggagggca agcccaccgg gtacctgagc     1620
acccgcggtc acgtgtggac ggacgtggac gcctcgcgca ccggcaacct gccgttcgtg     1680
ttcgagaagg acatgtgctt cgagagctac gtggactacg ccatggcggt gcccatgtac     1740
ttcgtgtacc gcaacgggca gtacatcaac gcgctgggca tgagctggaa ggacttcatg     1800
gccggcaagc tgcccgcgct gccgggcgaa taccccacca tcgccgactg ggccaaccac     1860
ctgaccacca tcttccccga ggtgcggctc aagaagttcc tggagatgcg cggcgcggac     1920 ggcggccccct ggcgcatgct gtgcgcgctg ccggcgctgt gggtggggct catatacgat     1980
ccggaggcgc agcgccaggc cctggcgctg attgaggatt ggacgcccgc ggagcgcgac     2040
tacctgcgca ccgaggtgac ccgcttcggc ctgcgcacgc ccttccgcgc cggcaccgtg     2100
caggacgtgg ccaagcaggt ggtgtccatc gcgcacggcg gcctggagcg gcgaggctac     2160
gacgagacgt ccttcctcaa gcgcctggag gtcatcgcgg agactggcct cacacaggcc     2220
gaccacctgc ttgagctgta cgagaccaag tggcagcgct cggtggaccc gctgtacaag     2280
gagttcatgt actgagcagg aggagggca gcggcagcag cagcaggagg tggcggcgga     2340
gcaggaggaa gtgtatcggt atgtcggaaa gacgacgtta agtgacttga aagtgatgtt     2400
tgcgagaggc tgatgcctgt gccgtttgat gtgagtgtga gtactgcgcc agtattcgct     2460
gttcgcaacg gcgttaccaa catattgcgg tgggatgcat agttgatcag tttggttgtg     2520
ccaacccaac attctctcgct tgggctgatg catgggcgaa ctgccgaatg cctgggtggc     2580 gctggggtc agcaacatga agcttgttgt gtgtacagcc agaccagctt gaaggaagac     2640
cagcttgaag gaatgagctc ggcctcgagc gttgtgacaa tcgtgctgtc gtgcggacaa     2700
catattatgt tggtgtgccc tccgatgtta tgaacttgct tcgcgtggga tgcgaacgca     2760
ggtacaggta gagacctcaa acggtgacag ggacgggtct ggggcggaaa cctatgggta     2820
tcaggcgatc tgatcaagag gtggatccgc ttgggacata gcacgcgtgc gtcgtacgat     2880
```

```
gaggcaatcg ggcctgtgcc ccggttcctc aggcagtcag gcgccgggtt agtgcggcga    2940
tgaagtacgg tatagtgcct actcagtgca tcgggcggcg gtgcggatat gggcttcacc    3000
cgtgcgttgc gtgaagcttt tggggtcgtg tggcttcgct gtgcggcgtg ccagacgagg    3060
ctccgagatg gtgctgaact ggttgtgaag gtggccggtt cggacttgta aggccctcgc    3120
tcaggaattc                                                           3130
```

```
<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
gctctcgcct caggcgtt                                                    18

<210> SEQ ID NO 6
<211> LENGTH: 29
<212> TYPE: DNA
<213> ORGANISM: Artificial Sequence
<220> FEATURE:
<223> OTHER INFORMATION: Primer

<400> SEQUENCE: 6
ggggaattcc tgagcgaggg ccttacaag                                        29

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
atcagcacac acagcaggct cac                                              23

<210> SEQ ID NO 8
<211> LENGTH: 30
<212> TYPE: DNA
<213> ORGANISM: Artificial Sequence
<220> FEATURE:
<223> OTHER INFORMATION: Primer

<400> SEQUENCE: 8
tgttaaccat tttggcttgt tgtgagtagc                                       30

<210> SEQ ID NO 9
<211> LENGTH: 4245
<212> TYPE: DNA
<213> ORGANISM: Artificial Sequence
<220> FEATURE:
<223> OTHER INFORMATION: pACYC187

<400> SEQUENCE: 9
gaattccgga tgagcattca tcaggcgggc aagaatgtga ataaaggccg gataaaactt      60
gtgcttattt ttctttacgg tctttaaaaa ggccgtaata tccagctgaa cggtctggtt     120
ataggtacat tgagcaactg actgaaatgc ctcaaaatgt tctttacgat gccattggga     180
tatatcaacg gtggtatatc cagtgatttt tttctccatt ttagcttcct tagctcctga     240
aaatctcgat aactcaaaaa atacgcccgg tagtgatctt atttcattat ggtgaaagtt     300
```

```
ggaacctctt acgtgccgat caacgtctca ttttcgccaa aagttggccc agggcttccc    360
ggtatcaaca gggacaccag gatttattta ttctgcgaag tgatcttccg tcacaggtat    420
ttattcggcg caaagtgcgt cgggtgatgc tgccaactta ctgatttagt gtatgatggt    480
gttttttgagg tgctccagtg gcttctgttt ctatcagctg tccctcctgt tcagctactg   540
acggggtggt gcgtaacggc aaaagcaccg ccggacatca gcgctagcgg agtgtatact    600
ggcttactat gttggcactg atgagggtgt cagtgaagtg cttcatgtgg caggagaaaa    660
aaggctgcac cggtgcgtca gcagaatatg tgatacagga tatattccgc ttcctcgctc    720
actgactcgc tacgctcggt cgttcgactg cggcgagcgg aaatggctta cgaacggggc    780
ggagatttcc tggaagatgc caggaagata cttaacaggg aagtgagagg gccgcggcaa    840
agccgttttt ccataggctc cgcccccctg acaagcatca cgaaatctga cgctcaaatc    900
agtggtggcg aaacccgaca ggactataaa gataccaggc gtttccccct ggcggctccc    960
tcgtgcgctc tcctgttcct gcctttcggt ttaccggtgt cattccgctg ttatggccgc   1020
gtttgtctca ttccacgcct gacactcagt tccgggtagg cagttcgctc caagctggac   1080
tgtatgcacg aaccccccgt tcagtccgac cgctgcgcct tatccggtaa ctatcgtctt   1140
gagtccaacc cggaaagaca tgcaaaagca ccactggcag cagccactgg taattgattt   1200
agaggagtta gtcttgaagt catgcgccgg ttaaggctaa actgaaagga caagttttgg   1260
tgactgcgct cctccaagcc agttacctcg gttcaaagag ttggtagctc agagaacctt   1320
cgaaaaaccg ccctgcaagg cggttttttc gttttcagag caagagatta cgcgcagacc   1380
aaaacgatct caagaagatc atcttattaa tcagataaaa tatttctaga tttcagtgca   1440
atttatctct tcaaatgtag cacctgaagt cagccccata cgatataagt tgtaattctc   1500
atgtttgaca gcttatcatc gataagcttt aatgcggtag tttatcacag ttaaattgct   1560
aacgcagtca ggcaccgtgt atgaaatcta acaatgcgct catcgtcatc ctcggcaccg   1620
tcaccctgga tgctgtaggc ataggcttgg ttatgccggt actgccgggc ctcttgcggg   1680
atatcgtcca ttccgacagc atcgccagtc actatggcgt gctgctagcg ctatatgcgt   1740
tgatgcaatt tctatgcgca cccgttctcg gagcactgtc cgaccgcttt ggccgccgcc   1800
cagtcctgct cgcttcgcta cttggagcca ctatcgacta cgcgatcatg gcgaccacac   1860
ccgtcctgtg gatcctctac gccggacgca tcgtggccgg catcaccggc gccacaggtg   1920
cggttgctgg cgcctatatc gccgacatca ccgatgggga agatcgggct cgccacttcg   1980
ggctcatgag cgcttgtttc ggcgtgggta tggtggcagg ccccgtggcc ggggactgt    2040
tgggcgccat ctccttgcat gcaccattcc ttgcggcggc ggtgctcaac ggcctcaacc   2100
tactactggg ctgcttccta atgcaggagt cgcataaggg agagcgtcga ccgatgccct   2160
tgagagcctt caacccagtc agctccttcc ggtgggcgcg gggcatgact atcgtcgccg   2220
cacttatgac tgtcttcttt atcatgcaac tcgtaggaca ggtgccggca gcgctctggg   2280
tcattttcgg cgaggaccgc tttcgctgga gcgcgacgat gatcggcctg tcgcttgcgg   2340
tattcggaat cttgcacgcc ctcgctcaag ccttcgtcac tggtcccgcc accaaacgtt   2400
tcggcgagaa gcaggccatt atcgccggca tggcggccga cgcgctgggc tacgtcttgc   2460
tggcgttcgc gacgcgaggc tggatggcct tccccattat gattcttctc gcttccggcg   2520
gcatcgggat gcccgcgttg caggccatgc tgtccaggca ggtagatgac gaccatcagg   2580
gacagcttca aggatcgctc gcggctctta ccagcctaac ttcgatcact ggaccgctga   2640
tcgtcacggc gatttatgcc gcctcggcga gcacatggaa cgggttggca tggattgtag   2700
```

```
gcgccgccct ataccttgtc tgcctccccg cgttgcgtcg cggtgcatgg agccgggcca   2760
cctcgacctg aatggaagcc ggcggcacct cgctaacgga ttcaccactc caagaattgg   2820
agccaatcaa ttcttgcgga gaactgtgaa tgcgcaaacc aaccctiggc agaacatatc   2880 catcgcgtcc gccatctcca gcagccgcac gcggcgcatc tcgggcagcg ttgggtcctg   2940
gccacgggtg cgcatgatcg tgctcctgtc gttgaggacc cggctaggct ggcggggttg   3000
ccttactggt tagcagaatg aatcaccgat acgcgagcga acgtgaagcg actgctgctg   3060
caaaacgtct gcgacctgag caacaacatg aatggtcttc ggtttccgtg tttcgtaaag   3120
tctggaaacg cggaagtccc ctacgtgctg ctgaagttgc ccgcaacaga gagtggaacc   3180
aaccggtgat accacgatac tatgactgag agtcaacgcc atgagcggcc tcatttctta   3240
ttctgagtta caacagtccg caccgctgtc cggtagctcc ttccggtggg cgcggggcat   3300
gactatcgtc gccgcactta tgactgtctt ctttatcatg caactcgtag acaggtgcc    3360 ggcagcgccc aacagtcccc cggccacggg gcctgccacc atacccacgc cgaaacaagc   3420
gccctgcacc attatgttcc ggatctgcat cgcaggatgc tgctggctac cctgtggaac   3480
acctacatct gtattaacga agcgctaacc gtttttatca ggctctggga ggcagaataa   3540
atgatcatat cgtcaattat tacctccacg gggagagcct gagcaaactg gcctcaggca   3600
tttgagaagc acacggtcac actgcttccg gtagtcaata aaccggtaaa ccagcaatag   3660
acataagcgg ctatttaacg accctgccct gaaccgacga ccgggtcgaa tttgctttcg   3720
aatttctgcc attcatccgc ttattatcac ttattcaggc gtagcaccag gcgtttaagg   3780
gcaccaataa ctgcctttaaa aaaattacgc cccgccctgc cactcatcgc agtactgttg   3840
taattcatta agcattctgc cgacatggaa gccatcacag acggcatgat gaacctgaat   3900
cgccagcggc atcagcacct tgtcgccttg cgtataatat ttgcccatgg tgaaaacggg   3960
ggcgaagaag ttgtccatat tggccacgtt taaatcaaaa ctggtgaaac tcacccaggg   4020
attggctgag acgaaaaaca tattctcaat aaaccctta gggaaatagg ccaggttttc    4080
accgtaacac gccacatctt gcgaatatat gtgtagaaac tgccggaaat cgtcgtggta   4140
ttcactccag agcgatgaaa acgtttcagt ttgctcatgg aaaacggtgt aacaagggtg   4200
aacactatcc catatcacca gctcaccgtc tttcattgcc atacg                   4245
```

<210> SEQ ID NO 10
<211> LENGTH: 1578
<212> TYPE: DNA
<213> ORGANISM: Escherichia coli

<400> SEQUENCE: 10

```
gacaggcggg aggtcaattt gatcccggac gtatcacagg cgctggcctg gctggaaaaa    60
catcctcagg cgttaaaggg gatacagcgt gggctggagc gcgaaacttt gcgtgttaat   120
gctgatggca cactggcaac aacaggtcat cctgaagcat taggttccgc actgacgcac   180
aaatggatta ctaccgattt tgcggaagca ttgctggaat tcattacacc agtggatggt   240
gatattgaac atatgctgac ctttatgcgc gatctgcatc gttatacggc gcgcaatatg   300
ggcgatgagc ggatgtggcc gttaagtatg ccatgctaca tcgcagaagg tcaggacatc   360
gaactggcac agtacggcac ttctaacacc ggacgcttta aaacgctgta tcgtgaaggg   420
ctgaaaaatc gctacggcgc gctgatgcaa accatttccg gcgtgcacta caatttctct   480
ttgccaatgg cattctggca agcgaagtgc ggtgatatct cgggcgctga tgccaaagag   540
```

| aaaatttctg cgggctattt ccgcgttatc cgcaattact atcgtttcgg ttgggtcatt | 600 |
| ccttatctgt ttggtgcatc tccggcgatt tgttcttctt tcctgcaagg aaaaccaacg | 660 |
| tcgctgccgt ttgagaaaac cgagtgcggt atgtattacc tgccgtatgc gacctctctt | 720 |
| cgtttgagcg atctcggcta taccaataaa tcgcaaagca atcttggtat taccttcaac | 780 |
| gatctttacg agtacgtagc gggccttaaa caggcaatca aaacgccatc ggaagagtac | 840 |
| gcgaagattg gtattgagaa agacggtaag aggctgcaaa tcaacagcaa cgtgttgcag | 900 |
| attgaaaacg aactgtacgc gccgattcgt ccaaaacgcg ttacccgcag cggcgagtcg | 960 |
| ccttctgatg cgctgttacg tggcggcatt gaatatattg aagtgcgttc gctggacatc | 1020 |
| aacccgttct cgccgattgg tgtagatgaa cagcaggtgc gattcctcga cctgtttatg | 1080 |
| gtctggtgtg cgctggctga tgcaccggaa atgagcagta gcgaacttgc ctgtacacgc | 1140 |
| gttaactgga accgggtgat cctcgaaggt cgcaaaccgg gtctgacgct gggtatcggc | 1200 |
| tgcgaaaccg cacagttccc gttaccgcag gtgggtaaag atctgttccg cgatctgaaa | 1260 |
| cgcgtcgcgc aaacgctgga tagtattaac ggcggcgaag cgtatcagaa agtgtgtgat | 1320 |
| gaactggttg cctgcttcga taatcccgat ctgactttct ctgcccgtat cttaaggtct | 1380 |
| atgattgata ctggtattgg cggaacaggc aaagcatttg cagaagccta ccgtaatctg | 1440 |
| ctgcgtgaag agccgctgga aattctgcgc gaagaggatt ttgtagccga gcgcgaggcg | 1500 |
| tctgaacgcc gtcagcagga aatggaagcc gctgataccg aaccgtttgc ggtgtggctg | 1560 |
| gaaaaacacg cctgacag | 1578 |

<210> SEQ ID NO 11
<211> LENGTH: 3397
<212> TYPE: DNA
<213> ORGANISM: Synechococcus sp. PCC7002

<400> SEQUENCE: 11

| cggatcaaga tgctgcctaa acacgagaaa accccccaaaa gtttggcgac cggcggggggc | 60 |
| ttctctaaac caaataaaag caaacaggga cggcaaaacc gagccctaat tgatcatgat | 120 |
| cgtcaaggcg aaggaggcct taactcactg tgatcgtatc agataatttt acatctagca | 180 |
| gtaataccgg ggcagattta gcgagtagcg tcagtgagaa ccgttctcat tttatcgcag | 240 |
| aatctcacta tagggaatgg gtagagggtt ccggggtcgc ccctgagatt gcccggttaa | 300 |
| atgttagatc gttgtcaggg atgacgccct atgaatacct gctctacagt gatgagccag | 360 |
| cattacgccg caatgatggc aggcttcggg atacttggct taagcgatat gcctttgtcg | 420 |
| agcatggcgg ttggtggtgc tcaggcatcg atattaagac cgggaaagat tctctttggg | 480 |
| gttgcttcaa aggcgatcgc ccccgtaaag atcgcgaaga taagaaaccg atcaagtatg | 540 |
| agcacccgcc acgggtagcc accgaaattt tcactctcaa ggtagaccgg ggcacctggc | 600 |
| gcaagattgc caagcgccac aaagtcgagc taccagaaac cgatcaaggc ttctgggaat | 660 |
| gggtactagc ccatcctgag ctaccgatca tcatcactga gggcgcgaag aaggcagggg | 720 |
| ccctcctaac cgctggttat tgcgccatcg gtctaccggg gatttacaac ggctacagaa | 780 |
| cgccaaaaaa tgaccatggc gagccaatgc gacagctacg gcacctcatt ccagagcttg | 840 |
| acctgttggc gaaaaataac cgggcgatcg ccttctgttt tgaccaagac aagaaaccca | 900 |
| agacgatcaa ggcagtgaac ggggcgatcc aaactaccgg ggcactccta gagaaggccg | 960 |
| gggcgaaagt atcggtgatc acctggcacc aggacgcgaa aggtgttgat gatctgatcg | 1020 |
| tcgagcacgg agcgaaagca ctccataacc gctacaagca ccgcaagccc ttagcagtct | 1080 |

```
gggagatgga taatctcacc gatatcacca cgcaagtcga tctaacggtc gatcagcgct   1140
atctcgacat cgatccgcgt gctatcccca aggatgctca gattattttc attaaatctg   1200
ccaagggcac cgggaaaaca gaatggttag ggaaaatcgt taagctcgcc caagatgatt   1260
gcgctcgcgt actggttttg actcaccgca tccaattagc caaggagctc gcccgccgtc   1320
tcgatatcga tcacattagc gagctcgaca gtagcccgac cggggcgct ctagggatgg    1380
cgatgtgtat cgatagccta catcccgata gccaagctca ttttaatttc atggaatggc   1440
acggcgctca cattgtccta gacgaaatcg agcaagtttt agggcacgct ttgggtagct   1500
cgacctgtac ccaagaccgg gcgaaaatcc ttgaaacgtt ctacaaccta atcctttatg   1560
ccctaaggac aggcggaaaa ctctactgct ctgatgctga tttatctccc atctcctatg   1620
agctaatcaa gtacattctt gacggttgtg agttcaaacc attcaccatt ctgaatacct   1680
ataagccctg tttagagcaa caaagagacc tgttttttcta tgaagggaat gaccctagag  1740
acctgttaac caatctcaga caagcgattg agaacggtga gaaaacactt gtctttaccg   1800
ctgcccaaaa gaccgcatcg acctacagca cgcagaactt agaatcactc tttagggaga   1860
aatatcccga taagagaatc ttgagaatcg atgctgaatc ggtcgctgaa ccggggcacc    1920
ctgcctatgg ttgtattgac tcgctgaatg caattttgcc cctgtacgat attgtgctct   1980
gctcgcccgc tgtcgagacc ggggtgagta tcgatatcaa ggatcatttt gattctgttt   2040
ggggcatggg ttcagggggtt cagaccgtta acggtttctg ccaagggcta gagcggttac  2100
gggataacgt ccctcgccat gtttggatac cgaaattttc cccacactcg aaccggatcg   2160
ccaatggggg ctacaccgct aaggcgatcg cccgtgacca gcaccgctat gcagagctca   2220
cccacaaatt aatcggtgag cacgccgctg aatgcagtgg gttagaagat tctttaaaac   2280
cattcctttg ggcctattgt cgctatgcgg cgcttgctaa ccgtggcttt ggcagttacc   2340
gggaagcgat tttaaataag ctgctttctg agggctatgt acagaaagat ttgagcgaaa   2400
tcgatccagc attggctaag gattatcgag acgaattaaa agcggtgaaa gaccataatt   2460
atctacagga aagggttgcg atttctaaag tagaaaatcc tgacgatcgc cagtacgaaa   2520
aactgaagcg tcagcgggcg aaatctgaga cggaacggca ccaagaacgc cacgggaaac   2580
tttctcgctc ctatgggtta actgtgaccc ctgagcttgt cgagaaagat gatgatgggt   2640
ggtactctca gctccagctc gaatactact taaccgttgg gaaagcattc tgctctgccc   2700
gcgaccgggc gaaatatgac cagctccaac atgagggctt tgtatttaag ccggatatca   2760
acaggcgatc gctctcacca aagattcacc tgttagagct actcaacatc catcagttct   2820
taaaaccagg ggtgacattc accggggcga gccttgaagg gttcaaggaa aattgtttgc   2880
ggtatgccaa gccgatcaag tggattcttg gcagaacgat caccgacaaa atgagcccgc   2940
tcgaaattgc tcaggcgctc ctaggcaagc ttgaccggaa attggaatac aagggggcgct  3000
ttggatcgcg ggataaccgt cagcgggtct atgaggcgat cgcccctaac gatcagcgcg   3060
aaaaggtctt tgctcattgg ttacagcgtg accaagcaaa attaggggcc gtgtccaacc   3120
cctgtataaa tagatttatt caggaggctt agacccgtga tcgaaatact cgttgtgcag   3180
ctctcccttg gcaatcccaa acaatctcaa gatttgctct gcggtatcgg gacgttttat   3240
gcccttgcgg aaagcgcctt tgctcttctg gtagccccta gactgtgcca gatcataagc   3300
ctcactgagg gtgagggcac taccgggggc atgagctcgc ccaagagatt cagcgaccgg   3360
ggcgatcgcc cttggtaatt ctctcaggcg ctcaact                            3397
```

<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12
gggatgcatg acaggcggga ggtcaatttg                                30

<210> SEQ ID NO 13
<211> LENGTH: 30
<212> TYPE: DNA
<213> ORGANISM: Artificial Sequence
<220> FEATURE:
<223> OTHER INFORMATION: Primer

<400> SEQUENCE: 13
gggctcgagc tgtcaggcgt gttttttccag                                30

<210> SEQ ID NO 14
<211> LENGTH: 40
<212> TYPE: DNA
<213> ORGANISM: Artificial Sequence
<220> FEATURE:
<223> OTHER INFORMATION: Primer

<400> SEQUENCE: 14
cccgtcgaca aagcatgccg gatcaagatg ctgcctaaac                      40

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
agttgagcgc ctgagagaat tacc                                       24

<210> SEQ ID NO 16
<211> LENGTH: 23
<212> TYPE: DNA
<213> ORGANISM: Artificial Sequence
<220> FEATURE:
<223> OTHER INFORMATION: Primer

<400> SEQUENCE: 16
cagcatcacc cgacgcactt tgc                                        23

<210> SEQ ID NO 17
<211> LENGTH: 26
<212> TYPE: DNA
<213> ORGANISM: Artificial Sequence
<220> FEATURE:
<223> OTHER INFORMATION: Primer

<400> SEQUENCE: 17
cctaatgcag gagtcgcata agggag                                     26

<210> SEQ ID NO 18
<211> LENGTH: 23
<212> TYPE: DNA
<213> ORGANISM: Artificial Sequence
<220> FEATURE:
<223> OTHER INFORMATION: Primer

```
<400> SEQUENCE: 18
gcacacggtc acactgcttc cgg                                          23
```

ALGA IN WHICH PRODUCTION OF PHOTOSYNTHETIC PRODUCTS IS IMPROVED, AND USE FOR SAID ALGA

CROSS-REFERENCE TO RELATED APPLICATIONS

This application is the U.S. national phase, pursuant to 35 U.S.C. §371, of PCT international application Ser. No. PCT/JP2011/069501, filed Aug. 29, 2011, designating the United States and published in Japanese on Mar. 8, 2012 as publication W02012/029727. PCT/JP2011/069501 claims priority to Japanese Patent Application Ser. No. 2010-194210, filed Aug. 31, 2010. The entire contents of the aforementioned patent applications are incorporated herein by reference.

SEQUENCE LISTING

The instant application contains a Sequence Listing which has been submitted in ASCII format via EFS-Web and is hereby incorporated by reference in its entirety. Said ASCII copy, created on Feb. 14, 2013, is named 92343_70904_Sequence_Listing_ST25.txt and is 28,357 bytes in size.

TECHNICAL FIELD

The present invention relates to (i) an alga in which productivity of a photosynthate is increased and (ii) use of the alga. Specifically, the present invention relates to (i) an alga in which productivity of a photosynthate is increased, (ii) a method for producing the alga, and (iii) a method for producing biomass with the use of the alga.

BACKGROUND ART

Biomass-derived fuels, i.e., so-called biofuels (e.g., bioethanol, biodiesel etc.) are expected as alternatives to fossil fuels.

Biomass is a raw material for a biofuel, and encompasses oils and fats, saccharides (including starch), or the like. Biomass is produced as a result of photosynthesis of plants. Accordingly, plants that are capable of vigorously photosynthesizing and accumulating oils and fats, or saccharides in their cells can be used as means for producing biomass. Currently, corn and soybean are mainly used for production of biomass. However, corn and soybean are also consumed as food and feed. In consequence, price increment for food and feed due to rapid increase in biofuel production is becoming problems.

In view of the circumstance, biomass production using an alga is attracting attention as biomass production means alternative to corn and soybean (see, for example, Patent Literature 1 and Patent Literature 2). Biomass production using an alga has, for example, advantages of not conflicting with food and feed production and enabling mass propagation.

For example, mutants of *Chlamydomonas*, which is a kind of alga, such as a cell-wall-deficient mutant and a mutant with a thin cell wall (e.g., cw15, cw92) are known. Such mutants have properties convenient for introduction of DNA into cells from an outside, and are therefore widely used in gene introduction experiments. Further, since cells of such mutants are easy to break, contents in the cells are easy to collect. This leads to increased productivity of biomass. In view of these advantages, studies on biomass production using such mutants are reported. For example, Patent Literature 3 describes a technique of producing oils and fats by using a cell-wall-deficient *Chlamydomonas* mutant. Non-Patent Literature 1 reports that a *Chlamydomonas* which suffers from a starch synthesis gene deficiency in addition to the cell wall mutation (cw15) releases oil droplets made of oils and fats out of its cells. Non-Patent Literature 2 reports that productivity of oils and fats is increased by breaking a starch synthesis gene of the cell wall mutant (cw15) of *Chlamydomonas*. Non-Patent Literature 3 is known as a report about mutation of *Chlamydomonas* cell walls.

Further, Patent Literature 4 reports a technique of (i) producing starch with the use of chlorella, which is a kind of alga, (ii) releasing the starch out of cells, and (iii) then carrying out ethanol fermentation with the starch.

CITATION LIST

Patent Literature 1

Japanese Patent Application Publication, Tokukaihei, No. 11-196885 A (Publication Date: Jul. 27, 1999)

Patent Literature 2

Japanese Patent Application Publication, Tokukai, No. 2003-310288 A (Publication Date: Nov. 5, 2003)

Patent Literature 3

WO 2009/153439 (Publication Date: Dec. 23, 2009)

Patent Literature 4

Japanese Patent Application Publication, Tokukai, No. 2010-88334 A (Publication Date: Apr. 22, 2010)

Non-Patent Literature 1

Zi Teng Wang, Nico Ullrich, Sunjoo Joo, Sabine Waffenschmidt, and Ursula Goodenough (2009) Eukaryotic Cell Vol. 8 (12): 1856-1868. Algal Lipid Bodies: Stress Induction, Purification, and Biochemical Characterization in Wild-Type and Starchless *Chlamydomonas reinhardtii*.

Non-Patent Literature 2

Yantao Li, Danxiang Han, Guongrong Hu, David Dauvillee, Milton Sommerfeld, Steven Ball and Qiang Hu (2010) Metabolic Engineering Vol. 12 (4): 387-391. *Chlamydomonas* starchless mutant defective in ADP-glucose pyrophosphorylase hyper-accumulates triacylglycerol.

Non-Patent Literature 3

Hyams, J., Davies, D. R. (1972) Mutation Research 14 (4): 381-389. The induction and characterisation of cell wall mutants of *Chlamydomonas reinhardi*.

SUMMARY OF INVENTION

Technical Problem

However, the above biomass production techniques using an alga have a problem in terms of productivity. For example, in a case where biomass is produced by cultivating an alga under a heterotrophic condition with the use of a carbon source such as acetic acid, a nutrient restriction step such as a step of creating a nitrogen-starved state is required for inducing the alga to produce and accumulate biomass. In general, an alga is grown in a culture solution containing nitrogen, and therefore, in order to create a nitrogen-starved state, the culture solution containing nitrogen needs to be replaced with a nitrogen-free culture solution. This undesirably complicates a biomass production procedure and causes a decline in productivity and an increase in cost.

The present invention was accomplished in view of the above conventional problems, and an object of the present invention is to provide (i) an alga that can be increased in productivity of biomass without the need for a nutrient restriction step and (ii) use thereof.

Solution to Problem

As a result of various studies mainly aiming for solution of the above problems, the inventors of the present invention found that artificially increasing glutathione concentration in a chloroplast of an alga can increase productivity of biomass in a cell of the alga without the need for a nutrient restriction step such as a step of creating a nitrogen-starved state. Based on this finding, the inventors of the present invention accomplished the present invention.

That is, an alga of the present invention has an increased glutathione concentration in its chloroplast.

A method of the present invention for producing an alga is a method for producing the aforementioned alga which method includes the step of increasing a glutathione concentration in a chloroplast of the alga.

A method of the present invention for producing biomass is a method for producing biomass with the use of the alga of the present invention or an alga produced by the method of the present invention for producing an alga.

A method of the present invention for producing biomass includes the step of cultivating an alga in the presence of a substance for increasing a glutathione concentration in a chloroplast of the alga.

Advantageous Effects of Invention

The alga of the present invention has an increased glutathione concentration in a chloroplast of the alga. This allows an increase in productivity of a photosynthate in a cell of the alga without the need to create a nitrogen-starved state. Accordingly, use of the alga of the present invention makes it unnecessary to make exchange for a nitrogen-free culture solution for inducing accumulation of a photosynthate. That is, according to the present invention, it is possible to easily and efficiently induce accumulation of a photosynthate. As a consequence, according to the method of the present invention for producing biomass, it is possible to produce biomass from an alga more efficiently at lower cost as compared with a conventional art.

Additional objects, advantages and novel features of the invention will be set forth in part in the description which follows, and in part will become apparent to those skilled in the art upon examination of the following or may be learned by practice of the invention.

Figure 5:
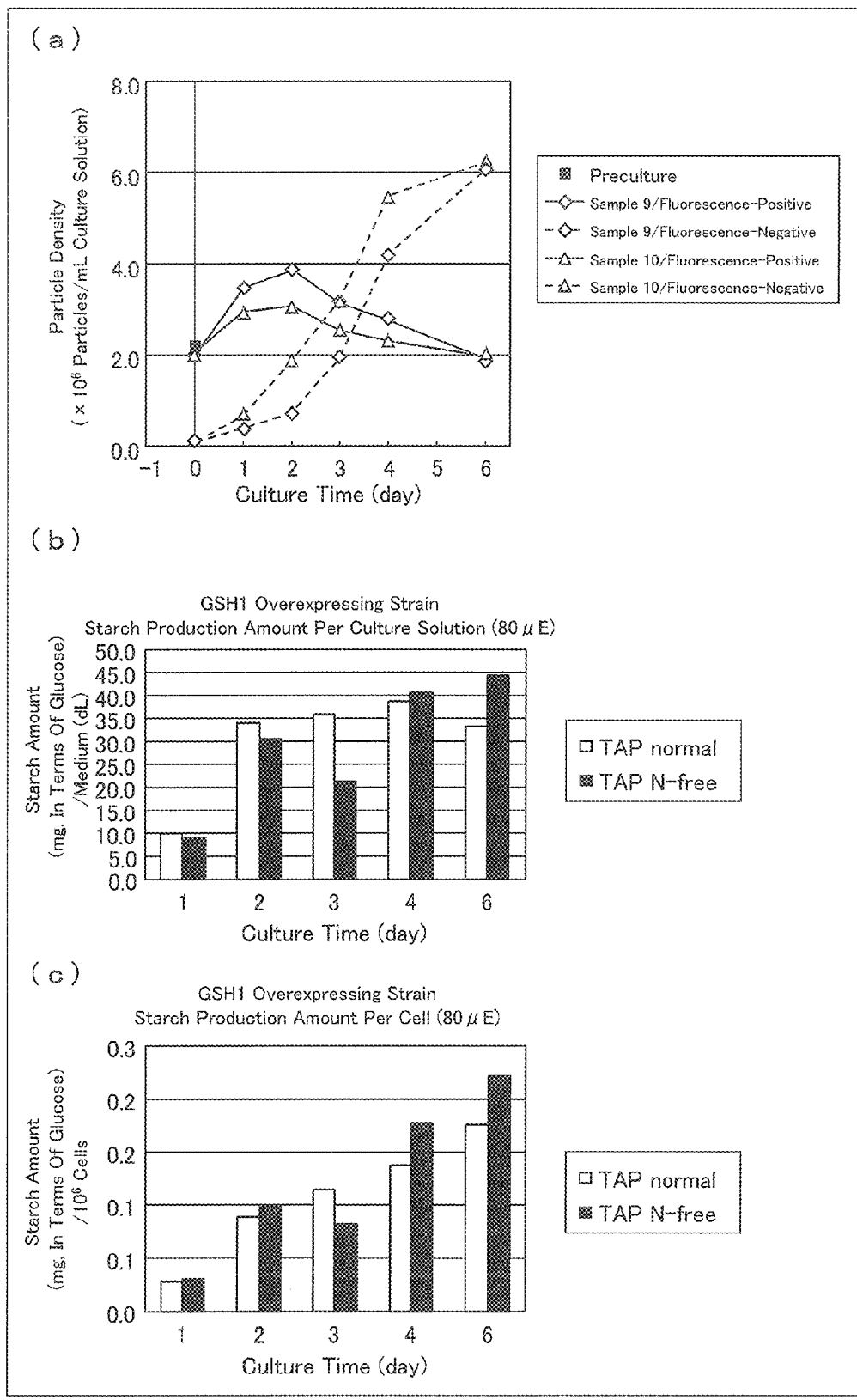

(a) of FIG. 5 is a graph showing (i) a time-course for density of particles (i.e., cells) that exhibit chlorophyll fluorescence and (ii) a time-course for density of particles (i.e., starch grains) that do not exhibit chlorophyll fluorescence in Samples 9 and 10, (b) of FIG. 5 is a graph showing a time-course for a starch amount per culture solution in Samples 9 and 10, and (c) of FIG. 5 is a graph showing a time-course for a starch amount per cells in Samples 9 and 10. In (b) and (c) of FIG. 5, "TAP normal" and "TAP N-free" in the legend represent "TAP medium containing a nitrogen source" and "TAP medium containing no nitrogen source", respectively.

Figure 6:
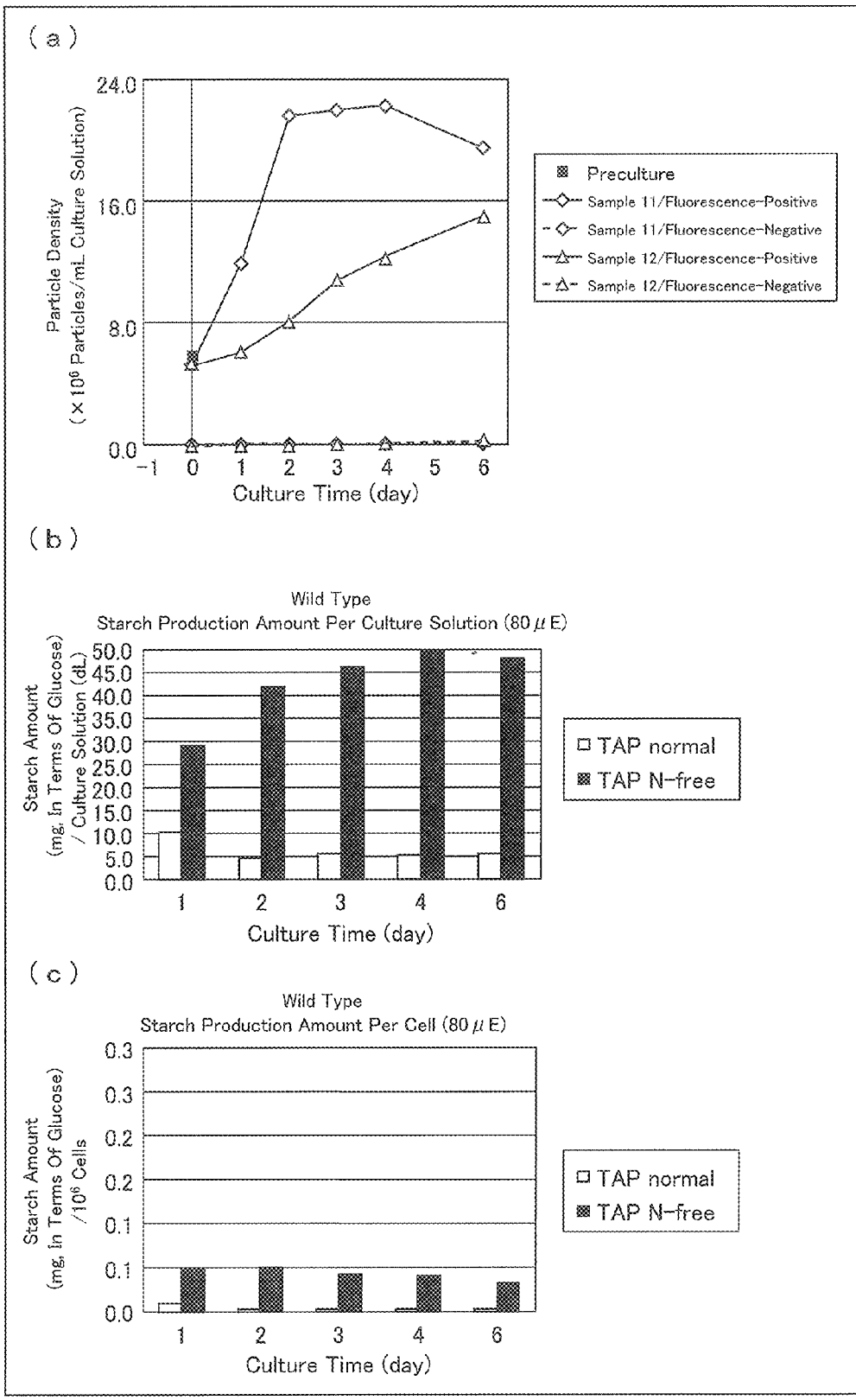

(a) of FIG. 6 is a graph showing (i) a time-course for density of particles (i.e., cells) that exhibit chlorophyll fluorescence and (ii) a time-course for density of particles (i.e., starch grains) that do not exhibit chlorophyll fluorescence in Samples 11 and 12, (b) of FIG. 6 is a graph showing a time-course of a starch amount per culture solution in Samples 11 and 12, and (c) of FIG. 6 is a graph showing a time-course for a starch amount per cells in Samples 11 and 12. In (b) and (c) of FIG. 6, "TAP normal" and "TAP N-free" in the legend represent "TAP medium containing a nitrogen source" and "TAP medium containing no nitrogen source", respectively.

Figure 7:
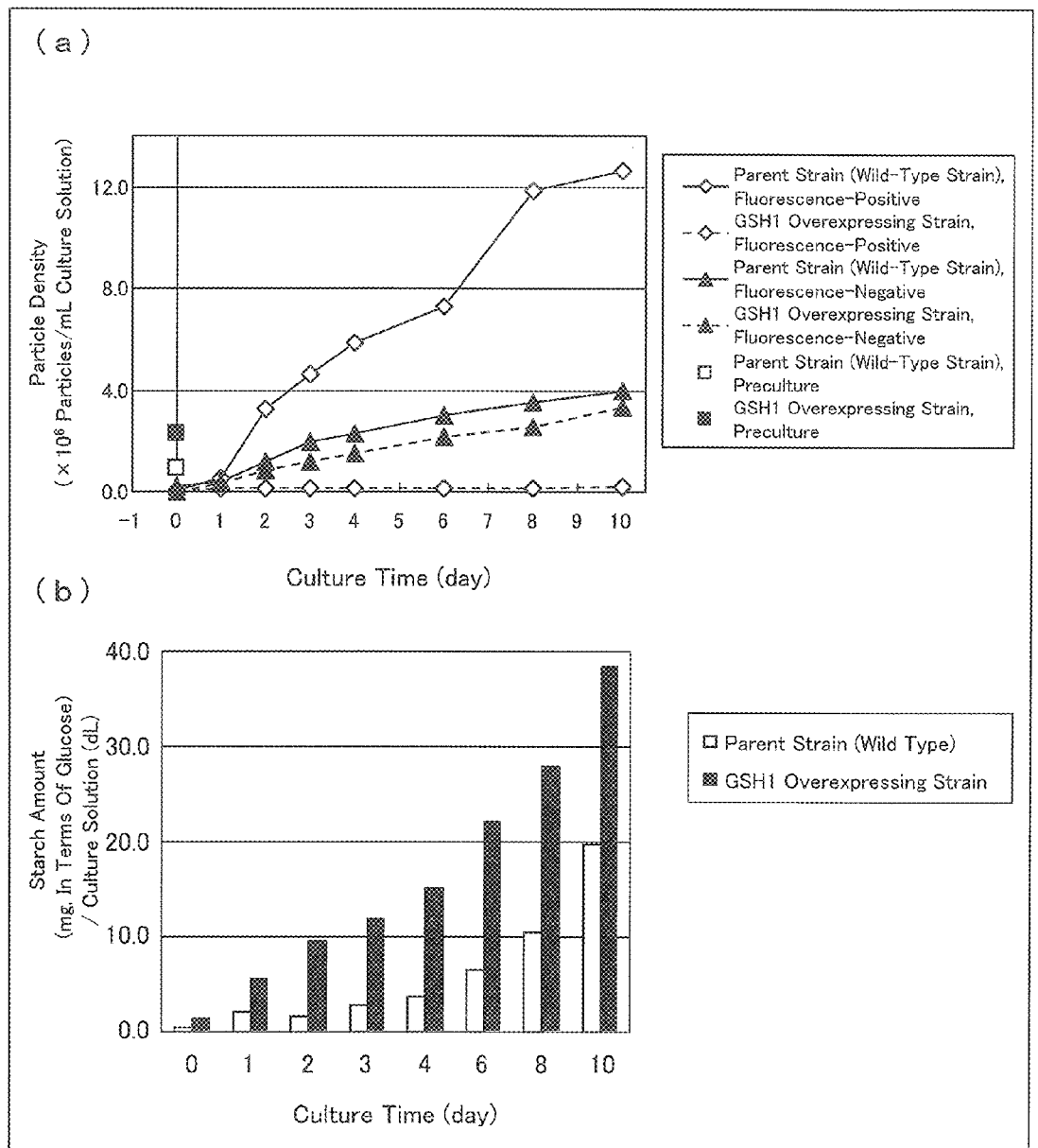

(a) of FIG. 7 is a graph showing (i) a time-course for density of particles that exhibit chlorophyll fluorescence and (ii) a time-course for density of particles that do not exhibit chlorophyll fluorescence in the GSH1 overexpressing strain and the parent strain (wild-type strain), and (b) of FIG. 7 is a graph showing a time-course for a starch amount per culture solution.

Figure 8:
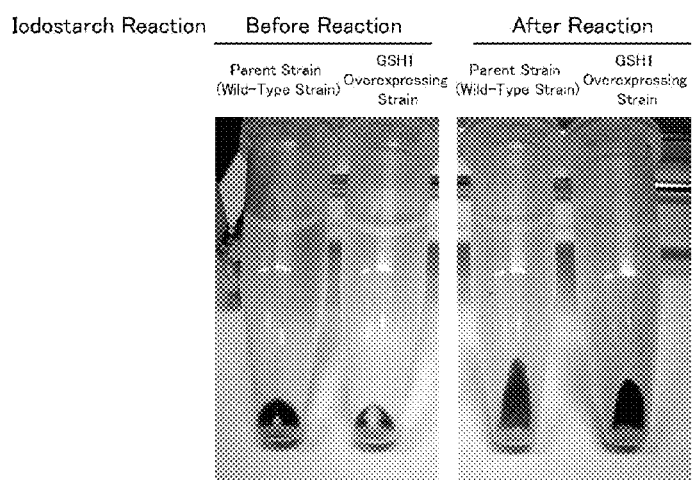

FIG. 8 is a view showing results of iodostarch reaction in the GSH1 overexpressing strain and the parent strain (wild-type strain).

Figure 9:
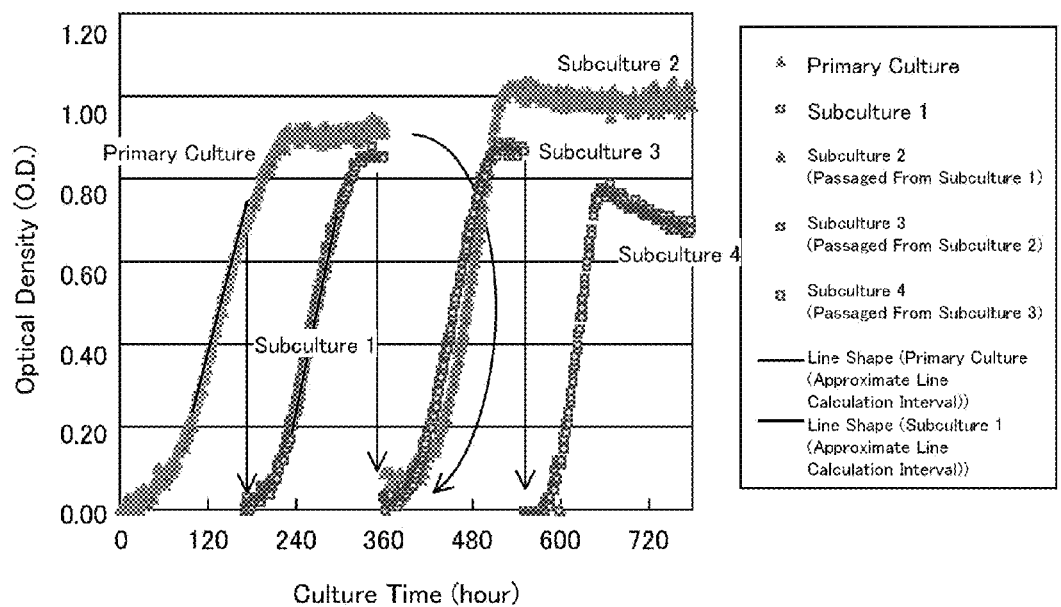

FIG. 9 is a view showing a result of analysis of a growth capacity of the GSH1 overexpressing strain.

Figure 10:
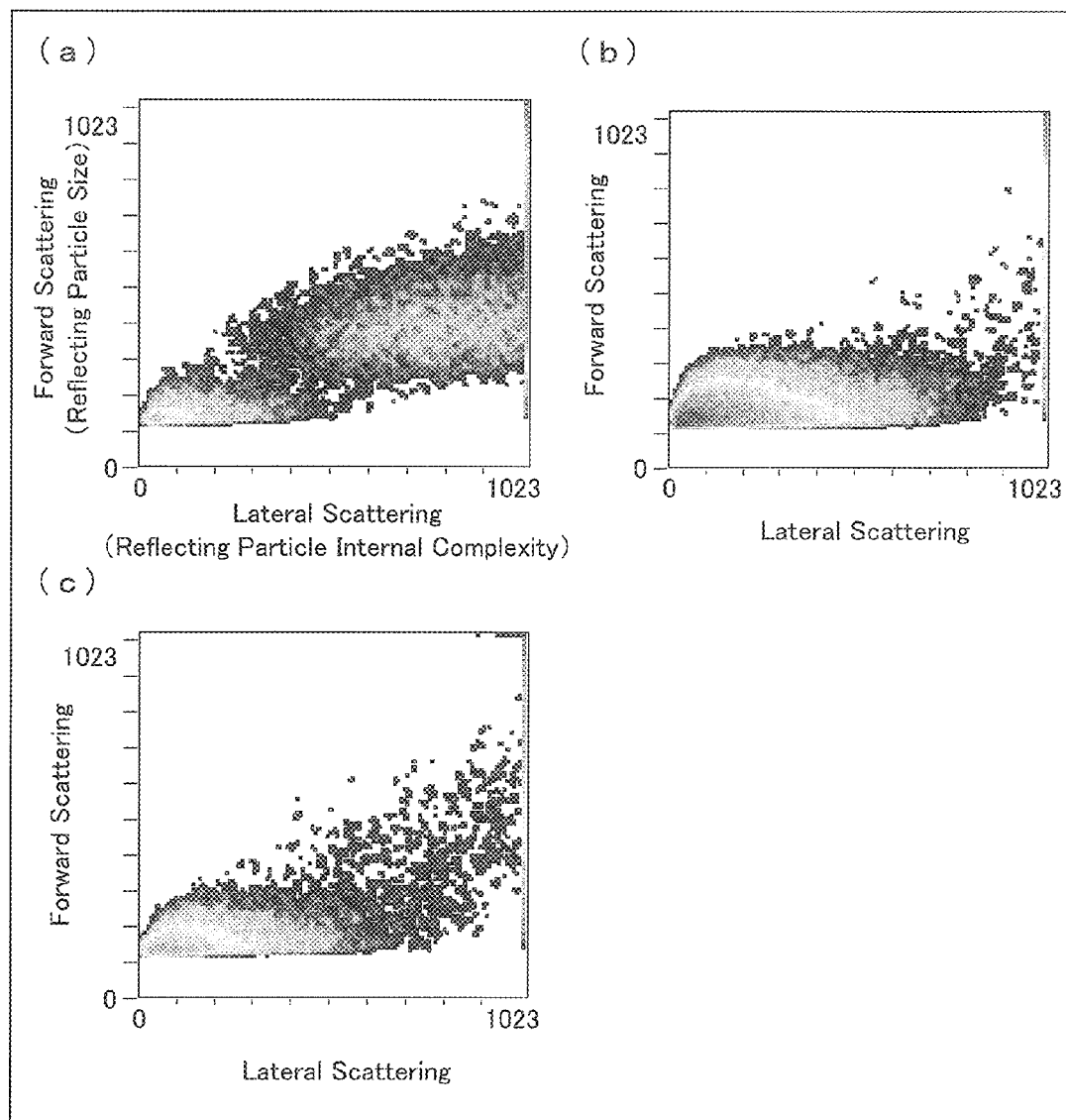

FIG. 10 shows a result of analysis of states of the GSH1 overexpressing strain at respective passaging points, (a) of FIG. 10 is a view showing a correlation between cell size and cell internal complexity in the GSH1 overexpressing strain during the "SUBCULTURE 1" shown in FIG. 9, (b) of FIG. 10 is a view showing a correlation between cell size and cell internal complexity in the GSH1 overexpressing strain during the "SUBCULTURE 2" shown in FIG. 9, and (c) of FIG. 10 is a view showing a correlation between cell size and cell internal complexity in the GSH1 overexpressing strain during the "SUBCULTURE 3" shown in FIG. 9.

Figure 11:
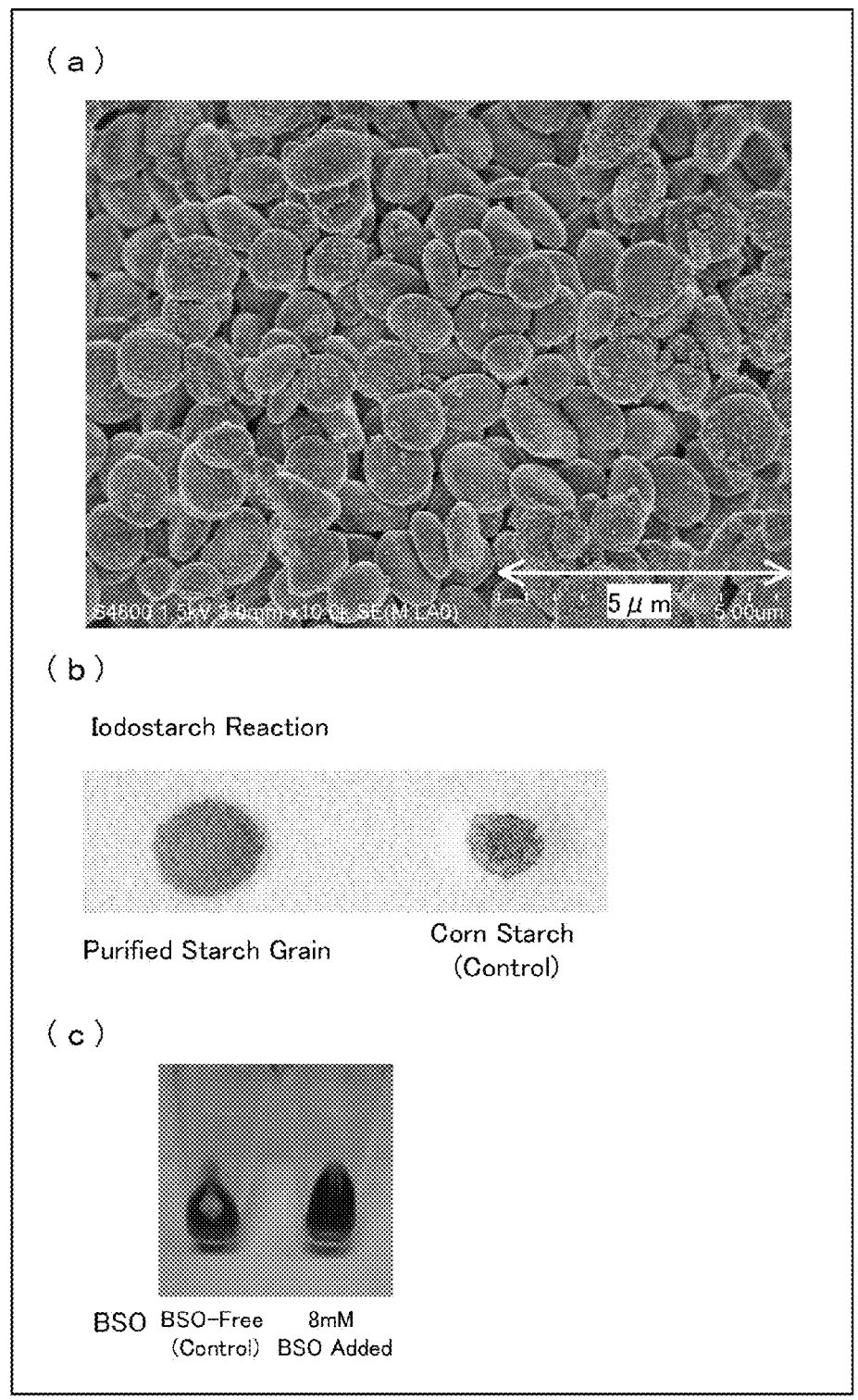

FIG. 11 is a view showing a result of observation of a shape of a starch grain discharged to an outside of the cells from the GSH1 overexpressing strain, (a) of FIG. 11 is a view showing a result of observation of starch grains with the use of a scanning electron microscope, (b) of FIG. 11 is a view showing a result of iodostarch reaction of a starch grain discharged from the GSH1 overexpressing strain, and (c) of FIG. 11 is a view showing a starch production capacity of the GSH1 overexpressing strain in a case where BSO, which is an inhibitor for GSH synthesis, was added so that a final concentration becomes 8 mM.

Figure 12:
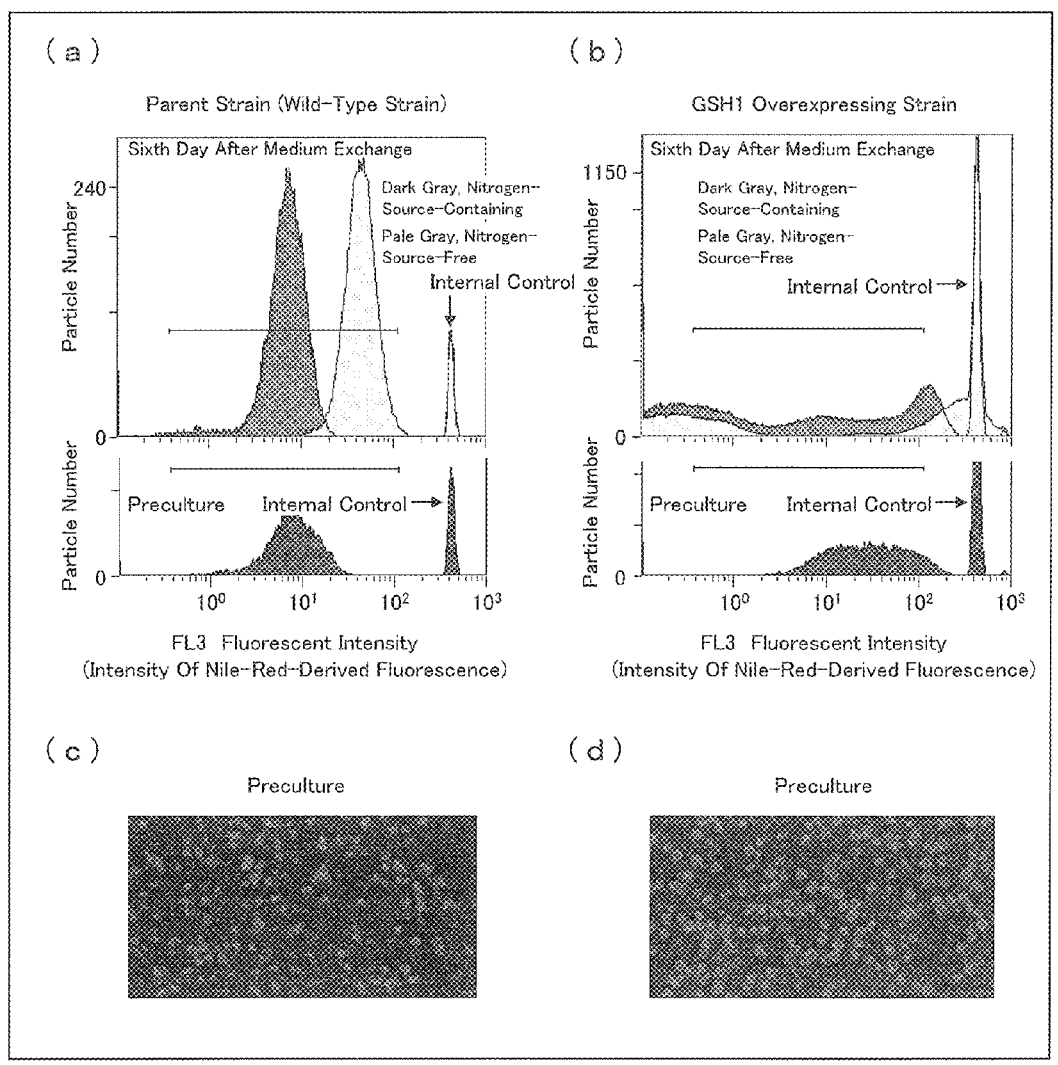

FIG. 12 shows a result of analysis of an oils and fats production capacity of the GSH1 overexpressing strain, (a) of FIG. 12 is a histogram for cells that exhibit nile-red-derived fluorescence in the parent strain (wild-type strain), (b) of FIG. 12 is a histogram for cells that exhibit nile-red-derived fluorescence in the GSH1 overexpressing strain, (c) of FIG. 12 is a view showing a result of observation of the nile-red stained parent strain (wild-type strain) with the use of a confocal laser microscope, and (d) of FIG. 12 is a view showing a result of observation of the nile-red stained GSH1 overexpressing strain with the use of a confocal laser microscope.

Figure 13:
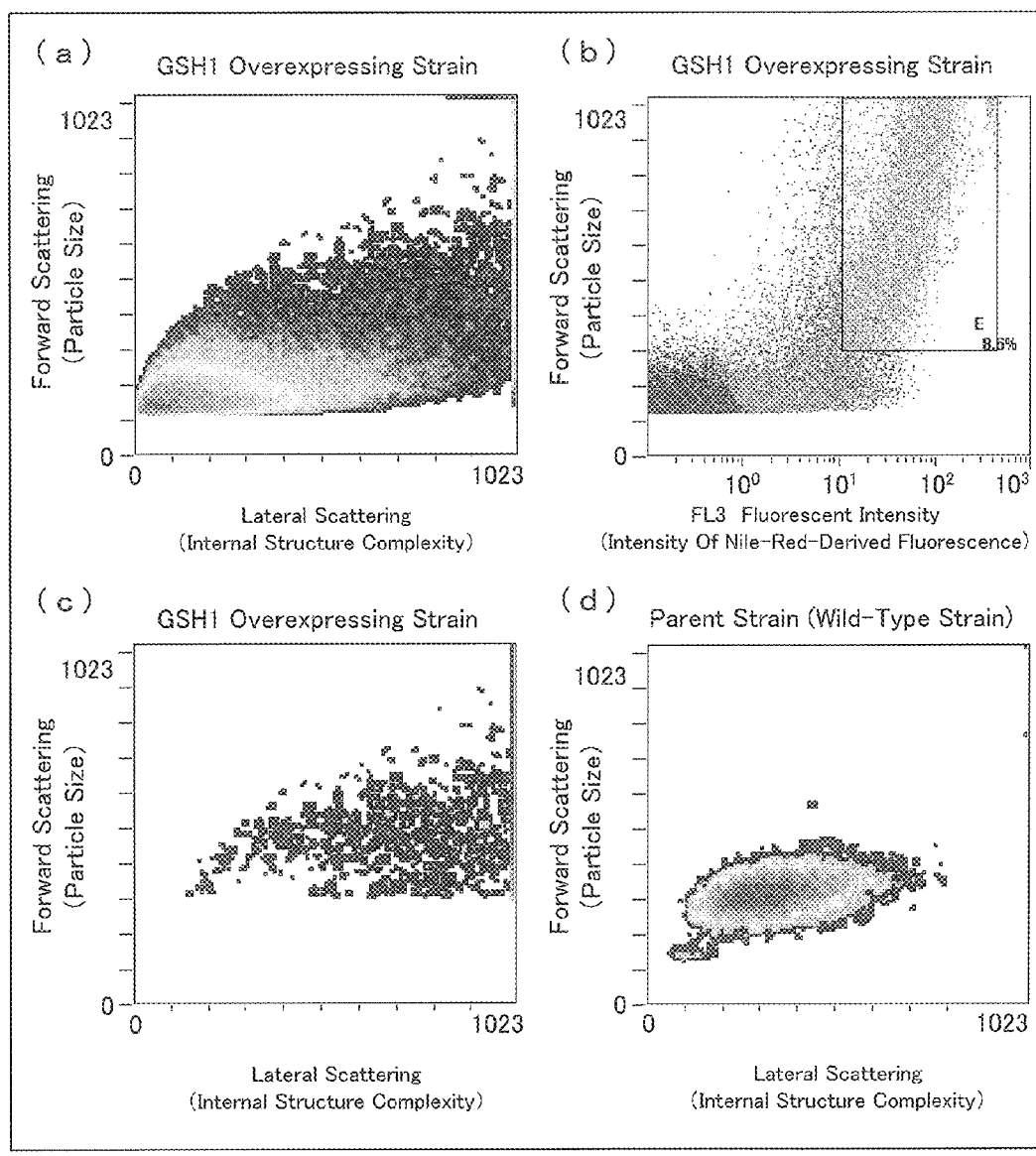

FIG. 13 shows a result of analysis of a state of the GSH1 overexpressing strain, (a) of FIG. 13 is a view showing a correlation between cell size and cell internal complexity in the GSH1 overexpressing strain, (b) of FIG. 13 is a view showing a correlation between cell size and fluorescent intensity of the nile-red-derived fluorescence in the GSH1 overexpressing strain, (c) of FIG. 13 is a view showing a correlation between cell size and cell internal complexity as to cells contained in the rectangular region in (b) of FIG. 13, and (d) of FIG. 13 is a view showing a correlation between cell size and cell internal complexity in the parent strain (wild-type strain).

Figure 14:
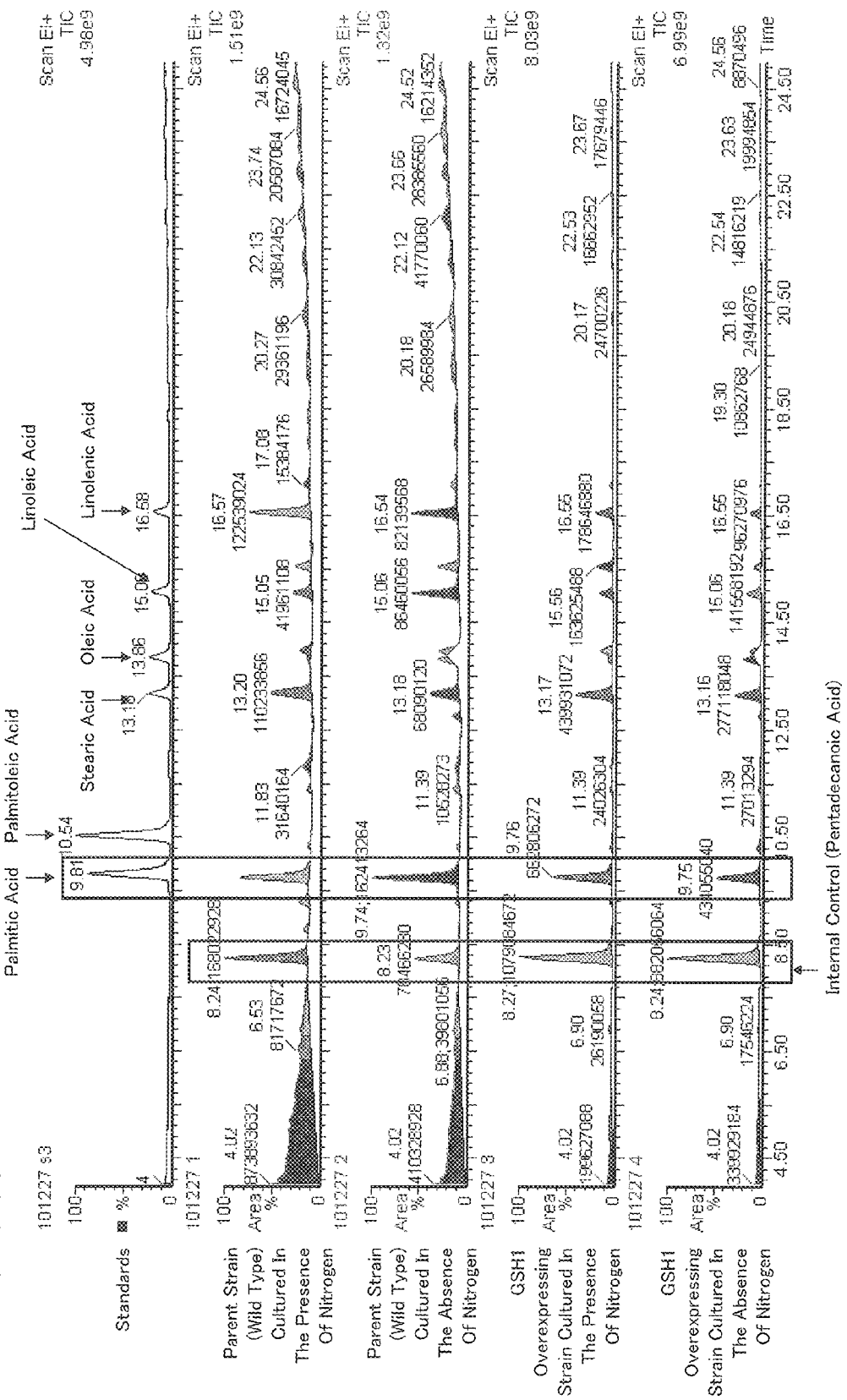

FIG. 14 is a view showing a result of gas chromatograph mass spectrometry.

Figure 15:
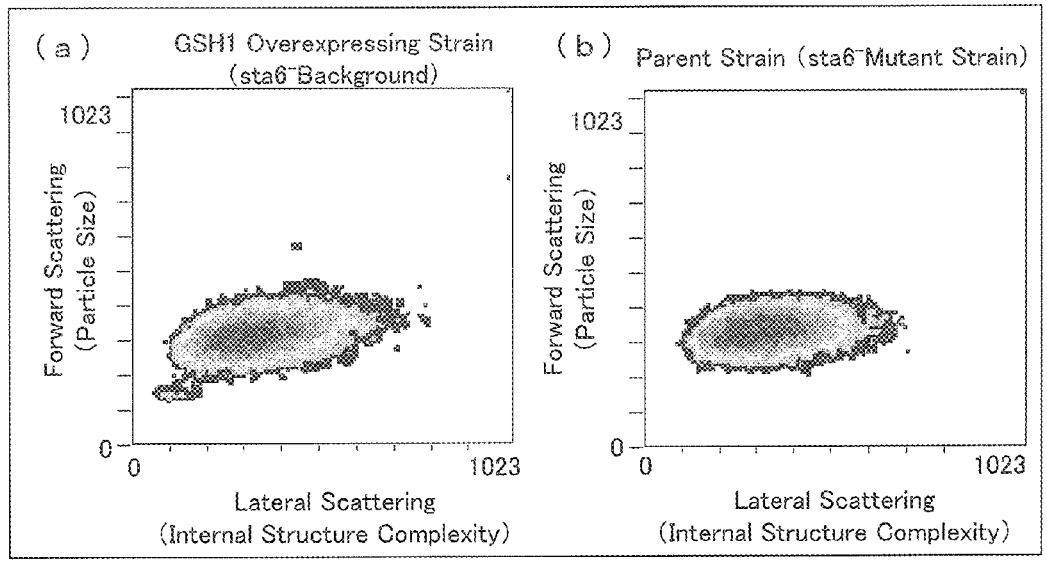

FIG. 15 shows a result of analysis of a state of the GSH1 overexpressing strain (sta6− background) and a state of the parent strain (sta6−), (a) of FIG. 15 is a view showing a correlation between cell size and cell internal complexity in the parent strain (sta6−), and (b) of FIG. 15 is a view showing a correlation between cell size and cell internal complexity in the GSH1 overexpressing strain (sta6− background).

Figure 16:
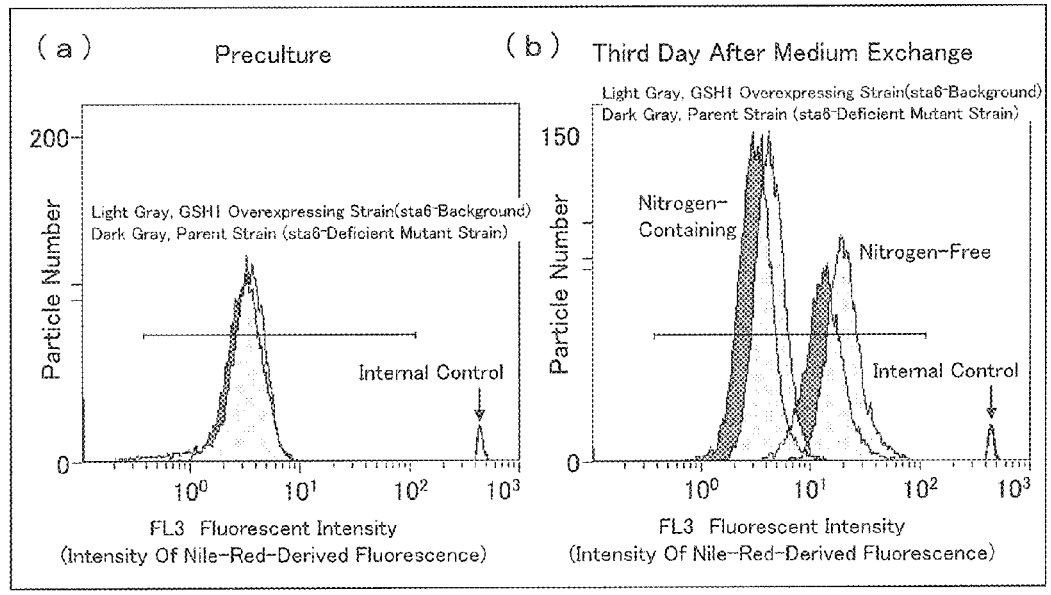

FIG. 16 shows a result of analysis of (i) oils and fats production capacities of the GSH1 overexpressing strain (sta6− background) and the parent strain (sta6−) at the end of the preculturing and (ii) oils and fats production capacities of the GSH1 overexpressing strain (sta6− background) and the parent strain (sta6−) on the third day after the medium change, (a) of FIG. 16 is a histogram for cells exhibiting nile-red-derived fluorescence in the GSH1 overexpressing strain (sta6− background) and the parent strain (sta6−) at the end of the preculturing, and (b) of FIG. 16 is a histogram for cells exhibiting nile-red-derived fluorescence in the GSH1 overexpressing strain (sta6− background) and the parent strain (sta6−) on the third day after the medium change.

Figure 17:
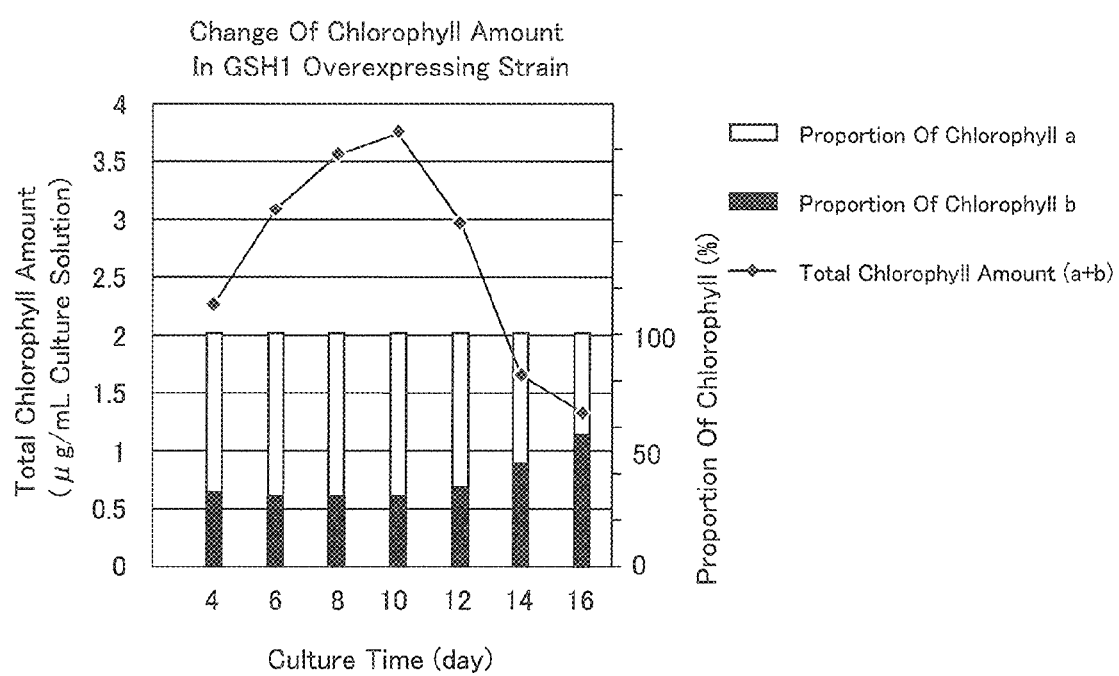

FIG. 17 shows a result of analysis of a chlorophyll amount in the GSH1 overexpressing strain produced in Example 1.

Figure 18:
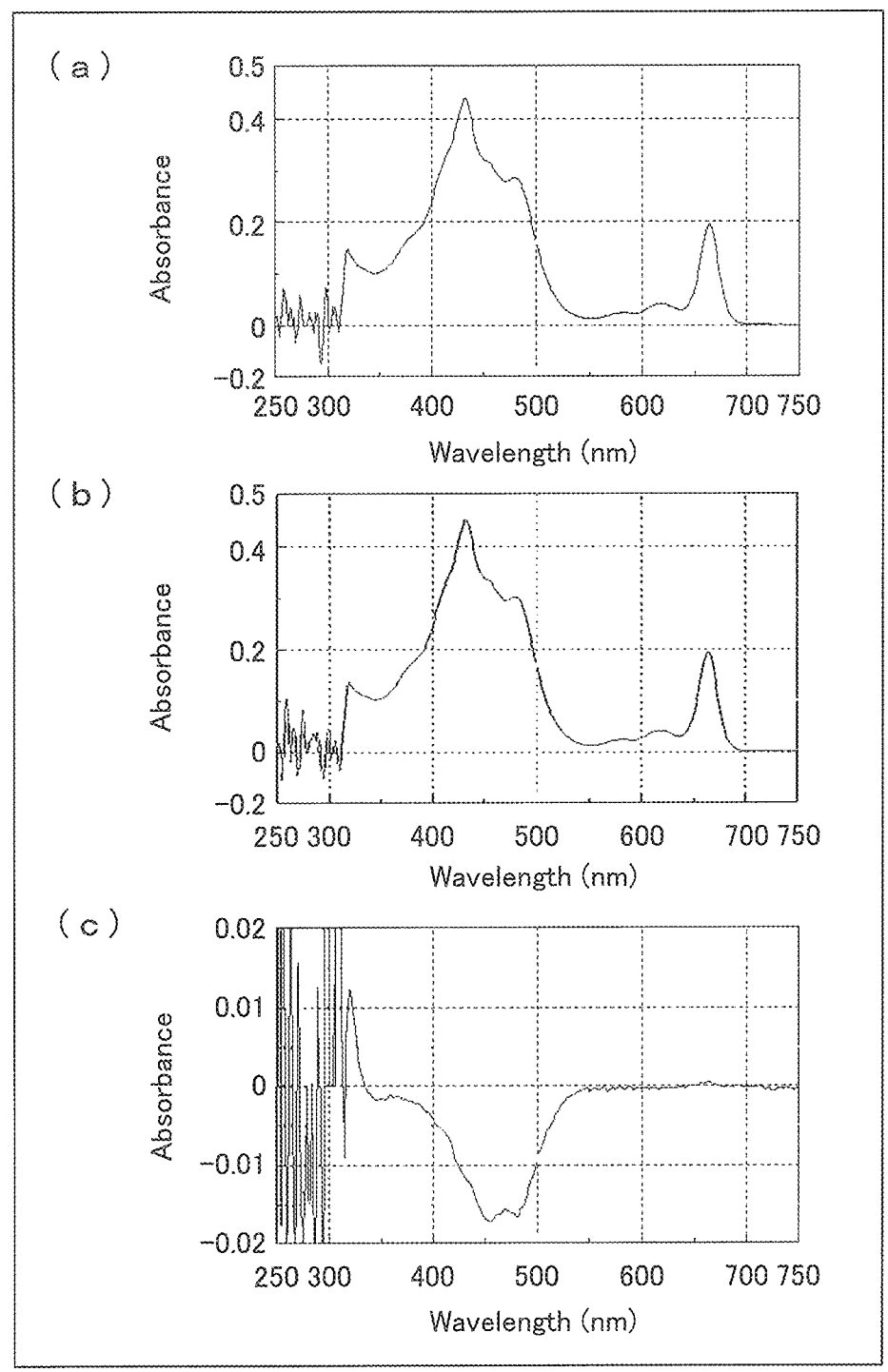

FIG. 18 shows a result of analysis of spectra of pigments extracted from the E.c.gshA plus strain and E.c.gshA minus strain, each of which is a transformant of *Cyanobacteria*. (a) of FIG. 18 shows an absorbance spectrum of the E.c.gshA plus strain, (b) of FIG. 18 shows an absorbance spectrum of the E.c.gshA minus strain, and (c) of FIG. 18 shows a spectrum obtained by subtracting the spectrum of the E.c.gshA minus strain from the spectrum of the E.c.gshA plus strain.

Figure 19:
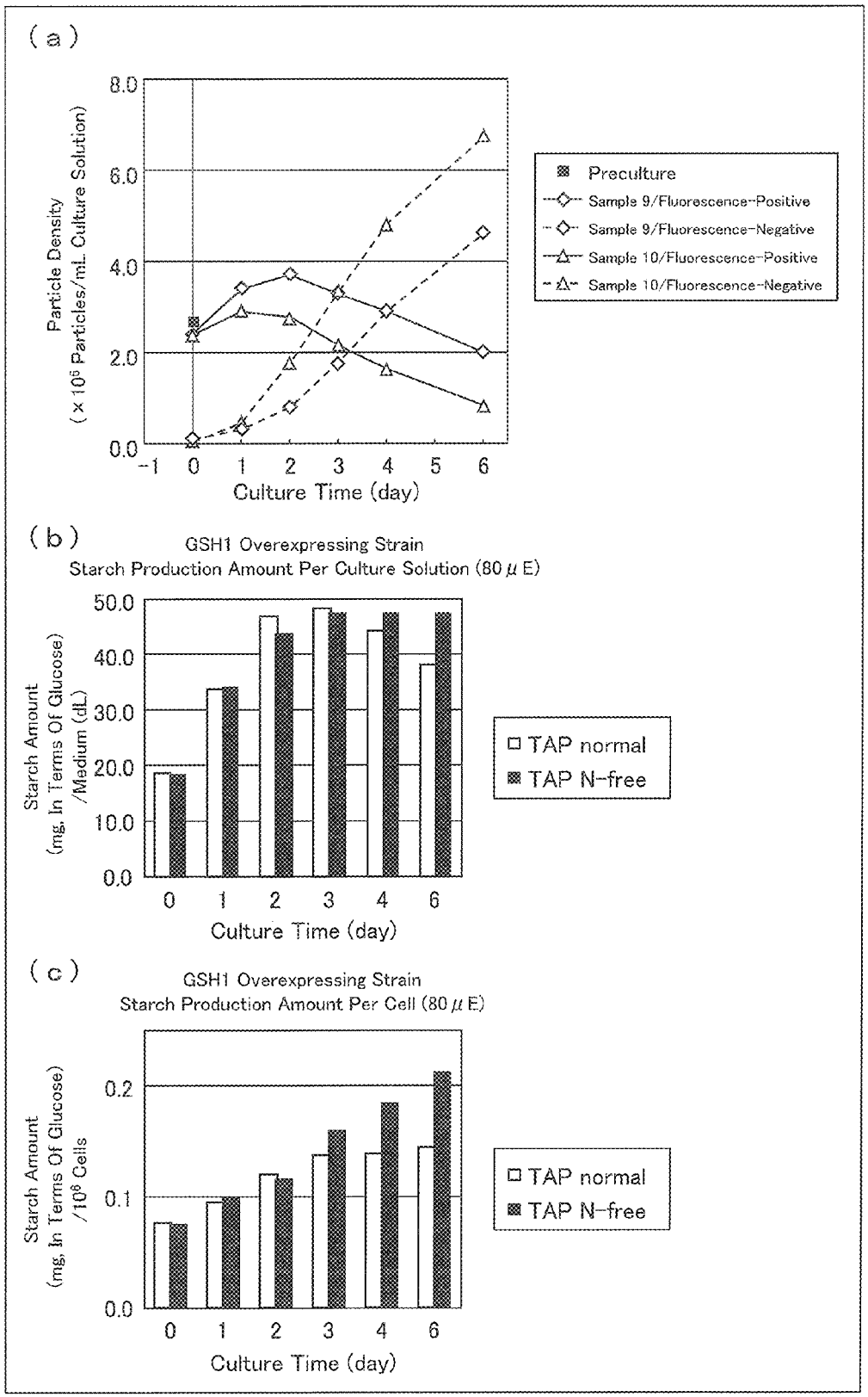

(a) of FIG. 19 is a graph showing (i) a time-course for density of particles (i.e., cells) that exhibit chlorophyll fluorescence and (ii) a time-course for density of particles (i.e., starch grains) that do not exhibit chlorophyll fluorescence in Samples 9 and 10, (b) of FIG. 19 is a graph showing a time-course for a starch amount per culture solution in Samples 9 and 10, and (c) of FIG. 19 is a graph showing a time-course for a starch amount per cells in Samples 9 and 10. In (b) and (c) of FIG. 19, "TAP normal" and "TAP N-free" in the legend represent "TAP medium containing a nitrogen source" and "TAP medium containing no nitrogen source", respectively.

Figure 20:
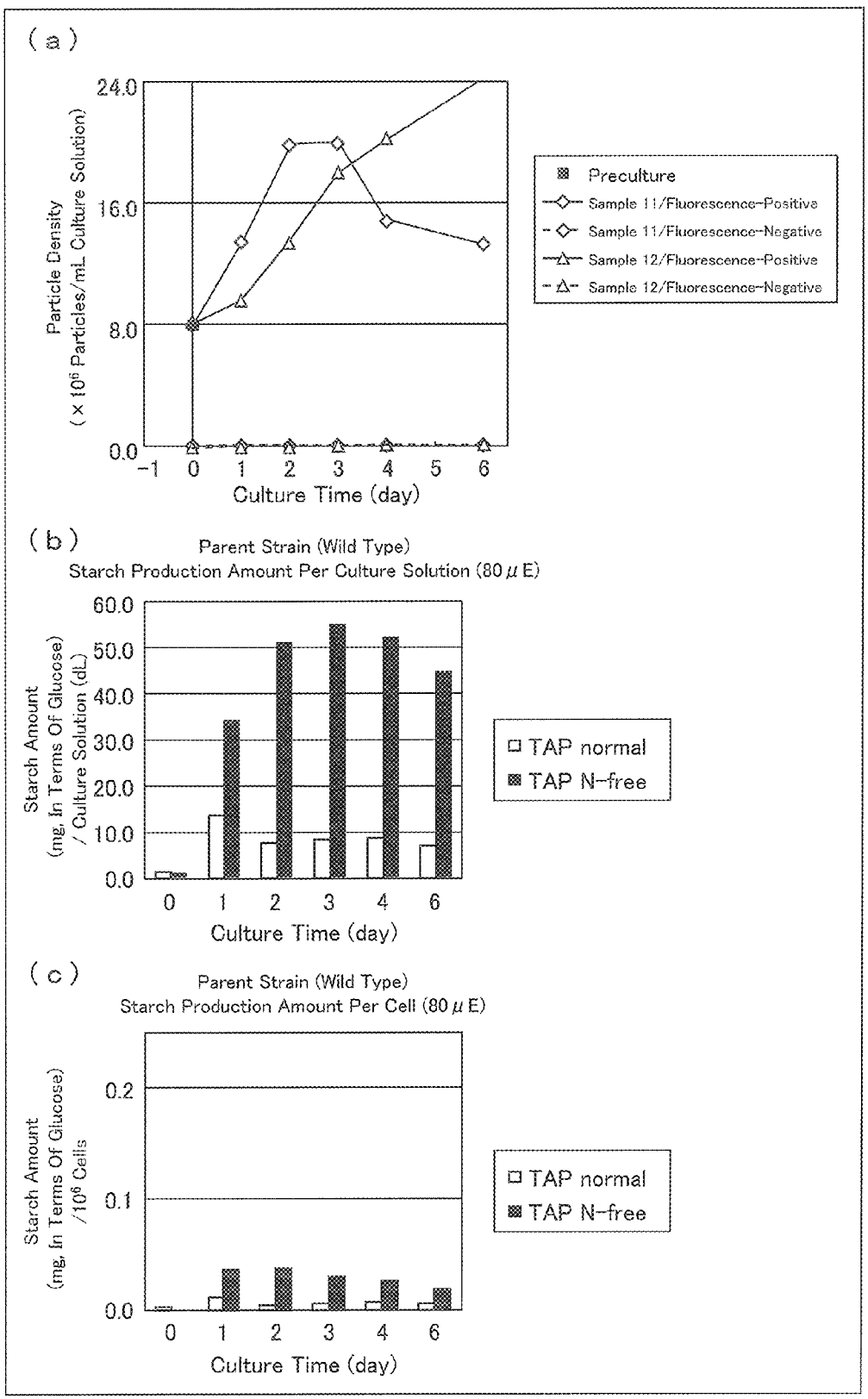

(a) of FIG. 20 is a graph showing (i) a time-course for density of particles (i.e., cells) that exhibit chlorophyll fluorescence and (ii) a time-course for density of particles (i.e., starch grains) that do not show chlorophyll fluorescence in Samples 11 and 12, (b) of FIG. 20 is a graph showing a time-course for a starch amount per culture solution in Samples 11 and 12, and (c) of FIG. 20 is a graph showing a time-course for a starch amount per cells in Samples 11 and 12. In (b) and (c) of FIG. 20, "TAP normal" and "TAP N-free" in the legend represent "TAP medium containing a nitrogen source" and "TAP medium containing no nitrogen source", respectively.

DESCRIPTION OF EMBODIMENTS

An embodiment of the present invention is described below in detail. Note, however, that the present invention is not limited to this, but may be altered in various ways within the scope of the claims. All of the academic literatures and patent literatures mentioned in this specification are incorporated by reference. A numerical range "A to B" means "not less than A and not more than B" unless otherwise specified.

[1. Alga of the Present Invention]

An alga of the present invention is not limited to a specific one, provided that it has an increased glutathione concentration in its chloroplast. Preferably, the alga of the present invention is an alga in which productivity of a photosynthate is increased.

In the present invention, what is meant by "increased glutathione concentration in chloroplast" is that a glutathione concentration in a chloroplast of an alga is higher than that of a wild-type alga of the same species. It is determined that an alga has an increased glutathione concentration in its chloroplast, preferably in a case where a glutathione concentration in a chloroplast of the alga is 1.1 or more times as high as that of a wild-type alga of the same species grown under the same condition, more preferably in a case where there is a significant difference of 5% level as a result of a t-test. Note that the glutathione concentration in the chloroplast of the wild-type alga is preferably one measured by the same method at the same time as the alga of the present invention, but data accumulated as background data may be used.

A glutathione concentration in a chloroplast of an alga can be directly measured by a method of introducing roGFP2, which is a molecular probe whose hue changes reflecting a redox state, into the chloroplast (see, for example, Meyer A J, et al. (2007) Plant Journal 52: 973-986. Redox-sensitive GFP in *Arabidopsis thaliana* is a quantitative biosensor for the redox potential of the cellular glutathione redox buffer and Gutscher M, et al. (2008) Nat Methods 5: 553-559. Real-time imaging of the intracellular glutathione redox potential). As an alternative to this method, a glutathione concentration can be indirectly measured by a method using, as an indicator, an expression amount of a protein which is involved in a glutathione biosynthesis system or an expression amount of a polynucleotide encoding the protein. According to this method, an increase of such an indicator is judged as an increase in glutathione concentration. A conventionally known method can be suitably used to measure an expression amount of such a protein and an expression amount of such a polynucleotide.

Examples of "glutathione" encompass reduced glutathione (hereinafter referred to as "GSH") and oxidized glutathione (hereinafter referred to as "GSSG"). According to a method of the present invention, it is only necessary to increase a glutathione concentration of at least one of GSH and GSSG. It is also possible to increase both of a concentration of GSH and a concentration of GSSG.

What is meant by "productivity of a photosynthate is increased" is that productivity of a photosynthate in an alga is higher than that in a wild-type alga of the same species. It is determined that productivity of a photosynthate is increased in an alga, preferably in a case where the productivity of the photosynthate in the alga is 1.1 or more as high as that of a wild-type alga of the same species grown under the same condition, more preferably in a case where there is a significant difference of 5% level as a result of a t-test. Productivity can be evaluated, for example, on the basis of various points such as conditions of irradiation light (e.g., light amount, light intensity, irradiation time), an administered nutrient, time length, necessity of a step of creating a starved state, and a cultivation temperature.

The "photosynthate" used herein refers to a substance produced by an alga as a result of carbon fixation occurring due to photosynthesis. Specific examples of the "photosynthate" are biomass encompassing oils and fats, saccharides (including starch), or the like, and its derivatives (metabolites). Note that the "carbon fixation occurring due to photosynthesis" used herein refers to overall carbon compound metabolism using chemical energy derived from optical energy. Accordingly, carbon taken in a metabolic system is derived not only from an inorganic compound such as carbon dioxide but also from an organic compound such as acetic acid.

The "alga" used herein is not limited in particular, provided that it has a photosynthetic capacity and is capable of producing a photosynthate. Examples of such an alga encompass microalgae classified in the class Chlorophyceae of the division Chlorophyta. More specifically, examples of such an alga encompass algae belonging to the genus *Chlamydomonas* of the class Chlorophyceae, such as *Chlamydomonas reinhardtii, Chlamydomonas moewusii, Chlamydomonas eugametos,* and *Chlamydomonas segnis*; algae belonging to the genus *Dunaliella* of the class Chlorophyceae, such as *Dunaliella salina, Dunaliella tertiolecta,* and *Dunaliella primolecta*; algae belonging to the genus *Chlorella* of the class Chlorophyceae, such as *Chlorella vulgaris* and *Chlorella pyrenoidosa*; algae belonging to the genus *Haematococcus* of the class Chlorophyceae, such as *Haematococcus pluvialis*; algae belonging to the genus *Chlorococcum* of the class Chlorophyceae, such as *Chlorococcum littorale*; algae belonging to the genus *Botryococcus* of the class Chlorophyceae or the class Xanthophyceae, such as *Botryococcus braunii*; algae belonging to the genus *Choricystis* of the class Chlorophyceae, such as *Choricystis minor*; algae belonging to the genus *Pseudochoricystis* of the class Chlorophyceae, such as *Pseudochoricystis ellipsoidea*; algae belonging to the genus *Amphora* of the class Bacillariophyceae, such as *Amphora* sp.; algae belonging to the genus *Nitzschia* of the class Bacillariophyceae, such as *Nitzschia alba, Nitzschia closterium,* and *Nitzschia laevis*; algae belonging to the genus *Cryptheco-dinium* of the class Dinophyceae, such as *Crypthecodinium cohnii*; algae belonging to the genus *Euglena* of the class Euglenophyceae, such as *Euglena gracilis* and *Euglena proxima*; algae belonging to the genus *Paramecium* of the division Ciliophora, such as *Paramecium bursaria*; algae belonging to the genus *Synechococcus* of the division Cyanophyta, such as *Synechococcus aquatilis* and *Synechococcus elongatus*; algae belonging to the genus *Spirulina* of the division Cyanophyta, such as *Spirulina platensis* and *Spirulina subsalsa*; algae belonging to the genus *Prochlorococcus* of the division Cyanophyta, such as *Prochlorococcus marinus*; and algae belonging to the genus *Oocystis* of the division Cyanophyta, such as *Oocystis polymorpha*.

A method for obtaining an alga having an increased glutathione concentration in its chloroplast is not limited in particular. This method is specifically described in "2. Method of the present invention for producing alga" that will be described later.

The alga of the present invention is preferably arranged such that an expression amount and/or an activity of a protein are increased in a chloroplast of the alga, the protein being at least one protein selected from the group consisting of γ-glutamylcysteine synthetase (hereinafter referred to also as "GSH1"), glutathione synthetase (hereinafter referred to also as "GSH2"), ATP-sulfurylase, adenosine 5'-phosphosulfate reductase, sulfite reductase, cysteine synthetase, and serine acetyl transferase. Since these proteins are enzymes that are involved in a glutathione biosynthesis system in a chloroplast, an increase in expression amount of these proteins can be regarded as an increase in glutathione concentration in a chloroplast.

Alternatively, the alga of the present invention may be an alga into which a polynucleotide encoding a protein is introduced, the protein being at least one protein selected from the group consisting of GSH1, GSH2, ATP-sulfurylase, adenosine 5'-phosphosulfate reductase, sulfite reductase, cysteine synthetase, and serine acetyl transferase. An alga into which such an exogenous polynucleotide is introduced and is (excessively) expressed can be considered as an alga having an increased glutathione concentration in its chloroplast.

In other words, it can be said that the present invention provides a transformed alga having an increased glutathione concentration in its chloroplast as a result of introduction of a polynucleotide encoding a protein which is at least one protein selected from the group consisting of GSH1, GSH2, ATP-sulfurylase, adenosine 5'-phosphosulfate reductase, sulfite reductase, cysteine synthetase, and serine acetyl transferase. As a natural consequence, such a transformed alga is increased in photosynthate productivity.

In the alga of the present invention, the polynucleotide encoding glutamylcysteine synthetase may be selected from the group consisting of the following (a) through (d):

(a) a polynucleotide encoding a polypeptide consisting of the amino-acid sequence represented by SEQ ID NO: 1;

(b) a polynucleotide encoding a polypeptide which consists of an amino-acid sequence with deletion, substitution, or addition of one or several amino acids in the amino-acid sequence represented by SEQ ID NO: 1 and which has a γ-glutamylcysteine synthetase activity;

(c) a polynucleotide consisting of the nucleotide sequence represented by SEQ ID NO: 2; and (d) a polynucleotide which hybridizes under a stringent condition with a polynucleotide consisting of a nucleotide sequence complementary to any one of the polynucleotides (a) through (c) and which encodes a polypeptide having a γ-glutamylcysteine synthetase activity. Details of the polynucleotides (a) through (d) are described later.

Whether or not the polynucleotide has been introduced into a cell of the alga of the present invention can be confirmed by a conventionally known method such as a PCR method, a southern hybridization method, or a northern hybridization method. Alternatively, whether or not the polynucleotide has been introduced into a cell of the alga of the present invention can be confirmed by measuring expression of a protein which the polynucleotide encodes by a conventionally known immunological method. Alternatively, whether or not the polynucleotide has been introduced into a cell of the alga of the present invention can be confirmed by measuring enzyme activity of a protein which the polynucleotide encodes by a conventionally known physiological method.

Since the alga of the present invention has an increased glutathione concentration in its chloroplast, production and/or accumulation of a photosynthate in a cell of the alga can be induced without creating a nitrogen-starved state. As a consequence, use of the alga of the present invention makes it unnecessary to replace a nitrogen-containing culture solution with a nitrogen-free culture solution for inducing accumulation of a photosynthate.

The following describes effects of the present invention in comparison with a wild-type alga. Explained first is a case where a nitrogen-starved state is created under a heterotrophic condition (condition in which a carbon source such as acetic acid is present). In this case, a wild-type alga slightly accumulates a photosynthate in its cells during a growth phase and accumulates the photosynthate during a stationary phase, but the photosynthate is hardly detected outside the cells. In contrast, the alga of the present invention produces and accumulates a photosynthate both during a growth phase (logarithmic growth phase) and during a stationary phase, and a large amount of photosynthate is detected outside the cells. Explained next is a case where a nitrogen-starved state is not created under a heterotrophic condition. In this case, the wild-type alga very slightly accumulates a photosynthate in its cells during the growth phase, but the level of the accumulation further declines in the stationary phase, and the photosynthate is hardly detected outside the cells. In contrast, the alga of the present invention produces and accumulates a photosynthate both during the growth phase and during the stationary phase, and a large amount of photosynthate is detected outside the cells.

Explained next is an autotrophic condition (condition in which growth depends on carbon dioxide fixation occurring due to photosynthesis). Under the autotrophic condition, the wild-type alga generally requires a larger light amount for induction of accumulation of a photosynthate in the nitrogen-starved state than under the heterotrophic condition. In contrast, the alga of the present invention continues to produce a photosynthate without the need to increase the light intensity. Needless to say, also in the alga of the present invention, the productivity of a photosynthate increases as the intensity of light with which the alga is irradiated is increased. For example, in a case where *Chlamydomonas* is used as the alga, it is advantageous for production of a photosynthate, in view of properties of *Chlamydomonas*, to irradiate the alga with strong light. However, restriction by a light amount on accumulation of a photosynthate is extremely limited in the alga of the present invention, as compared with the wild-type alga.

Further, the alga of the present invention maintains small growth density. Accordingly, the alga of the present invention is high in light use efficiency. Consequently, the alga of the present invention can produce and accumulate a larger amount of photosynthate than a wild-type alga of the same species, even in a case where these algae are irradiated with the same amount of light (light of the same brightness). In general, an alga that is in an appropriate level in terms of cell density (e.g., an alga in which a cell density is maintained at a lower level than a wild-type alga) is advantageous in terms of light use efficiency. Specifically, the alga of the present invention, in which a growth density is maintained at a lower level than a wild-type alga, can avoid a problem that a photosynthate production capacity peaks out at a certain point, which problem occurs because as a cell density increases, light reaching a deep layer of a culture tank attenuates due to a "shading effect" caused by cells present on a superficial layer of the culture tank.

Further, the alga of the present invention can accumulate starch grains so that the accumulation of the starch grains linearly increases corresponding to a cultivation time. Accordingly, by maintaining such a cultivation state by water replenishment and addition of culture medium, it is possible to successively produce a photosynthate (so-called continuous cultivation) (e.g., continuously produce starch as starch grains).

Alternatively, the alga of the present invention has a larger space for an increase in growth density than a wild-type alga. It is possible to effectively produce a photosynthate by increasing a growth density to a saturation point of productivity of the photosynthate through artificial manipulation (e.g., reduction of a cell dispersion medium (e.g., water) through a filtration step or the like).

Further, the alga of the present invention is small in the number of resting cells. Accordingly, biomass production using the alga of the present invention makes it possible to achieve a good yield and a saving on a culture solution. Moreover, it is possible to reduce an amount of waste, thereby allowing a reduction in cost for disposing the waste (dehydration, incineration, landfill, etc.). This is advantageous especially in a case where batch cultivation is carried out. Further, such a small amount of waste leads to a good yield. Specifically, for example, in the case of fermentation such as wine brewing, most of solid materials in waste are cells. Meanwhile, according to the alga of the present invention, rupture and autolysis of cells occur following release of starch grains, and therefore decomposed dead cells serve for the nutrition of other cells. As a result, a yield increases.

Further, the alga of the present invention allows a photosynthate accumulated in its cells to be discharged towards an outside of the cells. This makes it easy to collect the photosynthate. For example, in a case where the photosynthate is starch, starch accumulated as a result of photosynthesis can be discharged towards an outside of cells of the alga as starch grains without the need to crush the cells. As a consequence, biomass production using the alga of the present invention allows relatively easy purification of starch.

The starch grains produced by the alga of the present invention are extremely small. For example, general starch grains produced from corn, potato, wheat, or the like are 10 µm to 50 µm in average particle diameter, whereas starch grains produced by the alga of the present invention are extremely small particles of uniform sizes whose average particle diameter of the major axis is 1.3 µm (standard deviation 0.181) and whose average particle diameter of the manor axis is 1.0 µm (standard deviation 0.204). Although starch grains produced by rice, quinoa, or the like are extremely small grains whose average particle diameter is approximately 2 µm to 3 µm, these starch grains adhere tightly to each other so as to form organized albumin, as with starch grains produced by corn, potato, wheat, or the like. This requires a costly process such as grinding in order to prepare, from a raw material such as corn, potato, wheat, rice, or quinoa, extremely small starch grains that are disaggregate from each other. Such extremely small starch grains are useful for production of medicaments. That is, use of the alga of the present invention allows not only mass production of extremely small starch grains of uniform sizes, but also relatively easy purification since the starch grains are discharged into an outside of cells of the alga. Moreover, these starch grains are disaggregate from each other without the process such as grinding.

As described above, starch grains produced by a GSH1 overexpressing strain are smaller than general starch grains produced by corn, potato, wheat, or the like. Such extremely small starch grains are useful for production of medicines. Specifically, such starch grains are smaller than a diameter of bronchioli of the lung, and are therefore expected to be used as carriers (dry power inhaler combining a drug for a lung disease and starch fine particles) for transporting the drug into bronchioli.

Further, these starch grains are expected to be used as so-called "edible vaccine" by attaching a peptide antigen to surfaces of the starch grains (for example, Dauvillé e et al. 2010, PLos One Vol. 5, No. 12, e15424; Translation of PCT Application, Tokuhyo, No. 2003-500060 (Japanese Patent Application, Tokugan, No. 2000-620111) discloses that a malaria antigen is attached on surfaces of starch grains of *Chlamydomonas*.)

Note that glutathione is a substance for regulating a redox status in a cell. It is known that glutathione can function as a differentiation control agent for cells and organs (see WO 01/080638) and can function as a plant growth-regulation adjuvant (see Japanese Patent Application Publication, Tokukai, No. 2004-352679 A).

However, it is unpredictable, from the conventionally known functions of glutathione, that (i) increasing a glutathione concentration in a chloroplast of an alga can induce accumulation of a photosynthate in a cell of the alga without the need to create a nitrogen-starved state and (ii) the photosynthate accumulated in the cell of the alga can be discharged into an outside of the cell.

Use of the alga of the present invention makes it possible to more easily and efficiently (i) induce accumulation of a photosynthate and (ii) collect the photosynthate, as compared with a conventional art. Accordingly, by using the alga of the present invention in a biomass production method that is described later, it is possible to more efficiently produce biomass from the alga at lower cost as compared with a conventional art.

[2. Method of the Present Invention for Producing Alga]

A method for producing an alga in accordance with the present invention (hereinafter referred to as "method of the present invention for producing an alga") is a method for producing an alga (the alga of the present invention) in which a glutathione concentration in a chloroplast and productivity of a photosynthate are increased as compared with a wild-type alga. The method of the present invention for producing an alga is not limited in terms of conditions, steps, etc., provided that it includes at least the step of increasing a glutathione concentration in a chloroplast of the alga.

The following specifically describes a method of the present invention for producing an alga.

(1. Step of Increasing Glutathione Concentration)

The step of increasing a glutathione concentration is a step of increasing a glutathione concentration in a chloroplast of an alga.

What is meant by "increasing a glutathione concentration in a chloroplast" is that the glutathione concentration in the chloroplast of the alga is increased to be higher than that of a wild-type alga of the same species. In other words, an alga that has been subjected to the step of increasing a glutathione concentration has a higher glutathione concentration than the wild-type alga of the same species. Whether or not a glutathione concentration in a chloroplast of an alga has been increased to be higher than that of a wild-type strain of the alga can be judged by the method described in "1. Alga of the present invention".

A method for increasing a glutathione concentration in a chloroplast in the step of increasing a glutathione concentration is not limited in particular, provided that it can eventually increase a glutathione concentration in a chloroplast of an alga. For example, an alga having an increased glutathione concentration in its chloroplast can be obtained by a method such as (i) a method of randomly introducing a mutation into a target alga by a known mutation introducing method or (ii) a method of introducing, into a cell of an alga (into a genome of the alga in some cases), a substance for increasing a glutathione concentration in a chloroplast.

The following specifically describes the methods (i) and (ii).

(i) Method of Randomly Introducing a Mutation into an Alga

The method of randomly introducing a mutation into an alga is not limited in particular, and can be one appropriately selected from known methods. Specifically, examples of such a method include (a) a method of treating an alga with a chemical substance (e.g., EMS, NTG), (b) a method utilizing radiation, (c) a method utilizing a transposon, (d) a method utilizing T-DNA, (e) a method utilizing prokaryotic/eukaryotic cell conjugation, and (f) a method of physically introducing a mutation with the use of a gene gun. By using such a method, a mutation is introduced into a polynucleotide encoding a protein (such as GSH1, GSH2, ATP-sulfurylase, adenosine 5'-phosphosulfate reductase, sulfite reductase, cysteine synthetase, or serine acetyl transferase) that is involved in a glutathione biosynthesis system in a chloroplast, thereby increasing an expression amount and/or an activity of the protein. As a result, an alga having an increased glutathione concentration in its chloroplast can be obtained.

A method for distinguishing an alga into which a desired mutation has been introduced is not limited in particular, and can be a known method. Examples of such a method include (a) a method of obtaining a mutant alga having an increased glutathione concentration by using the above-mentioned method of directly measuring a glutathione concentration in a chloroplast and (b) a method of obtaining a mutant alga in which an expression amount and/or an activity of a protein such as GSH1, GSH2, ATP-sulfurylase, adenosine 5'-phosphosulfate reductase, sulfite reductase, cysteine synthetase, or serine acetyl transferase is increased.

(ii) Method of Introducing, into a Cell, a Substance for Increasing a Glutathione Concentration in a Chloroplast The "substance for increasing a glutathione concentration in a chloroplast" is, for example, (A) a polynucleotide encoding a protein for increasing a glutathione concentration in a chloroplast of an alga or (B) a polynucleotide having a function of reducing an expression amount of a protein for reducing a glutathione concentration in a chloroplast of an alga. An alga having an increased glutathione concentration in its chloroplast can be obtained, for example, by introducing the polynucleotide (A) and/or the polynucleotide (B) into a cell of the alga. Note that the polynucleotide (A) and the polynucleotide (B) may be used alone or may be used in combination.

The term "polypeptide" used herein is interchangeable with "peptide" or "protein". The term "polynucleotide" used herein is interchangeable with "gene", "nucleic acid" or "nucleic acid molecule", and refers to a nucleotide polymer.

The expression "introducing a polynucleotide" means that a polynucleotide to be introduced is present in a cell of an alga, and encompasses a case where a polynucleotide to be introduced is inserted (introduced) into a genome of an alga. Whether or not a polynucleotide has been introduced into a cell of an alga can be confirmed by a conventionally known method such as a PCR method, a southern hybridization method, or a northern hybridization method.

By introducing at least one kind of the polynucleotide (A) into a cell of an alga, it is possible to increase an expression amount of a protein for increasing a glutathione concentration in a chloroplast. As a result, it is possible to increase the glutathione concentration in the chloroplast.

Preferable Examples of such a polynucleotide encompass a polynucleotide (hereinafter referred to also as "GSH1 gene") encoding γ-glutamylcysteine synthetase, a polynucleotide (hereinafter referred to also as "GSH2 gene") encoding glutathione synthetase, a polynucleotide encoding ATP-sulfurylase, a polynucleotide encoding adenosine 5'-phosphosulfate reductase, a polynucleotide encoding sulfite reductase, a polynucleotide encoding cysteine synthetase, and a polynucleotide encoding serine acetyl transferase. Each of these polynucleotides is preferably derived from a plant, more preferably one which a host alga itself has. Note, however, that a polynucleotide derived from an alga different from the host alga and a polynucleotide derived from other higher plants can be suitably used.

The "γ-glutamylcysteine synthetase (GSH1)" is an enzyme which synthesizes γ-glutamylcysteine by amid-bonding glutamic acid with cysteine at γ position. The "glutathione synthetase (GSH2)" is an enzyme which synthesizes glutathione by adding glycine to γ-glutamylcysteine.

Although specific examples of the "GSH1 gene" are not limited in particular, a preferable example of the GSH1 gene for use in the present invention is a GSH1 gene (CHLRE-DRAFT_181975) of Chlamydomonas which the inventors of the present invention used in Examples. The GSH1 of Chlamydomonas consists of the amino-acid sequence represented by SEQ ID NO: 1, and a gene (full-length cDNA) encoding the GSH1 of Chlamydomonas consists of the nucleotide sequence represented by SEQ ID NO: 3. In the nucleotide sequence represented by SEQ ID NO: 3, the sequence from position 134 to position 136 is a start codon, and the sequence from position 1571 to position 1573 is a stop codon. That is, the Chlamydomonas GSH1 gene has the sequence from position 134 to position 1573 of the nucleotide sequence represented by SEQ ID NO: 3 as an open reading frame (ORF). The nucleotide sequence represented by SEQ ID NO: 2 is a nucleotide sequence of the ORF of the Chlamydomonas GSH1 gene. A translated product of the Chlamydomonas GSH1 gene has a chloroplast targeting signal peptide in its N-terminus region. Accordingly, the translated product of the Chlamydomonas GSH1 gene, i.e., Chlamydomonas GSH1 is normally present in a chloroplast.

That is, in the present invention, preferable examples of a nucleotide to be introduced into an alga are the following polynucleotides (a) through (d):

(a) a polynucleotide encoding a polypeptide consisting of the amino-acid sequence represented by SEQ ID NO: 1;

(b) a polynucleotide encoding a polypeptide which consists of an amino-acid sequence with deletion, substitution, or addition of one or several amino acids in the amino-acid sequence represented by SEQ ID NO: 1 and which has a γ-glutamylcysteine synthetase activity;

(c) a polynucleotide consisting of the nucleotide sequence represented by SEQ ID NO: 2; and (d) a polynucleotide which hybridizes under a stringent condition with a polynucleotide consisting of a nucleotide sequence complementary to any one of the polynucleotides (a) through (c) and which encodes a polypeptide having a γ-glutamylcysteine synthetase activity.

The nucleotide sequence represented by SEQ ID NO: 2 is an example of the nucleotide sequence encoding a polypeptide consisting of the amino-acid sequence represented by SEQ ID NO: 1.

What is meant by "deletion, substitution, or addition of one or several amino acids" is deletion, substitution, or addition of an amino acid(s) (preferably not more than 10 amino acids, more preferably not more than 7 amino acids, further more preferably not more than 5 amino acids) almost as many as those that can be deleted, substituted, or added by a known mutant peptide production method such as site-directed mutagenesis. Such a mutant protein is not limited to a protein having a mutation artificially introduced by a known mutant peptide production method, and can be one obtained by isolating and purifying a naturally-occurring protein.

It is well known in the art that some of amino acids in an amino-acid sequence of a protein can be easily modified without significantly affecting a structure or functions of the protein. It is also well known in the art that a protein has a naturally-occurring mutant which does not significantly change a structure or function of the protein, apart from an artificially-altered protein.

It is preferable that a mutant includes conservative or non-conservative substitution, deletion, or addition of amino acid(s). In this regard, silent substitution, addition, and deletion are more preferable, and conservative substitution is particularly preferable. Such mutations do not change a polypeptide activity in accordance with the present invention.

It is considered that representative examples of the conservative substitution are: substitution of one amino acid with another among aliphatic amino acids Ala, Val, Leu, and Ile; exchange of hydroxyl residues Ser and Thr; exchange of acidic residues Asp and Glu; substitution between amide residues Asn and Gln; exchange of basic residues Lys and Arg; and substitution between aromatic residues Phe and Tyr.

The "stringent condition" in the present specification means such a condition that sequences hybridize with each other only when the sequences have at least 90% identity, preferably at least 95% identity, most preferably at least 97% identity. Specifically, the "stringent condition" includes, for example, incubation overnight at 42° C. in a hybridization solution (50% formamide, 5×SSC (150 mM NaCl and 15 mM trisodium citrate), 50 mM sodium phosphate (pH7.6), 5×Denhardt's solution, 10% dextran sulfate, and 20 µg/mL denatured fragmented salmon sperm DNA) and washing of a filter in 0.1×SSC at approximately 65° C.

The hybridization can be carried out by means of a known method such as one described in Sambrook et al., Molecular cloning, A Laboratory Manual, 3rd Ed., Cold Spring Harbor Laboratory (2001). Generally, the higher the temperature is and the lower the salt concentration is, the higher the stringency becomes (the hybridization becomes more difficult to occur). The higher stringency makes it possible to obtain a polynucleotide with a higher homology.

Identity between amino-acid sequences or between nucleotide sequences can be determined by use of an algorithm BLAST according to Karlin and Altschul (Karlin S, Altsuchul S F, Proc. Natl. Acad. Sci. USA, 87: 2264-2268 (1990); Karlin S, Altschul S F, Proc. Natl. Acad Sci. USA, 90: 5873-5877 (1993)). Programs based on the algorithm BLAST, called BLASTN and BLASTX, have been developed (Altschul S F, et al., J. Mol. Biol., 215: 403 (1990)).

In the present invention, the "γ-glutamylcysteine synthetase activity" means the activity of catalyzing a reaction of amid-bonding glutamic acid with cysteine at γ position. The "γ-glutamylcysteine synthetase activity" can be found as follows, for example: an alga is crushed under nitrogen atmosphere as anti-oxidation measure. A solution which contains the crushed alga therein is centrifuged to give a supernatant as a sample. The sample is added to a reaction solution containing cysteine, glutamic acid, and ATP, so that γ-glutamylcysteine is synthesized. The γ-glutamylcysteine synthetase activity is found as an amount of the γ-glutamylcysteine synthesized for a given length of time. As another method, it is also possible to find γ-glutamylcysteine synthetase activity by measuring an amount of phosphoric acid generated along with the reaction.

Known examples of plant-derived GSH1 genes other than the *Chlamydomonas* GSH1 gene encompass a gene of *A. thaliana* (TAIR Accession Gene: 2127172, Name AT4G23100.1), a gene of *Zinnia elegans* (Genbank accession: AB158510), a gene of *Oryza sativa* (Genbank accession: AJ508915), a gene of *Nicotiana tabacum* (Genbank accession: DQ444219), and the like. These genes can be also preferably used in the present invention. Translated products of these genes also have a chloroplast targeting signal peptide in the N-terminal region, similarly to that of *Chlamydomonas*.

Further, by introducing the polynucleotide (B) into a cell of an alga, it is possible to reduce an expression amount of a protein which reduces a glutathione concentration in a chloroplast. As a result, it is possible to increase the glutathione concentration in the chloroplast. Examples of such a polynucleotide encompass double-stranded RNA (dsRNA), siRNA (short interfering RNA), and template DNA of these RNAs, each of which is used in a conventionally known RNA interference (RNAi) method.

A preferable example of the "protein which reduces a glutathione concentration in a chloroplast of an alga" is CLT1. "CLT1" is a transporter for transporting glutathione from a chloroplast to cytoplasm. Such a transporter was found first in *A. thaliana* and named CLT1 (see Proc Natl Acad Sci USA (2010) vol. 107 (5) 2331-2336). That is, a polynucleotide that is intended to reduce an expression amount of a glutathione transporter such as CTL1 can be exemplified as the polynucleotide (B).

The "polynucleotide" for use in the method of the present invention for producing an alga may be derived from a genomic DNA or cDNA, and may be a chemosynthetic DNA. Further, the "polynucleotide" may be RNA. The "polynucleotide" for use in the method of the present invention for producing an alga can be appropriately selected according to the purpose.

A method for obtaining a polynucleotide for use in the method of the present invention for producing an alga may be a method for isolating and cloning, by use of a known technique, a DNA fragment encoding GSH1, for example, in the case of obtaining a GSH1 gene. The method may be such that a probe that specifically hybridizes with part of a nucleotide sequence of DNA encoding GSH1 of *Chlamydomonas* is prepared and a genomic DNA library or a cDNA library is screened with the probe.

Alternatively, the method for obtaining a polynucleotide for use in the method of the present invention for producing an alga can be a method using amplification means such as PCR. For example, in the case of obtaining a GSH1 gene, primers are prepared respectively from sequences on the 5' side and the 3' side (or their complementary sequences) of cDNA encoding GSH1 of *Chlamydomonas*. Then, PCR or the like is carried out with use of the primers and a genomic DNA (or cDNA) as a template, so as to amplify a DNA region between the primers. This makes it possible to obtain a great amount of DNA fragments (GSH1 genes) encoding GSH1 for use in the present invention. A GSH2 gene, an ATP-sulfurylase gene, an adenosine 5'-phosphosulfate reductase gene, a sulfite reductase gene, a cysteine synthetase gene, a serine acetyl transferase gene, and a CLT1 gene also can be obtained by a similar method.

The polynucleotide for use in the method of the present invention for producing an alga can be obtained from a desired alga as a source.

A method for introducing a polynucleotide into an alga in the method of the present invention for producing an alga is not limited in particular. For example, the polynucleotide can be introduced into a cell of an alga by introducing an expression vector having the polynucleotide. A method for constructing an expression vector is not limited in particular, and can be a conventionally known method. For example, a recombinant expression vector in which a promoter functioning in an alga cell is connected to an upstream of a polynucleotide to be introduced and a terminator functioning in an alga cell is connected to a downstream of the polynucleotide to be introduced can be constructed and introduced into an alga in accordance with the expression vector construction method disclosed in Japanese Patent Application Publication, Tokukai, No. 2007-43926 and the alga transformation method disclosed in Japanese Patent Application Publication, Tokukaihei, No. 10-0570868.

A suitable example of the "promoter" is a PsaD promoter. The PsaD promoter is higher in promoter activity than an endogenous promoter of the GSH1 gene. Accordingly, use of the PsaD promoter makes it possible to express a larger amount of γ-glutamylcysteine synthetase. Moreover, since the PsaD gene is involved in photosynthesis, an expression vector obtained with the use of the PsaD promoter makes it possible to regulate an expression amount of a gene to be introduced by changing intensity of irradiation light when the expression vector is introduced into a cell of an alga.

(2. Other Steps)

The method of the present invention for producing an alga may further include the step of carrying out screening for an alga having an increased glutathione concentration in a chloroplast in addition to the "step of increasing a glutathione concentration".

For example, first, transformed algae into which an intended gene has been introduced are screened by a conventionally known chemical selective method by using, as an indicator, expression of a chemical-resistant marker such as a kanamycin-resistant marker or a hygromycin-resistant marker. Then, whether the intended gene has been introduced into an alga or not can be determined by using a PCR method, a southern hybridization method, a northern hybridization method, or the like. For example, DNA is prepared from a transformed alga, and primers specific to the introduced DNA are designed, and PCR is carried out. After that, amplification products are subjected to agarose gel electrophoresis, polyacrylamide gel electrophoresis, or capillary electrophoresis, and then stained with ethidium bromide so that an intended amplification product is detected, whereby the transformation can be confirmed.

As screening for an individual having an increased glutathione concentration in a chloroplast, the above-mentioned method for measuring a glutathione concentration in a chloroplast can be used for example.

Since an increase in a glutathione concentration in a chloroplast results in an increase in productivity of a photosynthate, it can be easily understood that an alga having an increased glutathione concentration in a chloroplast is an alga in which productivity of a photosynthate is increased. Whether or not productivity of a photosynthate is increased in an individual found through screening can be determined by the above-mentioned method for measuring productivity of a photosynthate.

[3. Method of the Present Invention for Producing Biomass]

A method for producing biomass in accordance with the present invention (hereinafter referred to as "method of the present invention for producing biomass") is a method for producing biomass with the use of an alga (the alga of the present invention) in which a glutathione concentration in a chloroplast is increased to be higher than that of a wild-type alga or an alga produced by the method of the present invention for producing an alga.

The alga of the present invention and the method of the present invention for producing an alga have been described in [1. Alga of the present invention] and [2. Method of the present invention for producing alga], respectively, and therefore are not described here repeatedly.

The "biomass" used herein refers to a substance, such as oils and fats, or saccharides (including starch), that is produced by an alga as a result of carbon fixation occurring due to photosynthesis, and is interchangeable with "photosynthate".

In the method of the present invention for producing biomass, a method for inducing production or accumulation of a photosynthate in a cell of an alga is not limited in particular. For example, the method of the present invention for producing biomass may include the step of irradiating an alga with light in order to induce production or accumulation of a photosynthate in a cell of the alga.

According to a conventional method, it is necessary to (i) create a nitrogen-starved condition in order to induce accumulation of a photosynthate in a cell of an alga and (ii) irradiate the alga with light in an amount of not less than 200 $\mu E/m^2$/second in order to promote remarkable accumulation of a photosynthate. In contrast, according to the method of the present invention for producing biomass, it is possible to induce accumulation of a photosynthate without the need to regulate a light amount. Note, however, that in the method of the present invention for producing biomass, an alga is preferably irradiated with light in an amount of not more than 1000 $\mu E/m^2$/second, more preferably not more than 500 $\mu E/m^2$/second, further more preferably not more than 400 $\mu E/m^2$/second, not more than 300 $\mu E/m^2$/second, not more than 200 $\mu E/m^2$/second, not more than 150 $\mu E/m^2$/second, not more than 100 $\mu E/m^2$/second, or not more than 80 $\mu E/m^2$/second. As the amount of irradiation light becomes smaller, energy efficiency improves, and therefore productivity increases. The alga of the present invention is superior to a conventional wild-type alga in that production of a photosynthate inside and outside a cell is possible with a smaller light amount. Note that a lower limit of the amount of irradiation light is not limited in particular, but a realistic value of the lower limit is, for example, not less than 40 $\mu E/m^2$/second.

No special light irradiation device is necessary to irradiate an alga with light in the above range. For example, solar light; light regulated both in quality and quantity by a mirror, an optical fiber, a filter, a mesh, or the like; artificial light such as an incandescent lamp, a fluorescent lamp, a mercury lamp, or a light-emitting diode can be used. Further, the irradiation light can be light having a wavelength suitable for photosynthesis of a general alga, and is preferably light having, for example, a wavelength ranging from 400 nm to 700 nm.

Moreover, according to the method of the present invention for producing biomass, it is possible to induce production or accumulation of a photosynthate in a cell of an alga without the need to cultivate the alga under a nitrogen-starved condition. Accordingly, the step of irradiating an alga with light may be carried out under a condition where nitrogen is not starved. The "condition where nitrogen is not starved" means that an alga is cultivated in a culture solution containing inorganic nitrogen in an amount necessary for growth of the alga. The "amount necessary for growth of the alga" means that inorganic nitrogen contained in the culture solution is 0.001% to 0.1% by weight, preferably 0.005% to 0.05% by weight in terms of nitrogen atoms. The "inorganic nitrogen" refers to nitrogen such as ammonia nitrogen, nitrite nitrogen, nitrate nitrogen. Note that, in the TAP medium used in Examples described later, inorganic nitrogen contained in a culture solution is approximately 0.01% by weight in terms of nitrogen atoms.

The culture solution containing inorganic nitrogen in an amount necessary for growth of an alga is not limited in particular, and can be a culture solution generally used for culture of an alga. Such a culture solution can be, for example, conventionally known medium such as TAP medium, HSM medium, or ATCC897 medium.

In an embodiment, accumulation of starch in a cell can be induced by cultivating the alga of the present invention in TAP medium while irradiating the alga with light in an amount of 45 $\mu E/m^2$/second. In another embodiment, accumulation of starch in a cell can be induced by cultivating the alga of the present invention in TAP medium while irradiating the alga with light in an amount of 80 $\mu E/m^2$/second.

The step of irradiating an alga with light may be carried out under a nitrogen-starved condition. The "nitrogen-starved condition" means that an alga is cultivated in a culture solution containing less than 0.001% inorganic nitrogen by weight in terms of nitrogen atoms. In a case where the step of irradiating an alga with light is carried out under a nitrogen-starved condition, for example, TAP N-free medium can be suitably used as a nitrogen-free culture solution although such a nitrogen-free culture solution is not limited to a specific one. In an embodiment, accumulation of starch in a cell can be induced by cultivating the alga of the present invention under a nitrogen-starved condition (in TAP N-free medium) while irradiating the alga with light in an amount of 80 $\mu E/m^2$/second.

As described above, according to the alga of the present invention, a photosynthate can be produced without the need for a nutrient restriction step such as a nitrogen-starved state. That is, according to the method of the present invention for producing biomass, such an embodiment is possible in which a nutrient restriction step such as a nitrogen-starved state is not substantially carried out (the method does not substantially include a nutrient restriction step such as a nitrogen-starved state). This makes it possible to simplify the procedure, thereby increasing productivity of a photosynthate.

Further, the step of irradiating an alga with light may be carried out under an autotrophic condition. The "autotrophic condition" refers to a condition in which an alga is cultivated without supply of a carbon source other than carbon dioxide. Specifically, the step of irradiating an alga with light can be carried out under an autotrophic condition by cultivating the alga of the present invention in an HSM culture solution under air ventilation and light irradiation. A source of carbon dioxide is not limited to atmosphere. For example, carbon dioxide contained in a flue of a thermal power station, ironworks, or the like can be used. This allows higher concentration of carbon dioxide than that contained in the atmosphere to be supplied to medium, thereby increasing productivity.

Under an autotrophic condition, carbon dioxide or a gas containing carbon dioxide is supplied from (allowed to pass through) the vicinity of a bottom part of a culture vessel. Diffusion speed of carbon dioxide in water is far slower than in the atmosphere. This necessitates stirring the medium. By stirring the medium, it is also possible to evenly irradiate the alga with light. Since carbon dioxide becomes an anion in water, medium with a weak buffer capacity shifts towards an acid side due to the aeration. This reduces solubility of carbon dioxide, thereby hindering carbon dioxide from being used in photosynthesis. It is therefore preferable that the medium have a buffer capacity which allows pH of the medium to be maintained near neutral or alkaline. A preferable example of such medium is conventionally known HSM medium or the like.

(2. Other Steps)

The method of the present invention for producing biomass may further include the step of collecting a photosynthate in addition to the "step of irradiating an alga with light".

According to the method of the present invention for producing biomass, for example, in a case where the photosynthate is starch, starch accumulated in a cell can be discharged to an outside of the cell as starch grains. Accordingly, in the step of collecting a photosynthate, it is only necessary to (i) separate, from the alga, the starch grains thus discharged to an outside of the cell and (ii) collect the starch grains thus separated from the alga. A method for separating, from the alga, the starch grains discharged to an outside of the cell is not limited in particular. For example, such separation is accomplished by separation means, such as spontaneous sedimentation resulting from still standing, centrifugation, or sieve, which is based on physical properties such as particles diameters and/or shapes of the starch grains and the alga cell.

The method of the present invention for producing biomass may be carried out with the use of an alga in which a glutathione concentration in a chloroplast is increased with the use of a substance that can be absorbed into the alga through contact with the alga. That is, the present invention encompasses a method for producing biomass which includes the step of cultivating an alga in the presence of a substance for increasing a glutathione concentration in a chloroplast of the alga.

Specific examples of the substance which increases a glutathione concentration in a chloroplast of an alga and which can be absorbed into the alga through contact with the alga include glutathione, glutathione conjugation, active oxygen (e.g., hydrogen peroxide), active nitrogen, polyamine, titanium oxide, jasmonic acid, salicylic acid, cysteine, cystine, heavy-metal cadmium, and an iron ion. Note that polyamine is a raw material for hydrogen peroxide. Titanium oxide generates active oxygen when it is irradiated with light. Cysteine and cystine are precursors of glutathione. Heavy-metal cadmium and an iron ion are preferably excessively administered. Especially hydrogen peroxide is preferably used from the viewpoint of cost.

The substance which increases a glutathione concentration in a chloroplast of an alga and which can be absorbed into the alga through contact with the alga is, for example, contained in a culture solution used for photosynthesis of the alga, thereby allowing the substance to make contact with the alga and to be absorbed into the alga.

According to the method of the present invention for producing biomass, biomass is produced with the use of the alga of the present invention or an alga produced by the method of the present invention for producing an alga. It is therefore possible to induce accumulation of a photosynthate in a cell of the alga by cultivating the alga without irradiating the alga with strong light nor creating a nitrogen-starved state (see Examples described later). Further, since a photosynthate accumulated in a cell of an alga can be discharged to an outside of the cell by increasing a glutathione concentration in a chloroplast, it is easy to collect the photosynthate. That is, according to the method of the present invention for producing biomass, it is possible to more easily and efficiently (i) induce accumulation of a photosynthate and (ii) collect the photosynthate, as compared with a conventional art. Consequently, according to the method of the present invention for producing biomass, it is possible to more efficiently produce biomass from an alga at lower cost, as compared with a conventional art.

The alga of the present invention may be an alga in which an expression amount and/or an activity of a protein is increased in a chloroplast, the protein being at least one protein selected from the group consisting of γ-glutamylcysteine synthetase, glutathione synthetase, ATP-sulfurylase, adenosine 5'-phosphosulfate reductase, sulfite reductase, cysteine synthetase, and serine acetyl transferase.

The alga of the present invention may be an alga into which an exogenous polynucleotide encoding a protein is introduced, the protein being at least one protein selected from the group consisting of γ-glutamylcysteine synthetase, glutathione synthetase, ATP-sulfurylase, adenosine 5'-phosphosulfate reductase, sulfite reductase, cysteine synthetase, and serine acetyl transferase.

In the alga of the present invention, the polynucleotide encoding glutamylcysteine synthetase may be selected from the group consisting of the following (a) to (d):

(a) a polynucleotide encoding a polypeptide consisting of the amino-acid sequence represented by SEQ ID NO: 1;

(b) a polynucleotide encoding a polypeptide which consists of an amino-acid sequence with deletion, substitution, or addition of one or several amino acids in the amino-acid sequence represented by SEQ ID NO: 1 and which has a γ-glutamylcysteine synthetase activity;

(c) a polynucleotide consisting of the nucleotide sequence represented by SEQ ID NO: 2; and (d) a polynucleotide which hybridizes under a stringent condition with a polynucleotide consisting of a nucleotide sequence complementary to any one of the polynucleotides (a) through (c) and which encodes a polypeptide having a γ-glutamylcysteine synthetase activity.

In the method of the present invention for producing an alga, the step of increasing a glutathione concentration may be a step of introducing, into the alga, an exogenous polynucleotide encoding a protein which is at least one protein selected from the group consisting of γ-glutamylcysteine synthetase, glutathione synthetase, ATP-sulfurylase, adenosine 5'-phospho sulfate reductase, sulfite reductase, cysteine synthetase, and serine acetyl transferase.

The method of the present invention for producing biomass may include the step of irradiating the alga with light.

In the method of the present invention for producing biomass, the step of irradiating the alga with light may be carried out under a condition where nitrogen is not substantially starved.

The present invention is not limited to the description of the embodiments above, but may be altered by a skilled person within the scope of the claims. An embodiment based on a proper combination of technical means disclosed in different embodiments is encompassed in the technical scope of the present invention.

EXAMPLES

The following more specifically describes the present invention with reference to Examples. Note, however, that the present invention is not limited to Examples.

Example 1

Production of GSH1 Overexpressing Strain

A plasmid was created in which a GSH1 gene (SEQ ID NO: 2) encoding γ-glutamylcysteine synthetase (SEQ ID NO: 1) derived from *Chlamydomonas* was ligated to a downstream of a PsaD gene promoter (PsaD promoter).

Specifically, the circular DNA, pSP124S (see Plant Journal (1998) Vol. 14(4): 441-447.), which is a vector for *Chlamydomonas*, was cleaved by concurrently treating with restriction enzymes EcoRI and EcoRV. Then, a polynucleotide (approximately 3.13 kilo-base pairs) of SEQ ID NO: 4 was ligated to the DNA thus cleaved, and the DNA was closed so as to form a circular DNA again. This circular DNA was amplified with the use of *Escherichia coli* and was then extracted and purified from *Escherichia coli* by use of a known method.

The polynucleotide represented by SEQ ID NO: 4 was produced as follows.

(1) A *Chlamydomonas reinhardtii* CC503 strain (provided from the *Chlamydomonas* Center at Duke University, USA) was cultured for four days in TAP medium at 24° C. while being irradiated with light in an amount of 50 μE/m²/second. A cDNA mixture was prepared from cells collected from a culture thus obtained, by using a cDNA synthesis kit (manufactured by Takara Bio Inc., Solid phase cDNA synthesis kit). Using this cDNA mixture as a template, PCR (annealing temperature: 58° C.) was carried out with oligonucleotide of SEQ ID NO: 5 and oligonucleotide of SEQ ID NO: 6 by a known method. A *Chlamydomonas* GSH1 gene was thus collected as a polynucleotide of approximately 2.27 kilo-base pairs in which a 3'UTR region follows ORF. Further, a terminal structure was processed by using the restriction enzyme EcoRI.

(2) A genome DNA was prepared from CC503 cells cultured and collected in a similar manner to (1) above, by using a DNA extraction kit (manufactured by NIPPON GENE CO., LTD., Isoplant). Using this genome DNA as a template, PCR (annealing temperature: 56° C.) was carried out with oligonucleotide of SEQ ID NO: 7 and oligonucleotide of SEQ ID NO: 8 by a known method. A promoter region of a *Chlamydomonas* PsaD gene was thus collected as a polynucleotide of approximately 0.86 kilo-base pairs. Further, a terminal structure was processed by using a restriction enzyme HpaI.

(3) The two kinds of polynucleotide fragments prepared in (1) and (2) above were ligated to each other with the use of a DNA ligase (produced by TOYOBO CO., LTD., Ligation High) by a known method. As a result of the above experimental operations, a polynucleotide fragment of a PsaD promoter-GSH1 gene whose one end is a blunt end and whose other end is a sticky end due to EcoRI could be prepared. In the nucleotide sequence represented by SEQ ID NO: 4, the sequence from position 853 to position 855 is a start codon, and the sequence from position 2294 to position 2296 is a stop codon. That is to say, the *Chlamydomonas* GSH1 gene has the sequence from position 853 to position 2296 of the nucleotide sequence represented by SEQ ID NO: 3 as an open reading frame (ORF).

```
                                              (SEQ ID NO: 5)
5'GCTCTCGCCTCAGGCGTT 3'

(SEQ ID NO: 6)
5'GGGGAATTCCTGAGCGAGGGCCTTACAAG 3'

(SEQ ID NO: 7)
5'ATCAGCACACACAGCAGGCTCAC 3'

(SEQ ID NO: 8)
5'TGTTAACCATTTTGGCTTGTTGTGAGTAGC 3'
```

The plasmid thus produced containing the polynucleotide of PsaD promoter-GSH1 was linearized with the use of the restriction enzyme EcoRI, and was then introduced into the *Chlamydomonas reinhardtii* CC503 strain (hereinafter referred to as "*Chlamydomonas*") by using electroporation (see Funct. Plant Biol. (2002) vol. 9: 231-241). A transformed strain (hereinafter referred to as "GSH1 overexpressing strain") in which the polynucleotide was inserted into the genome DNA and stably inherited to a younger generation along with cell replication was selected by using acquisition of bleomycin resistance by the CC503 strain as an indicator. The insertion of the plasmid DNA containing the polynucleotide into the genome DNA was confirmed by a PCR method.

Note that the PsaD gene is a gene involved in photosynthesis. Accordingly, by changing intensity of irradiation light, it is possible to regulate activity of the PsaD promoter, thereby regulating an expression amount of the GSH1 gene. That is, in a case where the GSH1 overexpressing strain is irradiated with strong light, an expression amount of exogenous GSH1 in the GSH1 overexpressing strain becomes large, whereas in a case where the GSH1 overexpressing strain is irradiated with weak light, an expression amount of exogenous GSH1 in the GSH1 overexpressing strain becomes small.

Example 2

The GSH1 overexpressing strain produced in Example 1 was cultured under a semi-heterotrophic condition with the use of tris-acetate-phosphate (TAP) medium having pH7 (see Proc. Natl. Acad. Sci. USA, 54, 1665-1669.), and a growth capacity and a starch production capacity of the GSH1 overexpressing strain were evaluated. A CC503 strain (hereinafter referred to as "parent strain (wild-type strain)") which is a wild-type *Chlamydomonas* strain was used as a control. Tables 1 and 2 show culture conditions of respective samples.

TABLE 1

| Sample | Cell type | Culture Solution | Intensity of continuous irradiation light (μE/m²/second) |
|---|---|---|---|
| 1 | GSH1 overexpressing strain | TAP medium | 45 |
| 2 | GSH1 overexpressing strain | TAP medium + 8 mM BSO | 45 |
| 3 | GSH1 overexpressing strain | TAP medium | 17 |
| 4 | GSH1 overexpressing strain | TAP medium | 80 |
| 5 | parent strain (wild-type strain) | TAP medium | 45 |
| 6 | parent strain (wild-type strain) | TAP medium + 8 mM BSO | 45 |
| 7 | parent strain (wild-type strain) | TAP medium | 17 |
| 8 | parent strain (wild-type strain) | TAP medium | 80 |

TABLE 2

| | |
|---|---|
| Intensity of continuous irradiation light (µE/m²/second) | any of 17, 45, and 80 |
| Temperature (° C.) | 24 |
| Initial blend ratio of medium amount and preculture | 95:5 |
| Medium used for preculturing | TAP medium |
| Intensity of continuous irradiation light (µE/m²/second) used for preculturing | 17 |
| Revolving speed of shaking swivel (rpm) | 120 |
| Oscillation of shaking swivel (mm) | 30 |
| Initial medium amount (mL) | 100 |
| Shape and volume (mL) of culture vessel | conical flask, 500 |

L-Buthionine-sulfoximine (abbreviated as BSO (produced by Sigma-Aldrich Corporation, Model No. B2515) added to TAP medium in Samples 2 and 6 is an inhibitor for GSH synthesis.

Figure 1:
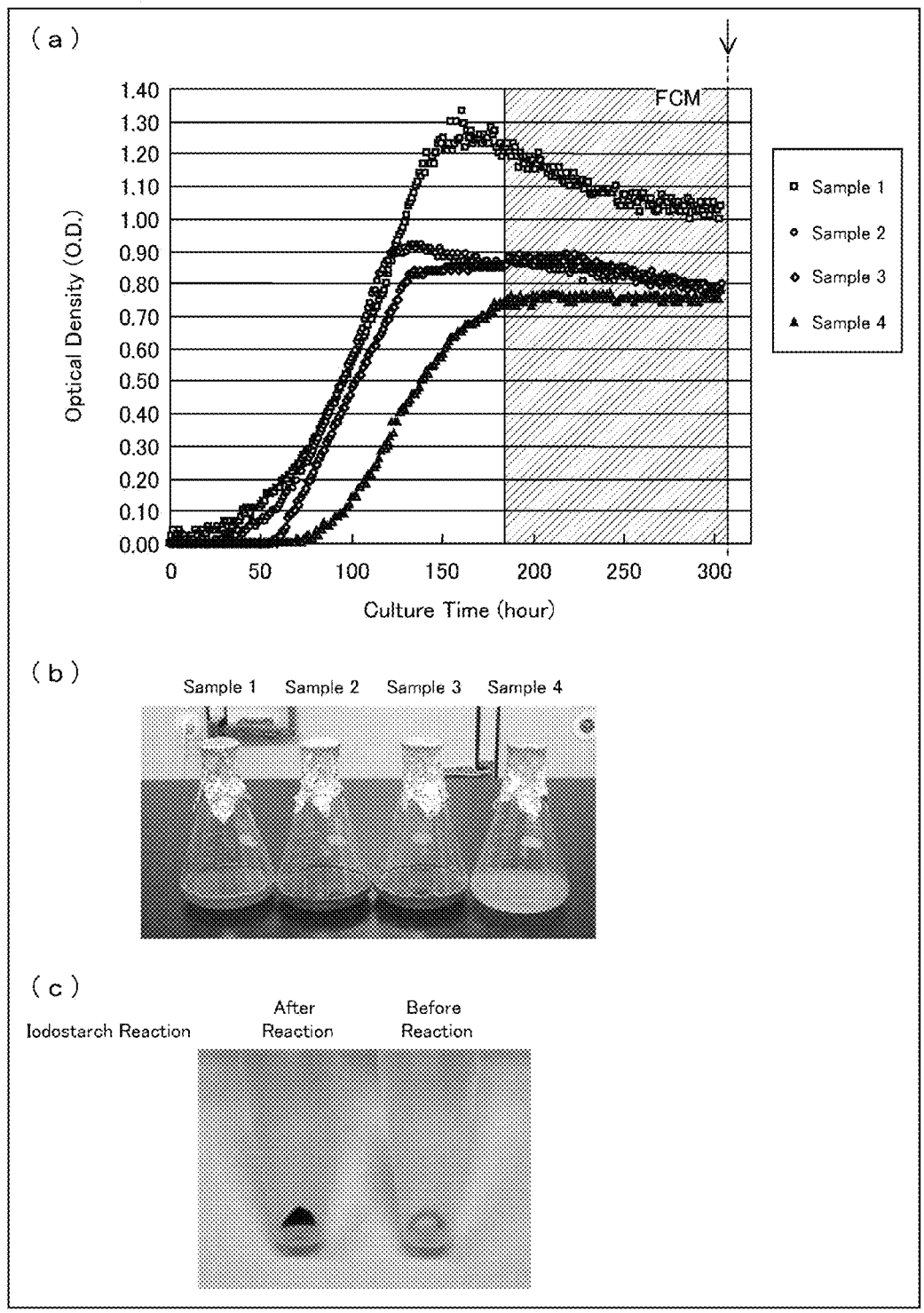
FIG. 1 shows a result of analysis of a growth capacity and a starch production capacity of the GSH1 overexpressing strain produced in Example 1, (a) of FIG. 1 is a graph showing the growth capacities of respective GSH1 overexpressing strains, (b) of FIG. 1 is a view showing states of respective culture solutions 309 hours after start of culturing, and (c) of FIG. 1 is a view showing a result of iodostarch reaction in Sample 4.
Figure 2:
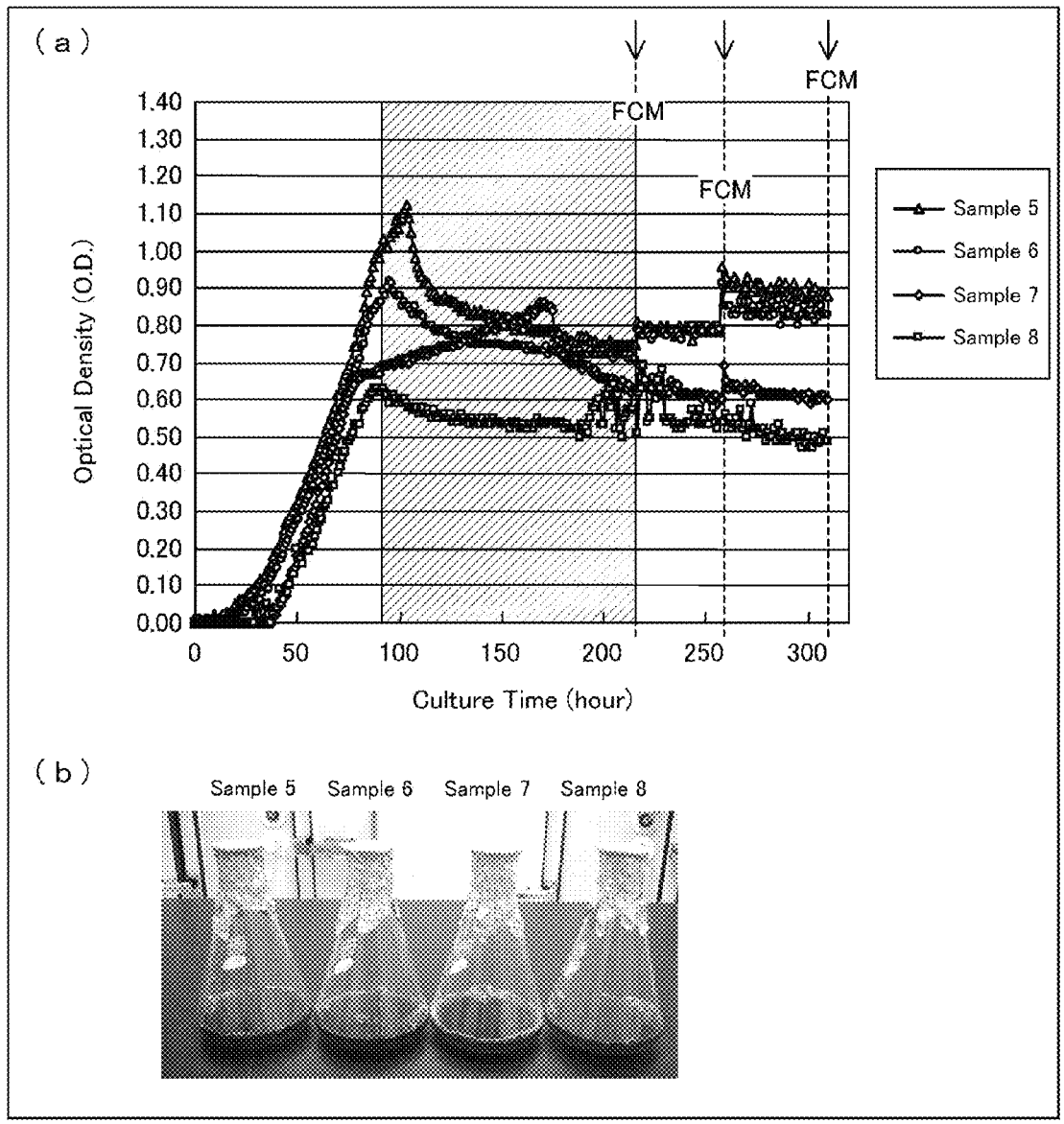
FIG. 2 shows a result of analysis of a growth capacity and a starch production capacity of a parent strain (wild-type strain), (a) of FIG. 2 is a graph showing growth capacities of respective parent strains (wild-type strains), and (b) of FIG. 2 is a view showing states of respective culture solutions 215 hours after start of culturing.

The result is shown in FIG. 1 and FIG. 2. (a) of FIG. 1 is a graph showing growth capacities of the respective GSH1 overexpressing strains, and (b) of FIG. 1 is a view showing states of respective culture solutions 309 hours after start of culturing. (a) of FIG. 2 is a graph showing growth capacities of respective parent strains (wild-type strains), and (b) of FIG. 2 is a view showing states of respective culture solutions 215 hours after start of culturing. In the graphs of (a) of FIG. 1 and (a) of FIG. 2, the vertical axis represents an optical density (OD) and the horizontal axis represents a culture time. The optical density represented by the vertical axis was measured by a device (manufactured by TAITEC CORPORATION, ODSensor-S/ODBox-A) for measuring an OD value on the basis of a transmission amount of infrared rays (950 nm). The arrows in the graphs indicate timings at which flow cytometry (FCM) was carried out.

As shown in (a) of FIG. 1, cells of Samples 1 to 4 all had a growth capacity under a semi-heterotrophic condition. Since there was no significant difference among the growth capacities of the respective samples, it was confirmed that expression of an exogenous GSH1 gene does not affect growth of *Chlamydomonas*. As shown in (b) of FIG. 1, the culture solutions became clouded in Samples 1 and 4.

Note that the "semi-heterotrophic" refers to a state in which (i) acetic acid in medium is mainly used as a carbon source and (ii), since the cells are irradiated with light and a culture flask is not sealed, carbon dioxide in the atmosphere is also used as a carbon source although it makes less contribution to growth as compared with acetic acid.

The culture solution of Sample 4 which became clouded was collected in a microtube, and a white precipitation obtained by centrifugation was subjected to iodostarch reaction. The result is shown in (c) of FIG. 1. As shown in (c) of FIG. 1, white particles collected from Sample 4 were colored bluish-violet due to the iodostarch reaction. This revealed that the white particles collected from Sample 4 were aggregations of starch. Accordingly, it was revealed that starch was produced in Samples 1 and 4 in which the culture solutions were clouded. Note that it was considered that starch produced in the GSH1 overexpressing cells was discharged to an outside of the cells as starch grains.

Meanwhile, the culture solutions of Samples 2 and 3 were not clouded. As for Sample 2 in which BSO, which is an inhibitor for GSH synthesis, was added, it was considered that starch was not discharged to an outside of the cells because BSO inhibited GSH synthesis in the GSH1 overexpressing strain of Sample 2. As for Sample 3 which was irradiated with weaker light than Samples 1 and 4, it was considered that starch sufficient to make the culture solution cloudy was not discharged to an outside of the cells because an expression amount of the exogenous GSH1 in the GSH1 overexpressing strain is smaller than that in Samples 1 and 4.

In contrast, although the cells of Samples 5 to 8 all had a growth capacity under a semi-heterotrophic condition (see (a) of FIG. 2), the culture solutions of Samples 5 to 8 did not become clouded (see (b) of FIG. 2). That is to say, in a case where the parent strains (wild-type strains) were cultured in TAP medium while being irradiated with light in an amount of 80 µE/m²/second, starch grains were not discharged to an outside of the cells.

Flow cytometry was carried out for more detailed analysis of the states of the GSH1 overexpressing strain of Sample 4 and the parent strain (wild-type strain) of Sample 8. Specifically, the cells of Samples 4 and 8 were irradiated with excitation light of 488 nm, and fluorescence intensity in the vicinity of 600 nm was measured. The fluorescence in the vicinity of 600 nm corresponds to chlorophyll fluorescence. Along with the chlorophyll fluorescence, fluorescent particles (produced by Beckman Coulter Inc., product name: Flow count) were used as an internal control for measuring a cell density. In this way, fluorescence in the range from 525 nm to 700 nm emitted by the excitation light of 488 nm was measured. Further, forward-scattered light and lateral-scattered light were measured so as to measure cell (particle) size and cell (particle) internal complexity.

Figure 3:
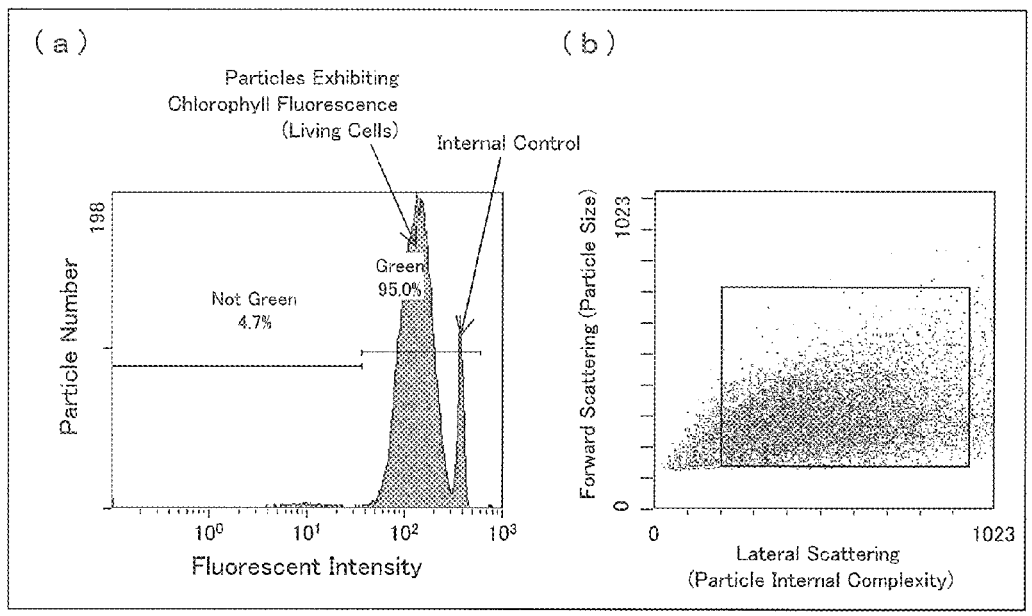
FIG. 3 shows a result of analysis of a state of the parent strain (wild-type strain) of Sample 8, (a) of FIG. 3 is a histogram for cells (particles) exhibiting chlorophyll fluorescence in the parent strain (wild-type strain) of Sample 8, and (b) of FIG. 3 is a diagram showing a correlation between (i) a size of particles floating in the culture of the parent strain (wild-type strain) of Sample 8 and (ii) complexity inside the particles.
Figure 4:
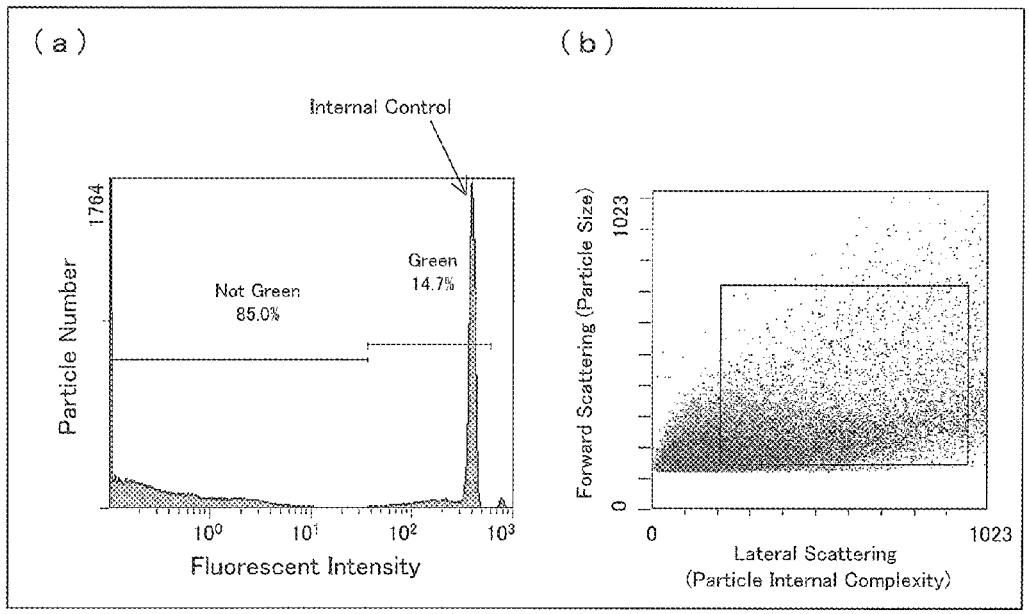
FIG. 4 shows a result of analysis of a state of the GSH1 overexpressing strain of Sample 4, (a) of FIG. 4 is a histogram for cells (particles) exhibiting chlorophyll fluorescence in the GSH1 overexpressing strain of Sample 4, and (b) of FIG. 4 is a diagram showing a correlation between (i) a size of particles floating in the culture of the GSH1 overexpressing strain of Sample 4 and (ii) complexity inside the particles.

The result is shown in FIG. 3 and FIG. 4. (a) of FIG. 3 is a histogram for cells (particles) exhibiting chlorophyll fluorescence in the parent strain (wild-type strain) of Sample 8, and (b) of FIG. 3 is a diagram showing a correlation between (i) a size of particles floating in the culture of the parent strain (wild-type strain) of Sample 8 and (ii) complexity inside the particles. (a) of FIG. 4 is a histogram for cells (particles) exhibiting chlorophyll fluorescence in the GSH1 overexpressing strain of Sample 4, and (b) of FIG. 4 is a diagram showing a correlation between (i) a size of particles floating in the culture of the GSH1 overexpressing strain of Sample 4 and (ii) complexity inside the particles. Note that each of the arrows in (a) of FIG. 3 and (a) of FIG. 4 indicates a peak of the internal control. Note also that each of the rectangular frames in (b) of FIG. 3 and (b) of FIG. 4 indicates a fraction in which a living cell exists.

As shown in (a) and (b) of FIG. 3, it was confirmed that most of the cells in the parent strain (wild-type strain) of Sample 8 were living cells having a chloroplast (chlorophyll).

Meanwhile, as shown in (a) of FIG. 4, almost no chlorophyll fluorescence was detected in the GSH1 overexpressing strain of Sample 4, and as shown in (b) of FIG. 4, not many living cells were present in the GSH1 overexpressing strain of Sample 4. In (b) of FIG. 4, particles present outside the rectangular frame were considered as starch grains discharged to an outside of the cells. That is, it was considered that starch produced in the cells of the GSH1 overexpressing strain was discharged to an outside of the cells as starch grains along with death of the cells.

Table 3 shows "density of particles which emitted chlorophyll-derived fluorescence as a result of irradiation of excitation light (488 nm)" in (a) of FIG. 3 and (a) of FIG. 4, and Table 4 shows "density of particles which did not emit chlorophyll-derived fluorescence as a result of irradiation of excitation light (488 nm)" in (a) of FIG. 3 and (a) of FIG. 4. Note that the number of cells (particles) shown in Tables 3 and 4, which is expressed by a value obtained by dividing the number of particles contained in 1 mL of the culture solution by the cube of 10, was found on the basis of the value of the internal control.

TABLE 3

|  | 45 µE/m²/sec No addition of BSO | 45 µE/m²/sec Addition of 8 mM BSO | 17 µE/m²/sec No addition of BSO | 80 µE/m²/sec No addition of BSO |
|---|---|---|---|---|
| Parent strain (wild-type strain) | 11,906 | 19,633 | 10,591 | 10,804 |
| GSH1 overexpressing strain | 1,451 | 4,228 | 2,380 | 241 |

TABLE 4

|  | 45 µE/m²/sec No addition of BSO | 45 µE/m²/sec Addition of 8 mM BSO | 17 µE/m²/sec No addition of BSO | 80 µE/m²/sec No addition of BSO |
|---|---|---|---|---|
| Parent strain (wild-type strain) | 48 | 27 | 22 | 57 |
| GSH1 overexpressing strain | 1,883 | 602 | 789 | 6,708 |

Example 3

The GSH1 overexpressing strain produced in Example 1 was cultured under a nitrogen-starved condition, and a growth capacity and a starch grain production capacity of the GSH1 overexpressing strain were evaluated. Specifically, the GSH1 overexpressing strain was cultured at 24° C. for eight days under shaking on a swivel in a TAP medium as in Example 2, while being continuously irradiated with light in an amount of 17 µE/m²/second. Subsequently, cells were collected as a precipitation by centrifugation (2000×g, five minutes) in order to change culture solutions. A half of the cells thus collected was resuspended in TAP N-free medium (medium same as the one devised by Gorman and Levine (see Proc. Natl. Acad. Sci. USA, 54, 1665-1669, except that ammonium chloride out of the composition of the TAP medium is substituted by the same amount of potassium chloride) containing no nitrogen source. The other half of the cells was resuspended in general TAP medium containing ammonium. A cell density at the time of the resuspension was adjusted to be approximately 1.1 times that at the end of the preculturing using the TAP medium. That is, cells contained in 90 mL of the preculture were resuspended in 100 mL of fresh medium. The cells were cultured under shaking on a swivel while being irradiated with light in an amount of 80 µE/m²/second, and part of the culture was separated every day so as to evaluate a growth capacity and a starch production capacity. A parent strain (wild-type strain, CC503 strain) was used as a control. Tables 5 and 6 show culture conditions for respective samples.

TABLE 5

| Sample | Cell type | Culture Solution |
|---|---|---|
| 9 | GSH1 overexpressing strain | TAP medium (N-containing) |
| 10 | GSH1 overexpressing strain | TAP N-free medium |
| 11 | Parent strain (wild-type strain) | TAP medium (N-containing) |
| 12 | Parent strain (wild-type strain) | TAP N-free medium |

TABLE 6

| Intensity of continuous irradiation light (µE/m²/second) | 80 |
|---|---|
| Temperature (° C.) | 24 |
| Revolving speed of shaking swivel (rpm) | 120 |
| Oscillation of shaking swivel (mm) | 30 |
| Initial medium amount (mL) | 100 |
| Shape and volume (mL) of culture vessel | conical flask, 300 |

The result is shown in FIG. 5 and FIG. 6. FIG. 5 is a graph showing (i) a time-course for "density of cells (particles) that exhibit chlorophyll fluorescence" and (ii) a time-course for "density of cells (particles) that do not exhibit chlorophyll fluorescence" in Samples 9 and 10. FIG. 6 is a graph showing (i) a time-course for "density of cells (particles) that exhibit chlorophyll fluorescence" and (ii) a time-course for "density of cells (particles) that do not exhibit chlorophyll fluorescence" in Samples 11 and 12. In the graphs of FIG. 5 and FIG. 6, the vertical axis represents a density of cells (particles), and the horizontal axis represents a culture time. In FIG. 5 and FIG. 6, the time at which the change of the culture solutions took place is set to culture time 0. In FIG. 5 and FIG. 6, the "density of cells (particles) that do not exhibit chlorophyll fluorescence" corresponds to "density of starch grains". In (b) and (c) of FIGS. 5 and 6, "TAP normal" and "TAP N-free" in the legend represent "TAP medium containing a nitrogen source" and "TAP medium containing no nitrogen source", respectively.

As shown in (a) of FIG. 5, as for the GSH1 overexpressing strain cultured in the culture solution containing a nitrogen source, a density of cells having chloroplasts had a tendency to once increase after start of culturing and then decline. Meanwhile, as for the GSH1 overexpressing strain cultured in the culture solution containing no nitrogen source, cells having chloroplasts hardly proliferated. A density of starch grains increased over time regardless of whether a nitrogen source is present or absent in a culture solution. Further, the density of starch grains had a tendency to increase as the density of cells (cells having chloroplasts) in the culture solution declines.

Meanwhile, as shown in (a) of FIG. 6, cells of the parent strain (wild-type strain) proliferated in the culture solution containing a nitrogen source, but cells of the parent strain (wild-type strain) gradually proliferated in the culture solution containing no nitrogen source. Further, a density of starch grains in the parent strain (wild-type strain) did not increase regardless of presence/absence of a nitrogen source in the culture solution. Although it is reported that accumulation of starch occurs in the parent strain (wild-type strain) under a nitrogen-starved condition, starch grains are normally not discharged to an outside of cells even under a nitrogen-starved condition at the light intensity (80 µE/m²/second) for Chlamydomonas culturing. Also in a case where the parent strain (wild-type strain) was irradiated with light in an amount of 250 µE/m²/second, starch grains were not discharged to an outside of cells although the result is not shown.

Starch contained in fractions separated from the culture solutions of Samples 9, 10, 11, and 12 at intervals of 1 day or 2 days was quantified. The quantification was carried out with the use of Glucose Test Wako (produced by Wako Pure Chemical Industries, Ltd.). The result is shown in (b) and (c) of FIG. 5 and (b) and (c) of FIG. 6.

As shown in (b) of FIG. 5 and (b) of FIG. 6, under a nitrogen-starved condition, both of (i) a starch concentration in the culture solution for the GSH1 overexpressing strain and (ii) a starch concentration in the culture solution for the parent strain (wild-type strain) increased. Meanwhile, under a condition where nitrogen is not starved (TAP (N-containing)

medium), the starch concentration in the medium for the parent strain (wild-type strain) hardly increased, but the starch concentration in the medium for the GSH1 overexpressing strain increased as in the case of the nitrogen-starved condition.

(c) of FIG. 5 and (c) of FIG. 6 each show an amount of starch contained in the culture solution per one million cells having chloroplasts. As shown in (c) of FIG. 5 and (c) of FIG. 6, productivity per cells of the GSH1 overexpressing strain remarkably increased as compared with the parent strain (wild-type strain) regardless of whether the culturing was carried out under a nitrogen-starved condition or a condition where nitrogen is not starved. This means that (i) the GSH1 overexpressing strain is better, in starch accumulation yield relative to a medium component which is one of raw materials, than the parent strain (wild-type strain), (ii) the GSH1 overexpressing strain is lower in amount of waste made up of cell components than the parent strain (wild-type strain), and (iii) the GSH1 overexpressing strain is easier in purification of starch than the parent strain (wild-type strain). Moreover, the increased productivity per cell is very advantageous for proceeding the cells from a cell growth stage to a production stage since the increased productivity per cell makes it easy to increase a cell density.

FIG. 19 and FIG. 20 show results of multiple-independent experiments that are carried out in the same manner as those of FIG. 5 and FIG. 6 respectively. FIG. 19 is a graph showing (i) a time-course for "density of cells (particles) that exhibit chlorophyll fluorescence" and (ii) a time-course for "density of cells (particles) that do not exhibit chlorophyll fluorescence" in Samples 9 and 10, as in FIG. 5. FIG. 20 is a graph showing (i) a time-course for "density of cells (particles) that exhibit chlorophyll fluorescence" and (ii) a time-course for "density of cells (particles) that do not exhibit chlorophyll fluorescence" in Samples 11 and 12, as in FIG. 6. As shown in FIG. 19 and FIG. 20, the results obtained by carrying out the same multiple-experiments as those of FIG. 5 and FIG. 6 showed the same tendencies as those shown in FIG. 5 and FIG. 6. It was thus confirmed that data reproducibility is high.

Example 4

The GSH1 overexpressing strain produced in Example 1 was cultured under an autotrophic condition, and a growth capacity and a starch grain production capacity of the GSH1 overexpressing strain were evaluated. Specifically, the GSH1 overexpressing strain was precultured in TAP medium, and was then passaged in HSM medium (see Proc. Natl. Acad. Sci. USA (1960) 46, 83-91.). In the HSM medium, the GSH1 overexpressing strain was irradiated with light while being supplied with sterile air via a glass tube inserted into a vicinity of a culture vessel. A magnetic stirrer was used to stir a culture solution. Table 7 shows culture conditions in detail. A parent strain (wild-type strain) was cultured as a control under the same conditions, and a growth capacity and a starch grain production capacity the parent strain (wild-type strain) were evaluated.

TABLE 7

| | |
|---|---|
| Intensity of continuous irradiation light ($\mu E/m^2$/second) | 80 |
| Temperature (° C.) | 24 |
| Initial Blend ratio of culture amount and preculture | 12:1 |

TABLE 7-continued

| | |
|---|---|
| Medium used for preculturing | TAP medium |
| Intensity of continuous irradiation light ($\mu E/m^2$/second) used for preculturing | 17 |
| Aeration amount (L/min) | 1 to 2 |
| Initial Medium amount (mL) | 325 |
| Shape and volume (mL) of culture vessel | cylindrical media bottle, 500 |

In order to maintain a medium amount, which declines due to transpiration caused by the aeration, at approximately 300 mL, sterile water was timely supplied.

The result is shown in FIG. 7. (a) of FIG. 7 is a graph showing (i) a time-course for "density of cells (particles) that exhibit chlorophyll fluorescence" and (ii) a time-course for "density of cells (particles) that do not exhibit chlorophyll fluorescence" in the GSH1 overexpressing strain and the parent strain (wild-type strain). (b) of FIG. 7 is a graph showing a time-course for a starch amount per culture solution. In (a) of FIG. 7, the vertical axis represents a cell (particle) density, and the horizontal axis represents a culture time. In (a) of FIG. 7, the time at which the culture under an autotrophic condition started is set to culture time 0. In (a) of FIG. 7, the "density of cells (particles) that do not exhibit chlorophyll fluorescence" corresponds to "density of starch grains".

As shown in (a) of FIG. 7, the cell density in the GSH1 overexpressing strain increased over time although the rate of increase was lower than the parent strain (wild-type strain). Further, the density of starch grains in the GSH1 overexpressing strain had a tendency to linearly increase over time as the cell density increased. Meanwhile, in the wild-type strain, the cell density increased, but starch grains were hardly discharged to an outside of the cells.

Further, on the tenth day after start of the culture under the autotrophic condition, iodostarch reaction for the GSH1 overexpressing strain and for the parent strain (wild-type strain) was carried out. Specifically, cells (particles) were collected from 1 mL of the culture solution for the GSH1 overexpressing strain after centrifugation. Similarly, cells (particles) were collected from the culture solution for the parent strain (wild-type strain). The cells (particles) thus collected were treated with the use of acetone to remove chlorophyll from the cells, and then iodostarch reaction was carried out. The removal of chlorophyll was for better viewing of results of the iodostarch reaction.

The result is shown in FIG. 8. FIG. 8 is a view showing the result of the iodostarch reaction in the GSH1 overexpressing strain and the parent strain (wild-type strain). As shown in FIG. 8, in the GSH1 overexpressing strain, white particles were colored dark bluish-violet due to the iodostarch reaction. It was thus confirmed that starch grains were discharged to an outside of the cells in the GSH1 overexpressing strain. Also in the parent strain (wild-type strain), slight iodostarch reaction was observed although coloring is weak. This result suggested that, even under a condition where nitrogen is not starved, a certain amount of starch is produced also in the parent strain (wild-type strain) under an autotrophic condition.

Starch contained in 1 mL of a sample separated every day from the culture solution for the culture under the autotrophic condition shown in (a) of FIG. 7 was quantified. Glucose Test Wako (produced by Wako Pure Chemical Industries, Ltd.) was used to quantify the starch.

The result is shown in (b) of FIG. 7. Start of starch production of the GSH1 overexpressing strain was earlier than that of the parent strain (wild-type strain). Further, a production amount of starch in the GSH1 overexpressing strain was larger than that in the parent strain (wild-type strain) cultured for the same period of time. For example, on the tenth day after start of culture, starch concentration in the culture solution for the GSH1 overexpressing strain was 416.8 mg per 1 L of the culture solution, and starch concentration in the culture solution for the parent strain (wild-type strain) was 196.4 mg per 1 L of the culture solution. That is, productivity per culture solution in the GSH1 overexpressing strain was not less than two times as high as that in the parent strain (wild-type strain). This means that (i) the GSH1 overexpressing strain is better, in starch accumulation yield relative to a medium component which is one of raw materials, than the parent strain (wild-type strain), (ii) an amount of waste made up of cell components in the GSH1 overexpressing strain is lower than that in the parent strain (wild-type strain), and (iii) purification of starch of the GSH1 overexpressing strain is easier than that of the parent strain (wild-type strain). Moreover, the result of the example shown in (a) and (b) of FIG. 7 suggests that the GSH1 overexpressing strain, in which a cell growth amount was suppressed relative to a production amount of starch, is a strain which can more effectively utilize a medium component than the parent strain (wild-type strain) and is therefore preferable, to the parent strain (wild-type strain), as a cell strain for continuous starch production utilizing photosynthesis.

Example 5

The GSH1 overexpressing strain produced in Example 1 was inoculated into 100 mL of TAP medium, and was cultured while being continuously irradiated with light in an amount of 80 µE/m²/second. An OD value was continuously monitored on the basis of a transmission amount of infrared rays (950 nm). Further, 5 mL of a culture solution was separated in a logarithmic growth phase or a stationary phase. The culture solution thus separated was transplanted (passaged) into 100 mL of fresh TAP medium and the culture was continued in a similar manner.

FIG. 9 is a view showing a result of analysis of a growth capacity of the GSH1 overexpressing strain. The arrows in FIG. 9 indicate timings at which the culture solution was separated. In FIG. 9, "PRIMARY" means "primary culture", "SUBCULTURE 1" means the first-passaged culture from the primary culture, "SUBCULTURE 2" means the second-passaged culture from the primary culture, "SUBCULTURE 3" means the third-passaged culture from the primary culture, and "SUBCULTURE 4" means the fourth-passaged culture from the primary culture.

As shown in FIG. 9, it was confirmed that the GSH1 overexpressing strain was capable of newly proliferating as a seed culture not only in the logarithmic growth phase, but also approximately 150 hours after entry into the stationary phase. An approximate line of the primary culture (PRIMARY) in an exponential growth interval was expressed by $y=0.0067x-0.4287$ and $R^2$ was 0.9959. An approximate line of the first-passaged culture (SUBCULTURE 1) in an exponential growth interval was expressed by $y=0.0085x-1.774$ and $R^2$ was 0.9952.

However, in a case where a culture obtained approximately 150 hours after entry into the stationary phase was used as a seed, rising of growth was approximately 18 hours later than a case where a culture obtained immediately after entry into the stationary phase was used as a seed. This result revealed that not all the cells of the GSH1 overexpressing strain are destined to die by the end of the logarithmic growth phase, but some cells still have a growth capacity even at the end of the logarithmic growth phase. That is, the result revealed that repeated-batch cultivation can be carried out by using, as seeds, cells of the GSH1 overexpressing strain in the logarithmic growth phase and cells of the GSH1 overexpressing strain in the stationary phase.

FIG. 10 shows a result of more detailed analysis of characteristics of the GSH1 overexpressing strain in each growth phase. FIG. 10 shows a result of analysis of states of the GSH1 overexpressing strain at respective time points for passaging, (a) of FIG. 10 is a view showing a correlation between cell size and cell internal complexity in the GSH1 overexpressing strain during the "SUBCULTURE 1" shown in FIG. 9, (b) of FIG. 10 is a view showing a correlation between cell size and cell internal complexity in the GSH1 overexpressing strain during the "SUBCULTURE 2" shown in FIG. 9, and (c) of FIG. 10 is a view showing a correlation between cell size and cell internal complexity in the GSH1 overexpressing strain during the "SUBCULTURE 3" shown in FIG. 9.

As shown in FIG. 10, it was confirmed that the GSH1 overexpressing strain discharged starch grains in any culture phases (the logarithmic growth phase and the stationary phase). In (a) through (c) of FIG. 10 each of which shows a correlation between forward scattering and lateral scattering, a group of particles at the lower left corner corresponds to starch grains. It was confirmed from (a) through (c) of FIG. 10 that plenty of starch grains were contained. The result revealed that the GSH1 overexpressing strain discharged starch grains even in the logarithmic growth phase.

Example 6

A shape of starch grains discharged into an outside of cells of the GSH1 overexpressing strain produced in Example 1 was observed. Specifically, starch grains discharged to an outside of the cells were suspended in 1 mL of 0.01% Tween20 (Registered Trademark, produced by Sigma Corporation, Model No. P1379), dispersed after addition of 9 mL of Percoll (Registered Trademark, produced by Sigma Corporation, Model No. P1644), and purified by centrifugation (9100×g, 30 minutes). The starch grains thus obtained were observed with the use of a scanning electron microscope.

FIG. 11 is a view showing a result of observation of a shape of starch grains discharged to an outside of the cells from the GSH1 overexpressing strain. (a) of FIG. 11 is a view showing a result of observation of starch grains with the use of a scanning electron microscope. As shown in (a) of FIG. 11, it was confirmed that the starch grains produced by the GSH1 overexpressing strain were extremely small particles of uniform sizes whose average particle diameter of the major axis was 1.3 µm (standard deviation 0.181) and whose average particle diameter of the manor axis was 1.0 µm (standard deviation 0.204). General starch grains produced by corn, potato, wheat, or the like are 10 µm to 50 µm in average particle diameter. This tells how small the starch grains produced by the GSH1 overexpressing strain are.

As described above, the starch grains produced by the GSH1 overexpressing strain are smaller than general starch grains produced by corn, potato, wheat, or the like. Such extremely small starch grains are useful for production of medicines.

The discharge of the starch grains from the GSH1 overexpressing strain is discharge accompanying rupture of cells. Although autolysis occurs almost simultaneously with the rupture of cells, starch grains themselves are not digested by an enzyme which causes the autolysis. Accordingly, starch grains with fewer impurities are obtained in the GSH1 overexpressing strain.

Specifically, in a case where autolysis of cells does not occur, it is necessary to carry out a step of breaking the cells by chemical or physical means such as grinding in order to extract starch grains accumulated in the cells. Moreover, fragments of broken cells mix in starch grains as residues. Meanwhile, in a case where autolysis of cells occurs, macromolecules such as protein, carbohydrate, and membrane system are degraded into lower-molecular substances due to enzyme reaction. As a result, an amount of fragments of cells becomes smaller. Further, since the cells hardly remain, starch grain production efficiency per raw material (per medium component) is high. This means that yield is high. The low-molecular substances generated by the autolysis are considered as being available for growth of an alga. Such recycling of the substances can be expected to lead to saving of medium necessary for growth of the alga. Autolysis of cells does not occur in the wild-type strain, and occurs only in the GSH1 overexpressing strain.

(b) of FIG. 11 is a view showing a result of iodostarch reaction of a starch grain discharged from the GSH1 overexpressing strain. As shown in (b) of FIG. 11, it was confirmed that the starch grain discharged from the GSH1 overexpressing strain was colored bluish-purple due to the iodostarch reaction just like corn starch used as a comparison.

(c) of FIG. 11 is a view showing a starch production capacity of the GSH1 overexpressing strain in a case where BSO, which is an inhibitor for GSH synthesis, was added. It was confirmed that (i) in the GSH1 overexpressing strain to which BSO was not added, starch was discharged into an outside of cells since synthesis of GSH was not inhibited, and (ii) in the GSH1 overexpressing strain to which BSO was added, starch was not discharged into an outside of the cells since synthesis of GSH was inhibited.

Example 7

An oil and fat production capacity of the GSH1 overexpressing strain was examined. Specifically, the GSH1 overexpressing strain produced in Example 1 was precultured in 200 mL of TAP medium (containing a nitrogen source) for four days while being continuously irradiated with light in an amount of 17 $\mu E/m^2$/second. Then, cells contained in 90 mL of a culture thus obtained were collected by centrifugation (2000×g, 5 minutes), and the cells thus collected were resuspended in fresh nitrogen-source-containing TAP medium (100 mL) or fresh nitrogen-source-free TAP medium (100 mL), thereby exchanging medium. Subsequently, the cells were cultured for six days while being continuously irradiated with light in an amount of 80 $\mu E/m^2$/second. Cells obtained at the end of the preculture and cells obtained on the sixth day after the medium change were stained with nile red, and the cells thus stained were subjected to flow cytometry.

The same experiment was carried out by using, as a control, a *Chlamydomonas reinhardtii* CC503 strain (wild-type strain), which is a parent strain of the GSH1 overexpressing strain.

FIG. 12 shows a result of analysis of an oil and fat production capacity of the GSH1 overexpressing strain, (a) of FIG. 12 is a histogram for cells that exhibit nile-red-derived fluorescence in the parent strain (wild-type strain), (b) of FIG. 12 is a histogram for cells that exhibit nile-red-derived fluorescence in the GSH1 overexpressing strain, (c) of FIG. 12 is a view showing a result of observation, using a confocal laser microscope, of the nile-red stained parent strain (wild-type strain) contained in the preculture, and (d) of FIG. 12 is a view showing a result of observation, using a confocal laser microscope, of the nile-red stained GSH1 overexpressing strain contained in the preculture. In each of the upper histograms in (a) and (b) of FIG. 12, the light gray peak corresponds to cells cultured in the nitrogen-source-containing TAP medium, the white peak corresponds to cells cultured in the nitrogen-source-free TAP medium, and the rightmost peak (peak with the highest fluorescent intensity) corresponds to artificial fluorescent beads (internal control) added to determine a particle density. Each of the lower histograms in (a) and (b) of FIG. 12 corresponds to nile-red stained cells contained in the preculture.

As shown in FIG. 12, all of the three culture samples of the GSH1 overexpressing strain showed an increased fluorescent intensity per cell as compared with those of the parent strain. The three culture samples are (i) a culture sample cultured for four days in the preculture (containing a nitrogen source), (ii) a culture sample obtained on the sixth day after the change to the nitrogen-source-containing medium, and (iii) a culture sample obtained on the sixth day after the change to the nitrogen-source-free medium. This result shows that the GSH1 overexpressing strain is larger in amount of oils and fats contained in individual cells than the parent strain (wild-type strain). Specifically, the fluorescent intensity of the nile-red-derived fluorescence in the GSH1 overexpressing strain was approximately the 0.5th power of 10 (about 3.2) times higher than that in the parent strain (wild-type strain).

FIG. 13 shows a result of analysis of a state of the GSH1 overexpressing strain, (a) of FIG. 13 is a view showing a correlation between cell size and cell internal complexity in the GSH1 overexpressing strain, (b) of FIG. 13 is a view showing a correlation between cell size and fluorescent intensity of the nile-red-derived fluorescence in the GSH1 overexpressing strain, (c) of FIG. 13 is a view showing a correlation between cell size and cell internal complexity as to cells contained in the rectangular region in (b) of FIG. 13, and (d) of FIG. 13 is a view showing a correlation between cell size and cell internal complexity in the parent strain (wild-type strain).

As a result of a gating on a group of particles emitting strong fluorescence in (b) of FIG. 13 (particles in the rectangular region in (b) of FIG. 13), it was revealed that the cells emitted strong light, as shown in (c) of FIG. 13. Meanwhile, it was revealed that extremely small particles (i.e., extremely small particle group which the starch grains belong to) detached from the cells did not emit light. It was thus confirmed that fine particles made up of oils and fats are not included in a group of fine particles which exhibit the same level of forward scattering as the starch grains and the same level of lateral scattering as the starch grains.

Note that strong emission of nile-red-derived fluorescence occurs in a case where cells preserve their forms. In a case where cells are broken and oils and fats contained therein leave the cells, nile-red-derived fluorescence cannot be detected (is hard to detect) by a flow cytometer (FCM). This suggested a possibility that a difference in oil and fat amount between the GSH1 overexpressing strain and the parent strain (wild-type strain) is estimated to be lower than an actual value as the disruption of cells in the GSH1 overexpressing strain progresses.

In view of this, fatty acids were extracted from the cells of the GSH1 overexpressing strain and the cells of the parent strain (wild-type strain) and were then quantitatively analyzed in order to clarify a difference in oil and fat amount between the GSH1 overexpressing strain and the parent strain (wild-type strain). Specifically, fatty acids produced by the GSH1 overexpressing strain were collected from the same cells as those subjected to the flow cytometry (cells obtained by culturing a GSH1 overproduction strain in the nitrogensource-containing TAP medium or the nitrogen-source-free TAP medium for six days under continuous application of light in an amount of 80 µE/m$^2$/second) by a method developed by Bligh and Dyer (see Can. J. Biochem. Physiol. 37(8): 911-917.), and the fatty acids thus collected were methyl esterified, and then subjected to gas chromatograph mass spectrometry (GC/MS). In the GC/MS, pentadecanoic acid was added as an internal control. An equal amount of pentadecanoic acid was added to all the samples. The same experiment was carried out by using, as a control, a *Chlamydomonas reinhardtii* CC503 strain (wild-type strain) which is a parent strain of the GSH1 overexpressing strain.

Specifically, the following four samples were analyzed with the GC/MS:

(i) a parent strain (wild-type strain) cultured in the presence of nitrogen, (ii) a parent strain (wild-type strain) cultured under a nitrogen-starved condition, (iii) a GSH1 overexpressing strain cultured in the presence of nitrogen, and (iv) a GSH1 overexpressing strain cultured under a nitrogen-starved condition.

Note that the following commercially-available products were used as fatty acid standards: pentadecanoic acid (produced by GL Sciences Inc., Model No. 1021-43150), palmitic acid (produced by Sigma Corporation, Model No. P0500), palmitoleic acid (produced by Sigma Corporation, Model No. P9417), stearic acid (produced by Sigma Corporation, Model No. S4751), oleic acid (produced by Sigma Corporation, Model No. O1008), linoleic acid (produced by Sigma Corporation, Model No. L1376), and linolenic acid (produced by Sigma Corporation, Model No. L2376).

FIG. 14 is a view showing a result of the gas chromatograph mass spectrometry. As shown in FIG. 14, a peak corresponding to palmitic acid ($C_{16:0}$), which is one of the standards, was observed in all the samples. As a result, it was confirmed that palmitic acid is produced as a fatty acid in the parent strain (wild-type strain) and the GSH1 overexpressing strain.

Table 8 shows a result of quantification of an amount of oils and fats contained in the parent strain (wild-type strain) and an amount of oils and fats contained in the GSH1 overexpressing strain.

TABLE 8

| Cell strain | Nitrogen source | µg/mL culture solution | µg/million cells |
|---|---|---|---|
| Parent strain (wild-type strain) | Present | 4.7 | 0.3 |
| | Absent | 14.3 | 1.0 |
| GSH1 overexpressing strain | Present | 3.9 | 2.6 |
| | Absent | 5.4 | 5.0 |

As shown in Table 8, it was confirmed that an amount of oils and fats per one million cells in the GSH1 overexpressing strain was not less than five times higher than that in the parent strain (wild-type strain). It was thus confirmed that an amount of oils and fats contained in a cell of an alga is increased by increasing a glutathione concentration in a chloroplast of the alga.

Example 8

It is reported that a *Chlamydomonas reinhardtii* sta6-deficient mutant strain (referred to also as "sta6 mutant strain") contains a larger amount of oils and fats than a wild-type (*Chlamydomonas reinhardtii* STA6) strain. It is also reported that staining oil bodies, which are storages for intracellular oils and fats, with nile red revealed that the sta6 mutant strain contains more and larger oil bodies than a wild-type strain (see Wang et al. (2009) Eukaryotic Cell Vol. 8 (12): 1856-1868. (Non-Patent Literature 1)).

In view of this, a GSH1 overexpressing strain was produced by using the sta6-deficient mutant strain as a parent strain. Specifically, the GSH1 overexpressing strain (referred to as "GSH1 overexpressing strain (sta6$^-$ background)" was produced in the same method as that used in Example 1 except for that a CC4333 strain (provided from the *Chlamydomonas* Center at Duke University, USA), which is a sta6 mutant strain, was used instead of the *Chlamydomonas reinhardtii* CC503 strain.

FIG. 15 shows a result of analysis of a state of the GSH1 overexpressing strain (sta6$^-$ background) and a state of the parent strain (sta6$^-$). (a) of FIG. 15 is a view showing a correlation between cell size and cell internal complexity in the parent strain (sta6$^-$), and (b) of FIG. 15 is a view showing a correlation between cell size and cell internal complexity in the GSH1 overexpressing strain (sta6$^-$ background).

As shown in FIG. 15, as for the correlation between forward scattering and lateral scattering, no difference could be recognized between the GSH1 overexpressing strain (sta6$^-$ background) and the parent strain (sta6$^-$). This means that, as long as the analysis using flow cytometry could tell, no difference could be recognized in cell size and intracellular structure between the GSH1 overexpressing strain (sta6$^-$ background) and the parent strain (sta6$^-$).

Next, the GSH1 overexpressing strain (sta6$^-$ background) was inoculated into 100 mL of TAP medium and precultured for five days while being continuously irradiated with light in an amount of 17 µE/m$^2$/second. Then, cells contained in 90 mL of a culture thus obtained were collected by centrifugation (2000×g, five minutes). The cells thus collected were resuspended in 90 mL of fresh nitrogen-source-containing TAP medium or fresh nitrogen-source-free TAP medium, thereby carrying out medium change. Then, the cells were further cultured for three days while being continuously irradiated with light in an amount of 80 µE/m$^2$/second. Cells obtained at the end of the preculture and cells obtained on the third day after the medium change were stained with nile red, and the cells thus stained were subjected to flow cytometry. The same experiment was carried out by using, as a control, a stab mutant strain (CC4333 strain, sta6$^-$), which is a parent strain of the GSH1 overexpressing strain (sta6$^-$ background).

FIG. 16 shows a result of analysis of (i) oil and fats production capacities of the GSH1 overexpressing strain (sta6$^-$ background) and of the parent strain (sta6$^-$) at the end of the preculture and (ii) oil and fats production capacities of the GSH1 overexpressing strain (sta6$^-$ background) and of the parent strain (sta6$^-$) on the third day after the medium change. (a) of FIG. 16 is a histogram for cells exhibiting nile-red-derived fluorescence in the GSH1 overexpressing strain (sta6$^-$ background) and the parent strain (sta6$^-$) at the end of the preculture, and (b) of FIG. 16 is a histogram for cells exhibiting nile-red-derived fluorescence in the GSH1 overexpressing strain (sta6$^-$ background) and the parent strain (sta6$^-$) on the third day after the medium change. Note that, in (a) and (b) of FIG. 16, a result of the parent strain (sta6$^-$) is shown by the dark gray histogram and a result of the GSH1 overexpressing strain (sta6$^-$ background) is shown by the light gray histogram.

As shown in (b) of FIG. 16, the GSH1 overexpressing strain (sta6$^-$ background) on the third day after the medium change reveals a distribution of fluorescent intensities that is shifted towards the higher-intensity side (rightside), as compared with the parent strain (sta6⁻). This shows that the GSH1 overexpressing strain (sta6⁻ background) contains a larger amount of oils and fats in its cells as compared with the parent strain (sta6⁻).

It was confirmed from the results that an amount of oils and fats contained in cells of an alga is increased by increasing a glutathione concentration in chloroplasts of the alga.

Example 9

The GSH1 overexpressing strain produced in Example 1 was inoculated in tris-acetate-phosphate (TAP) medium of pH7 (see Proc. Natl. Acad. Sci. USA, 54, 1665-1669.), and was then cultured under a semi-heterotrophic condition in a culture chamber at 24° C. while being shaken and continuously irradiated with light in an amount of 100 μE/m²/second. Cells contained in 1 mL of a culture thus obtained were collected every other day, and chlorophyll a and chlorophyll b were extracted from the cells with the use of a solvent containing 80% acetone and 20% water. Absorbance at the wavelength of 645 nm and absorbance at the wavelength of 663 nm were measured with the use of a spectrophotometer, and an amount of chlorophyll a and an amount of chlorophyll b were calculated from these values by using the calculation formula advocated by Porra et al. (see Biochim. Biophys. Acta (1989), Vol. 975, 384-394).

FIG. 17 shows a result of analysis of a chlorophyll amount of the GSH1 overexpressing strain produced in Example 1. As shown in FIG. 17, a total chlorophyll amount (sum of a chlorophyll a amount and a chlorophyll b amount) increased along with growth of cells from the fourth day to the tenth day of culture, but declined thereafter mainly due to degradation of the chlorophyll a. On the tenth day of culture, the total chlorophyll amount reached a maximum value of 3.8 μg per 1 mL of a culture solution, which value is smaller than a total chlorophyll amount (7.6 μg/mL) of the parent strain (wild-type strain). That is, a total chlorophyll amount per culture solution in the GSH1 overexpressing strain is smaller than that in the parent strain (wild-type strain) throughout the entire culture period.

It can be said that as a total chlorophyll amount per culture solution becomes smaller, an optical energy loss resulting from excessive light absorption by an alga body becomes smaller. In other words, it can be said that in a case where two strains are subjected to liquid culture under the same amount of light, one having a smaller total chlorophyll amount per culture solution allows optical energy to be transmitted deeper in the culture. There are reports about researches aiming to reduce a chlorophyll antenna size of a photosystem 2 by reducing an amount of chlorophyll b (see Tanaka et al. (1998) Proc. Natl. Acad. Sci. USA Vol. 95, 12719-12723 and Polle et al. (2000) Planta Vol. 211, 335-344). An operation of reducing an amount of chlorophyll b also has an effect of transmitting optical energy deeper in a culture.

It is suggested that a change in total amount and composition ratio of pigments associated with photosynthesis contributes to an increase in productivity of a photosynthate.

As shown in FIG. 17, a total amount and a composition ratio of pigments can be changed by overexpression of GSH1. This suggests that the overexpression of GSH1 contributes to an increase in productivity of a photosynthate.

Example 10

A recombinant DNA molecule was created through the following procedure for the purpose of expressing gshA, which is an *Escherichia coli*-derived γ-glutamylcysteine synthetase gene, in *Cyanobacteria Synechococcus*.

(1) A recognition site for the restriction enzyme SmaI was made by substituting the 3700th base (adenine) of an *Escherichia coli* vector pACYC187 (produced by NIPPON GENE CO., LTD., Model No. 313-02201, SEQ ID NO: 9) with cytosine. Subsequently, this vector was treated with two kinds of restrictions enzymes SmaI and SalI so as to prepare a DNA fragment of approximately 2.7 kb containing a chloramphenicol-resistant gene and a replication origin (p15A ori).

(2) A DNA fragment (SEQ ID NO: 10) of approximately 1.6 kb containing a gshA gene was prepared by a PCR method using, as a template, a genome DNA of an *Escherichia coli* JM109 strain and using two kinds of primer DNA (SEQ ID NO: 12 and SEQ ID NO: 13). A PCR fragment thus obtained was treated with a restriction enzyme XhoI.

(3) The DNA fragments prepared by the processes (1) and (2) were ligated to each other by a T4DNA ligase and amplified with the use of *Escherichia coli*. Sizes of decomposed substances digested by various kinds of restriction enzymes were checked, and it was thus confirmed that a plasmid having a structure (hereinafter referred to as "CAT-gshA gene cassette") in which gshA is linked to a downstream of the target chloramphenicol-resistant gene (hereinafter abbreviated as CAT) was accomplished. This plasmid was named "pACYC184R-SmaI-E.c.gshA".

(4) Next, a gene region called a replication region for driving autonomic DNA replication in *Cyanobacteria* was cloned. Specifically, a replication region (SEQ ID NO: 11) contained in a plasmid pAQ1, which is present in a bacterial body of a *Cyanobacteria Synechococcus* PCC7002 strain (American Type Culture Collection ATCC27264), was amplified by a PCR method with reference to a document (Akiyama et al. (1999) DNA RESEARCH Vol. 5, 327-334). Sequences of two kinds of PCR primers used in the PCR method are represented by SEQ ID NO: 14 and SEQ ID NO: 15, respectively. A PCR fragment of approximately 3.4 kb thus obtained and a DNA fragment obtained by cleaving the plasmid vector pZero2 (Registered Trademark, Invitrogen Corporation) with the use of the restriction enzyme EcoRV were ligated to each other by a T4DNA ligase and amplified with the use of *Escherichia coli*. Sizes of decomposed substances digested by various kinds of restriction enzymes were checked, and it was thus confirmed that a plasmid having a gene region enabling autonomic replication in the target *Cyanobacteria* was accomplished. This plasmid was named "pZero2-pAQ1-ori".

(5) Finally, a gene cassette expressing *Escherichia coli* gshA by readthrough of CAT was placed on the plasmid autonomically replicating in *Cyanobacteria*. Specifically, PCR amplification was carried out by using, as a template, pACYC184R-SmaI-E.c.gshA produced in the process (3) and using two kinds of PCR primers (SEQ ID NO: 16 and SEQ ID NO: 17). A PCR fragment of approximately 2.7 kb thus obtained and a DNA fragment of approximately 6.2 kb obtained by digesting, with the use of the restriction enzyme StuI, pZero2-pAQ1-ori produced in the process (4) were ligated to each other by a T4DNA ligase and amplified with the use of *Escherichia coli*. Sizes of decomposed substances digested by various kinds of restriction enzymes were checked, and it was thus confirmed that a plasmid having the gene region enabling autonomic DNA replication in the target *Cyanobacteria* and the CAT-gshA gene cassette was accomplished. This plasmid was named "pSyn5".

(6) A plasmid for use in a control experiment to be compared with an experiment of introducing pSyn5 into *Cyanobacteria* was constructed. This plasmid has only CAT and does not have gshA. Specifically, a PCR amplification was carried out using, as a template, pACYC184 and using two kinds of PCR primers (SEQ ID NO: 16 and SEQ ID NO: 18). A PCR fragment of approximately 1.1 kb thus obtained and a DNA fragment of approximately 6.2 kb obtained by digesting, with the use of the restriction enzyme StuI, pZero2-pAQ1-ori produced in the process (4) were ligated to each other by a T4DNA ligase and amplified with the use of *Escherichia coli*. Sizes of decomposed substances digested by various kinds of restriction enzymes were checked, and it was thus confirmed that a plasmid having a gene region enabling autonomic DNA replication in the target *Cyanobacteria* and a CAT gene was accomplished. This plasmid was named "pSyn3".

The plasmids pSyn5 and pSyn3 were separately introduced into respective *Cyanobacteria Synechococcus* PC7002 strains by a known method (see Fringaard et al. (2004) Methods in Molecular Biology, Vol. 274, 325-340). Transformants into which the respective plasmids were introduced were named "E.c.gshA plus strain" and "E.c.gshA minus strain", respectively. In the E.c.gshA plus strain, *Escherichia coli*-derived γ-glutamylcysteine synthetase functions. Meanwhile, in the E.c.gshA minus strain, the *Escherichia coli*-derived γ-glutamylcysteine synthetase is not present.

These two kinds of *Cyanobacteria* were separately inoculated into 80 mL of Daigo medium (medium in which 500 mg of Daigo IMK medium (produced by NIHON PHARMACEUTICAL CO., LTD., Model No. 398-01333), 36 g of artificial seawater SP (produced by NIHON PHARMACEUTICAL CO., LTD., Model No. 395-01343), 1 g of tris(hydroxymethyl)aminomethane (produced by NACALAI, Model No. 35434-21), 1 g of sodium hydrogen carbonate (produced by Wako Pure Chemical Industries, Ltd., Model No. 198-01315), and 10 mg of chloramphenicol (produced by Wako Pure Chemical Industries, Ltd., Model No. 034-10572) are dissolved in 1 L of purified water and subjected to filtration sterilization) and cultured for three days at 30° C. while being stirred with supply of atmosphere and continuously irradiated with light in an amount of 70 μE/m$^2$/second.

Cells contained in 1 mL of a culture thus obtained were collected by centrifugation and were suspended in 0.2 mL of water. Next, after addition of 0.8 mL of acetone, the suspension was stirred vigorously so as to extract pigments. After centrifugation, cell residues were removed to obtain a clear pigment solution, which was then analyzed with a spectrophotometer to measure an absorbance spectrum thereof.

FIG. 18 shows a result of analysis of absorbance spectra of pigments extracted from the E.c.gshA plus strain and E.c.gshA minus strain, each of which is a transformant of *Cyanobacteria*. (a) of FIG. 18 shows an absorbance spectrum of the E.c.gshA plus strain, (b) of FIG. 18 shows an absorbance spectrum of the E.c.gshA minus strain, and (c) of FIG. 18 shows a spectrum obtained by subtracting the spectrum of the E.c.gshA minus strain from the spectrum of the E.c.gshA plus strain. Similarly to the result obtained in Example 9, FIG. 18 shows that also in the case of *Cyanobacteria*, a change in pigment composition occurred in the E.c.gshA plus strain as compared with the E.c.gshA minus strain. This reveals that also in a case where γ-glutamylcysteine synthetase is overexpressed with the use of *Cyanobacteria*, effects on photosynthesis that are similar to those of the GSH1 overexpressing strain produced in Example 1 can be obtained.

Industrial Applicability

According to the present invention, it is possible to more efficiently produce biomass from an alga at lower cost, as compared with a conventional art. Since biomass is expected as a raw material for a biofuel, the present invention is applicable to a wide variety of industries such as energy industry.

The invention claimed is:

1. A method for producing an alga having an increased glutathione concentration in a chloroplast thereof, comprising the steps of:
   introducing, into an alga, a polynucleotide encoding a γ-glutamylcysteine synthetase;
   cultivating the modified alga into which the polynucleotide has been introduced; and
   carrying out screening for the alga having the increased glutathione concentration in the chloroplast, by
   (a) measuring an expression amount and/or an activity of an exogenous protein encoded by the polynucleotide and comparing the expression amount and/or the activity thus measured with an expression amount and/or an activity of an endogenous protein in a wild-type alga of a same species; or
   (b) measuring the glutathione concentration in the chloroplast obtained from modified alga and comparing the glutathione concentration thus measured with the glutathione concentration in the chloroplast of a wild-type alga of the same species cultivated under same conditions.

2. The method according to claim 1, wherein the polynucleotide encoding the γ-glutamylcysteine synthetase is selected from the group consisting of the following (a) to (d):
   (a) a polynucleotide encoding a polypeptide consisting of the amino-acid sequence set forth in SEQ ID NO: 1;
   (b) a polynucleotide encoding a polypeptide which consists of an amino-acid sequence with deletion, substitution, or addition of not more than 10 amino acids in the amino-acid sequence set forth in SEQ ID NO: 1 and which has a γ-glutamylcysteine synthetase activity;
   (c) a polynucleotide consisting of the nucleotide sequence set forth in SEQ ID NO: 2; and
   (d) a polynucleotide which hybridizes under a stringent condition with a polynucleotide consisting of a nucleotide sequence fully complementary to any one of the polynucleotides (a) through (c) and which encodes a polypeptide having a γ-glutamylcysteine synthetase activity,
   wherein said condition is defined by incubation overnight at 42° C. in 5×SSC and then washing in 0.1×SSC at approximately 65° C.

3. A method for producing biomass, comprising the step of cultivating an alga produced by the method as set forth in claim 1.

4. The method according to claim 3, further comprising the step of irradiating the alga with light.

5. The method according to claim 4, wherein the step of irradiating the alga with light is carried out under a condition where nitrogen is not substantially starved.

6. The method of claim 1, wherein the polynucleotide encoding the γ-glutamylcysteine synthetase is a polynucleotide encoding a polypeptide consisting of the amino acid sequence set forth in SEQ ID NO: 1.

7. The method of claim 1, wherein the polynucleotide encoding the γ-glutamylcysteine synthetase is a polynucleotide encoding a polypeptide which consists of an amino acid sequence with a deletion, a substitution, or an addition of not more than 10 amino acids in the amino acid sequence set forth in SEQ ID NO: 1 and which has a γ-glutamylcysteine synthetase activity.

8. The method of claim 1, wherein the polynucleotide encoding the γ-glutamylcysteine synthetase is a polynucleotide consisting of the nucleotide sequence set forth in SEQ ID NO: 2.

9. The method of claim 1, wherein the polynucleotide encoding the γ-glutamylcysteine synthetase is a polynucleotide which hybridizes under a stringent condition defined by incubation overnight at 42° C. in 5×SSC and then washing in 0.1×SSC at approximately 65° C. with a polynucleotide consisting of a nucleotide sequence fully complementary to any one of (a) a polynucleotide consisting of the amino acid sequence set forth in SEQ ID NO: 1, (b) a polynucleotide encoding a polypeptide which consists of an amino acid sequence with deletion, substitution, or addition of one or several amino acids in the amino acid sequence set forth in SEQ ID NO: 1 and which has a γ-glutamylcysteine synthetase activity, or (c) a polynucleotide consisting of the nucleotide sequence set forth in SEQ ID NO: 2.

10. The method of claim 1, wherein the alga is a sta6-positive strain of alga.

11. The method of claim 1, wherein the alga is a sta6-deficient strain of alga.

12. An alga produced by the method according to claim 1.

* * * * *